(12) United States Patent
Almarsson et al.

(10) Patent No.: US 11,203,569 B2
(45) Date of Patent: Dec. 21, 2021

(54) CRYSTAL FORMS OF AMINO LIPIDS

(71) Applicant: ModernaTX, Inc., Cambridge, MA (US)

(72) Inventors: Orn Almarsson, Cambridge, MA (US); Eugene Cheung, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 60 days.

(21) Appl. No.: 16/493,789

(22) PCT Filed: Mar. 15, 2018

(86) PCT No.: PCT/US2018/022740
§ 371 (c)(1),
(2) Date: Sep. 13, 2019

(87) PCT Pub. No.: WO2018/170322
PCT Pub. Date: Sep. 20, 2018

(65) Prior Publication Data
US 2020/0131116 A1  Apr. 30, 2020

Related U.S. Application Data

(60) Provisional application No. 62/471,908, filed on Mar. 15, 2017.

(51) Int. Cl.
| | | |
|---|---|---|
| *C07C 229/24* | (2006.01) | |
| *C07C 55/07* | (2006.01) | |
| *C07C 65/03* | (2006.01) | |
| *C07C 227/16* | (2006.01) | |
| *C07C 229/12* | (2006.01) | |

(52) U.S. Cl.
CPC ............ *C07C 229/24* (2013.01); *C07C 55/07* (2013.01); *C07C 65/03* (2013.01); *C07C 227/16* (2013.01); *C07C 229/12* (2013.01); *C07B 2200/13* (2013.01)

(58) Field of Classification Search
CPC combination set(s) only.
See application file for complete search history.

(56) References Cited

U.S. PATENT DOCUMENTS

| | | | |
|---|---|---|---|
| 3,872,171 A | 3/1975 | Cronin et al. | |
| 4,125,544 A | 11/1978 | Dygos | |
| 4,957,735 A | 9/1990 | Huang | |
| 5,807,861 A | 9/1998 | Klein et al. | |
| 6,143,276 A | 11/2000 | Unger | |
| 6,303,378 B1 | 10/2001 | Bridenbaugh et al. | |
| 6,395,253 B2 | 5/2002 | Levy et al. | |
| 6,652,886 B2 | 11/2003 | Ahn et al. | |
| 6,696,038 B1 | 2/2004 | Mahato et al. | |
| 7,268,120 B1 | 9/2007 | Horton et al. | |
| 7,371,404 B2 | 5/2008 | Panzner et al. | |
| 7,943,168 B2 | 5/2011 | Schlesinger et al. | |
| 8,058,069 B2 | 11/2011 | Yaworski et al. | |
| 8,158,601 B2 | 4/2012 | Chen et al. | |
| 8,420,123 B2 | 4/2013 | Troiano et al. | |
| 8,440,614 B2 | 5/2013 | Castor | |
| 8,449,916 B1 | 5/2013 | Bellaire et al. | |
| 8,450,298 B2 | 5/2013 | Mahon et al. | |
| 8,460,696 B2 | 6/2013 | Slobodkin et al. | |
| 8,460,709 B2 | 6/2013 | Ausborn et al. | |
| 8,563,041 B2 | 10/2013 | Grayson et al. | |
| 8,568,784 B2 | 10/2013 | Lillard et al. | |
| 8,569,256 B2 | 10/2013 | Heyes et al. | |
| 8,580,297 B2 | 11/2013 | Essler et al. | |
| 8,603,499 B2 | 12/2013 | Zale et al. | |
| 8,603,500 B2 | 12/2013 | Zale et al. | |
| 8,603,501 B2 | 12/2013 | Zale et al. | |
| 8,603,534 B2 | 12/2013 | Zale et al. | |
| 8,603,535 B2 | 12/2013 | Troiano et al. | |
| 8,609,142 B2 | 12/2013 | Troiano et al. | |
| 8,613,951 B2 | 12/2013 | Zale et al. | |
| 8,613,954 B2 | 12/2013 | Zale et al. | |
| 8,617,608 B2 | 12/2013 | Zale et al. | |
| 8,618,240 B2 | 12/2013 | Podobinski et al. | |
| 8,637,083 B2 | 1/2014 | Troiano et al. | |
| 8,642,076 B2 | 2/2014 | Manoharan et al. | |

(Continued)

FOREIGN PATENT DOCUMENTS

| | | |
|---|---|---|
| AU | 652831 B2 | 9/1994 |
| CN | 102068701 A | 5/2011 |

(Continued)

OTHER PUBLICATIONS

Dong et al., "Lipopeptide nanoparticles for potent and selective siRNA delivery in rodents and nonhuman primates," PNAS, Mar. 2014, vol. 111, No. 11, 3955-3960; 5753-5754.

Hashiba et al., "pH-labile PEGylation of siRNA-loaded lipid nanoparticle improves active targeting and gene silencing activity in hepatocytes," Journal of Controlled Release (2017) vol. 262, 239-246.

Jaiswal et al., "Nanostructured lipid carriers and their current application in targeted drug delivery," Artificial Cells, Nanomedicine, and Biotechnology (2016) 44: 27-40.

Mohtar et al., "Solid Lipid Nanoparticles of Atovaquone Based on 24 Full-Factorial Design," Iranian Journal of Pharmaceutical Research (2015) 14(4): 989-1000.

Ramteke, K. H. et al., "Solid Lipid Nanoparticle: A Review," IOSR Journal of Pharmacy, Nov.-Dec. 2012, 2(60): 34-44.

(Continued)

*Primary Examiner* — Heidi Reese
(74) *Attorney, Agent, or Firm* — Cooley LLP; Heidi A. Erlacher; Christine C. Pemberton

(57) ABSTRACT

Provided herein are novel solid forms of each of four compounds: (1) heptadecan-9-yl 8-((2-hydroxyethyl)amino) octanoate ("Compound 1"), (2) heptadecan-9-yl 8-((2-hydroxyethyl)(6-oxo-6-(undecyloxy)hexyl)amino)octanoate ("Compound 2"), (3) heptadecan-9-yl 8-((2-hydroxyethyl) (8-(nonyloxy)-8-oxooctyl)amino)octanoate ("Compound 3"), and (6Z,9Z,28Z,31Z)-heptatriaconta-6,9,28,31-tetraen-19-yl 4-(dimethylamino)butanoate ("MC3"), and related compositions and methods.

20 Claims, 31 Drawing Sheets

(56) References Cited

U.S. PATENT DOCUMENTS

| | | |
|---|---|---|
| 8,652,487 B2 | 2/2014 | Maldonado |
| 8,652,528 B2 | 2/2014 | Troiano et al. |
| 8,663,599 B1 | 3/2014 | Sung et al. |
| 8,663,700 B2 | 3/2014 | Troiano et al. |
| 8,668,926 B1 | 3/2014 | Mousa et al. |
| 8,685,368 B2 | 4/2014 | Reineke |
| 8,691,750 B2 | 4/2014 | Constein et al. |
| 8,697,098 B2 | 4/2014 | Perumal et al. |
| 8,703,204 B2 | 4/2014 | Bloom et al. |
| 8,709,483 B2 | 4/2014 | Farokhzad et al. |
| 8,715,736 B2 | 5/2014 | Sachdeva et al. |
| 8,715,741 B2 | 5/2014 | Maitra et al. |
| 8,728,527 B2 | 5/2014 | Singh |
| 8,734,832 B2 | 5/2014 | O'Hagan et al. |
| 8,734,846 B2 | 5/2014 | Ali et al. |
| 8,734,853 B2 | 5/2014 | Sood et al. |
| 8,802,644 B2 | 8/2014 | Chen et al. |
| 9,006,487 B2 | 4/2015 | Anderson et al. |
| 9,029,590 B2 | 5/2015 | Colletti et al. |
| 9,394,234 B2 | 7/2016 | Chen et al. |
| 9,717,690 B2 | 8/2017 | Guild et al. |
| 9,738,593 B2 | 8/2017 | Ansell et al. |
| 9,867,888 B2 | 1/2018 | Benenato |
| 9,868,691 B2 * | 1/2018 | Benenato ............ A61K 38/1725 |
| 9,868,692 B2 | 1/2018 | Benenato |
| 9,868,693 B2 | 1/2018 | Benenato |
| 10,106,490 B2 | 10/2018 | Du |
| 10,166,298 B2 | 1/2019 | Ansell et al. |
| 10,392,341 B2 | 8/2019 | Benenato et al. |
| 10,799,463 B2 | 10/2020 | Benenato et al. |
| 10,857,105 B2 | 12/2020 | Benenato et al. |
| 2003/0073619 A1 | 4/2003 | Mahato et al. |
| 2003/0092653 A1 | 5/2003 | Kisich et al. |
| 2004/0142474 A1 | 7/2004 | Mahato et al. |
| 2005/0222064 A1 | 10/2005 | Vargeese et al. |
| 2006/0008910 A1 | 1/2006 | Maclachlan et al. |
| 2006/0083780 A1 | 4/2006 | Heyes et al. |
| 2006/0172003 A1 | 8/2006 | Meers et al. |
| 2006/0204566 A1 | 9/2006 | Smyth-Templeton et al. |
| 2007/0252295 A1 | 11/2007 | Panzner et al. |
| 2009/0042825 A1 | 2/2009 | Matar et al. |
| 2009/0042829 A1 | 2/2009 | Matar et al. |
| 2011/0009641 A1 | 1/2011 | Anderson et al. |
| 2011/0200582 A1 | 8/2011 | Baryza et al. |
| 2011/0244026 A1 | 10/2011 | Guild et al. |
| 2012/0136073 A1 | 5/2012 | Yang et al. |
| 2012/0177724 A1 | 7/2012 | Irvine et al. |
| 2012/0178702 A1 | 7/2012 | Huang |
| 2012/0226085 A1 | 9/2012 | Ishihara et al. |
| 2012/0295832 A1 | 11/2012 | Constien et al. |
| 2013/0017223 A1 | 1/2013 | Hope et al. |
| 2013/0064894 A1 | 3/2013 | Martin et al. |
| 2013/0065942 A1 | 3/2013 | Matar et al. |
| 2013/0090372 A1 | 4/2013 | Budzik et al. |
| 2013/0108685 A1 | 5/2013 | Kuboyama et al. |
| 2013/0115273 A1 | 5/2013 | Yang et al. |
| 2013/0115274 A1 | 5/2013 | Knopov et al. |
| 2013/0116307 A1 | 5/2013 | Heyes et al. |
| 2013/0122104 A1 | 5/2013 | Yaworski et al. |
| 2013/0123338 A1 | 5/2013 | Heyes et al. |
| 2013/0129785 A1 | 5/2013 | Manoharan et al. |
| 2013/0130348 A1 | 5/2013 | Gu et al. |
| 2013/0142868 A1 | 6/2013 | Hoekman et al. |
| 2013/0142876 A1 | 6/2013 | Howard et al. |
| 2013/0150625 A1 | 6/2013 | Budzik et al. |
| 2013/0156845 A1 | 6/2013 | Manoharan et al. |
| 2013/0156849 A1 | 6/2013 | de Fougerolles et al. |
| 2013/0164400 A1 | 6/2013 | Knopov et al. |
| 2013/0171241 A1 | 7/2013 | Geall |
| 2013/0172406 A1 | 7/2013 | Zale et al. |
| 2013/0178541 A1 | 7/2013 | Stanton et al. |
| 2013/0183244 A1 | 7/2013 | Hanes et al. |
| 2013/0183355 A1 | 7/2013 | Jain et al. |
| 2013/0183372 A1 | 7/2013 | Schutt et al. |
| 2013/0183373 A1 | 7/2013 | Schutt et al. |
| 2013/0183375 A1 | 7/2013 | Schutt et al. |
| 2013/0189351 A1 | 7/2013 | Geall |
| 2013/0195759 A1 | 8/2013 | Mirkin et al. |
| 2013/0195765 A1 | 8/2013 | Gho et al. |
| 2013/0195967 A1 | 8/2013 | Guild et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236500 A1 | 9/2013 | Zale et al. |
| 2013/0236533 A1 | 9/2013 | Von Andrian et al. |
| 2013/0236550 A1 | 9/2013 | Ausborn et al. |
| 2013/0243827 A1 | 9/2013 | Troiano et al. |
| 2013/0243848 A1 | 9/2013 | Lobovkina et al. |
| 2013/0243867 A1 | 9/2013 | Mohapatra et al. |
| 2013/0251766 A1 | 9/2013 | Zale et al. |
| 2013/0251816 A1 | 9/2013 | Zale et al. |
| 2013/0251817 A1 | 9/2013 | Zale et al. |
| 2013/0266617 A1 | 10/2013 | Mirosevich et al. |
| 2013/0273117 A1 | 10/2013 | Podobinski et al. |
| 2013/0274504 A1 | 10/2013 | Colletti et al. |
| 2013/0274523 A1 | 10/2013 | Bawiec, III et al. |
| 2013/0280334 A1 | 10/2013 | Karp et al. |
| 2013/0280339 A1 | 10/2013 | Zale et al. |
| 2013/0295183 A1 | 11/2013 | Troiano et al. |
| 2013/0295191 A1 | 11/2013 | Troiano et al. |
| 2013/0302432 A1 | 11/2013 | Zale et al. |
| 2013/0302433 A1 | 11/2013 | Troiano et al. |
| 2013/0315831 A1 | 11/2013 | Shi et al. |
| 2013/0330401 A1 | 12/2013 | Payne et al. |
| 2013/0338210 A1 | 12/2013 | Manoharan et al. |
| 2013/0344158 A1 | 12/2013 | Zale et al. |
| 2014/0017327 A1 | 1/2014 | Cheng et al. |
| 2014/0017329 A1 | 1/2014 | Mousa |
| 2014/0037573 A1 | 2/2014 | Eliasof et al. |
| 2014/0037660 A1 | 2/2014 | Folin-Mleczek et al. |
| 2014/0037714 A1 | 2/2014 | Quay et al. |
| 2014/0039032 A1 | 2/2014 | Kumboyama et al. |
| 2014/0044772 A1 | 2/2014 | Maclachlan et al. |
| 2014/0044791 A1 | 2/2014 | Basilion et al. |
| 2014/0045913 A1 | 2/2014 | Kumboyama et al. |
| 2014/0050775 A1 | 2/2014 | Slobodkin et al. |
| 2014/0057109 A1 | 2/2014 | Mechen et al. |
| 2014/0065172 A1 | 3/2014 | Echeverri et al. |
| 2014/0065204 A1 | 3/2014 | Hayes et al. |
| 2014/0065228 A1 | 3/2014 | Yarowoski et al. |
| 2014/0079774 A1 | 3/2014 | Brinker et al. |
| 2014/0093575 A1 | 4/2014 | Hammond et al. |
| 2014/0093579 A1 | 4/2014 | Zale et al. |
| 2014/0113137 A1 | 4/2014 | Podobinski et al. |
| 2014/0121263 A1 | 5/2014 | Fitzgerald et al. |
| 2014/0121393 A1 | 5/2014 | Manoharan et al. |
| 2014/0134260 A1 | 5/2014 | Heyes et al. |
| 2014/0141070 A1 | 5/2014 | Geall et al. |
| 2014/0141089 A1 | 5/2014 | Liang |
| 2014/0141483 A1 | 5/2014 | Bossard et al. |
| 2014/0142165 A1 | 5/2014 | Grayson et al. |
| 2014/0142254 A1 | 5/2014 | Fonnum et al. |
| 2014/0161830 A1 | 6/2014 | Anderson et al. |
| 2014/0308304 A1 | 10/2014 | Manoharan et al. |
| 2015/0174260 A1 | 6/2015 | Yang et al. |
| 2015/0174261 A1 | 6/2015 | Kuboyama et al. |
| 2015/0239926 A1 | 8/2015 | Payne et al. |
| 2015/0284317 A1 | 10/2015 | Colletti et al. |
| 2015/0343062 A1 | 12/2015 | Kuboyama et al. |
| 2015/0376115 A1 | 12/2015 | Ansell et al. |
| 2016/0002178 A1 | 1/2016 | Fenton et al. |
| 2016/0009657 A1 | 1/2016 | Anderson et al. |
| 2016/0151284 A1 | 6/2016 | Heyes et al. |
| 2017/0119904 A1 | 5/2017 | Ansell et al. |
| 2018/0201572 A1 | 7/2018 | Benenato |
| 2018/0273467 A1 | 9/2018 | Benenato |
| 2018/0303925 A1 | 10/2018 | Weissman et al. |
| 2018/0333366 A1 | 11/2018 | Benenato et al. |
| 2018/0369419 A1 | 12/2018 | Benenato et al. |
| 2019/0016669 A1 | 1/2019 | Benenato et al. |
| 2019/0314292 A1 | 10/2019 | Benenato et al. |
| 2019/0314524 A1 | 10/2019 | Ansell et al. |
| 2019/0336452 A1 | 11/2019 | Brader et al. |

(56) References Cited

U.S. PATENT DOCUMENTS

| | | | |
|---|---|---|---|
| 2020/0069599 A1 | 3/2020 | Smith et al. | |
| 2020/0129445 A1 | 4/2020 | Patel | |
| 2021/0087135 A1 | 3/2021 | Benenato et al. | |

FOREIGN PATENT DOCUMENTS

| | | |
|---|---|---|
| CN | 102204920 A | 10/2011 |
| CN | 102813929 A | 12/2012 |
| CN | 104644555 A | 5/2015 |
| EP | 737750 | 10/1996 |
| EP | 1404860 B1 | 5/2002 |
| EP | 2073848 B1 | 8/2013 |
| JP | 2000-169864 A | 6/2000 |
| WO | WO 1993/014778 | 8/1993 |
| WO | WO 1999/014346 A2 | 3/1999 |
| WO | WO 1999/052503 | 10/1999 |
| WO | WO 1999/54344 A1 | 10/1999 |
| WO | WO 2003/086280 | 10/2003 |
| WO | WO 2005/034979 A2 | 4/2005 |
| WO | WO 2006/063249 A2 | 6/2006 |
| WO | WO 2008/042973 A2 | 4/2008 |
| WO | WO 2009/024599 | 2/2009 |
| WO | WO 2009/053686 A1 | 4/2009 |
| WO | WO 2009/086558 A1 | 7/2009 |
| WO | WO 2009/127060 A1 | 10/2009 |
| WO | WO 2009/129385 A1 | 10/2009 |
| WO | WO 2009/129395 A1 | 10/2009 |
| WO | WO 2010/030739 A1 | 3/2010 |
| WO | WO 2010/042877 A1 | 4/2010 |
| WO | WO 2010/053572 A2 | 5/2010 |
| WO | WO 2010/054406 A1 | 5/2010 |
| WO | WO 2010/088537 A2 | 8/2010 |
| WO | WO 2010/129709 A1 | 11/2010 |
| WO | WO 2011/058990 A1 | 5/2011 |
| WO | WO 2011/068810 A1 | 6/2011 |
| WO | WO 2011/127255 A1 | 10/2011 |
| WO | WO 2012/000104 A1 | 1/2012 |
| WO | WO 2012/006376 A2 | 1/2012 |
| WO | WO 2012/006378 A1 | 1/2012 |
| WO | WO 2012/030901 A1 | 3/2012 |
| WO | WO 2012/031043 A1 | 3/2012 |
| WO | WO 2012/031046 A2 | 3/2012 |
| WO | WO 2012/054365 A2 | 4/2012 |
| WO | WO 2012/129483 A1 | 9/2012 |
| WO | WO 2012/149252 A2 | 11/2012 |
| WO | WO 2012/149255 A2 | 11/2012 |
| WO | WO 2012/149265 A2 | 11/2012 |
| WO | WO 2012/149282 A2 | 11/2012 |
| WO | WO 2012/149301 A2 | 11/2012 |
| WO | WO 2012/149376 A2 | 11/2012 |
| WO | WO 2012/149393 A2 | 11/2012 |
| WO | WO 2012/153338 A2 | 11/2012 |
| WO | WO 2012/170889 A1 | 12/2012 |
| WO | WO 2012/170930 A1 | 12/2012 |
| WO | WO 2013/006825 A1 | 1/2013 |
| WO | WO 2013/006834 A1 | 1/2013 |
| WO | WO 2013/006837 A1 | 1/2013 |
| WO | WO 2013/006838 A1 | 1/2013 |
| WO | WO 2013/006842 A2 | 1/2013 |
| WO | WO 2013/016058 A1 | 1/2013 |
| WO | WO 2013/033438 A2 | 3/2013 |
| WO | WO 2013/033563 A1 | 3/2013 |
| WO | WO 2013/036835 A1 | 3/2013 |
| WO | WO 2013/049328 A1 | 4/2013 |
| WO | WO 2013/052167 A2 | 4/2013 |
| WO | WO 2013/056132 A2 | 4/2013 |
| WO | WO 2013/057715 A1 | 4/2013 |
| WO | WO 2013/059496 A1 | 4/2013 |
| WO | WO 2013/059922 A1 | 5/2013 |
| WO | WO 2013/064911 A2 | 5/2013 |
| WO | WO 2013/066903 A1 | 5/2013 |
| WO | WO 2013/067537 A1 | 5/2013 |
| WO | WO 2013/070872 A2 | 5/2013 |
| WO | WO 2013/072929 A2 | 5/2013 |
| WO | WO 2013/086322 A1 | 6/2013 |
| WO | WO 2013/086354 A1 | 6/2013 |
| WO | WO 2013/086373 A1 | 6/2013 |
| WO | WO 2013/086526 A1 | 6/2013 |
| WO | WO 2013/087083 A1 | 6/2013 |
| WO | WO 2013/087791 A1 | 6/2013 |
| WO | WO 2013/093648 A2 | 6/2013 |
| WO | WO 2013/135359 A1 | 9/2013 |
| WO | WO 2013/143555 A1 | 10/2013 |
| WO | WO 2013/143683 A1 | 10/2013 |
| WO | WO 2013/148186 A1 | 10/2013 |
| WO | WO 2013/148541 A1 | 10/2013 |
| WO | WO 2013/149141 A1 | 10/2013 |
| WO | WO 2013/151650 A1 | 10/2013 |
| WO | WO 2013/155487 A1 | 10/2013 |
| WO | WO 2013/155493 A9 | 10/2013 |
| WO | WO 2013/158127 A1 | 10/2013 |
| WO | WO 2013/158579 A1 | 10/2013 |
| WO | WO 2013/166498 A1 | 11/2013 |
| WO | WO 2013/173693 A1 | 11/2013 |
| WO | WO 2013/177419 A2 | 11/2013 |
| WO | WO 2013/177421 A2 | 11/2013 |
| WO | WO 2013/185069 A1 | 12/2013 |
| WO | WO 2014/007398 A1 | 1/2014 |
| WO | WO 2014/008334 A1 | 1/2014 |
| WO | WO 2014/026284 A1 | 2/2014 |
| WO | WO 2014/028487 A1 | 2/2014 |
| WO | WO 2014/028763 A1 | 2/2014 |
| WO | WO 2014/047649 A1 | 3/2014 |
| WO | WO 2014/052634 A1 | 4/2014 |
| WO | WO 2014/054026 A1 | 4/2014 |
| WO | WO 2014/071072 A2 | 5/2014 |
| WO | WO 2014/072997 A1 | 5/2014 |
| WO | WO 2014/089486 A1 | 6/2014 |
| WO | WO 2014/144196 A1 | 9/2014 |
| WO | WO 2014/160243 A1 | 10/2014 |
| WO | WO 2014/172045 A1 | 10/2014 |
| WO | WO 2011/136368 A1 | 11/2014 |
| WO | WO 2014/182661 A2 | 11/2014 |
| WO | WO 2014/210356 A1 | 12/2014 |
| WO | WO 2015/011633 A1 | 1/2015 |
| WO | WO 2015/130584 A2 | 9/2015 |
| WO | WO 2015/154002 A1 | 10/2015 |
| WO | WO 2015/199952 A1 | 12/2015 |
| WO | WO 2016/004202 A1 | 1/2016 |
| WO | WO 2016/004318 A1 | 1/2016 |
| WO | WO 2016/118697 A1 | 7/2016 |
| WO | WO 2016/118724 A1 | 7/2016 |
| WO | WO 2016/176330 A1 | 11/2016 |
| WO | WO 2017/015630 A2 | 1/2017 |
| WO | WO 2017/031232 A1 | 2/2017 |
| WO | WO 2017/049245 A2 | 3/2017 |
| WO | WO 2017/070616 A2 | 4/2017 |
| WO | WO 2017/070626 A1 | 4/2017 |
| WO | WO 2017/075531 A1 | 5/2017 |
| WO | WO 2017/099823 A1 | 6/2017 |
| WO | WO 2017/100744 A1 | 6/2017 |
| WO | WO 2017/112865 A1 | 6/2017 |
| WO | WO 2017/127750 A1 | 7/2017 |
| WO | WO 2017/180917 A2 | 10/2017 |
| WO | WO 2017/192470 A1 | 11/2017 |
| WO | WO 2017/201317 A1 | 11/2017 |
| WO | WO 2017/201325 A1 | 11/2017 |
| WO | WO 2017/201328 A1 | 11/2017 |
| WO | WO 2017/201332 A1 | 11/2017 |
| WO | WO 2017/201333 A1 | 11/2017 |
| WO | WO 2017/201340 A2 | 11/2017 |
| WO | WO 2017/201342 A1 | 11/2017 |
| WO | WO 2017/201346 A1 | 11/2017 |
| WO | WO 2017/201347 A1 | 11/2017 |
| WO | WO 2017/201348 A1 | 11/2017 |
| WO | WO 2017/201349 A1 | 11/2017 |
| WO | WO 2017/201350 A1 | 11/2017 |
| WO | WO 2017/201352 A1 | 11/2017 |
| WO | WO 2017/218704 A1 | 12/2017 |
| WO | WO 2018/078053 A1 | 5/2018 |
| WO | WO 2018/081480 A1 | 5/2018 |
| WO | WO 2018/081638 A1 | 5/2018 |
| WO | WO 2018/089540 A1 | 5/2018 |
| WO | WO 2018/170260 A1 | 9/2018 |

(56) References Cited

FOREIGN PATENT DOCUMENTS

| | | |
|---|---|---|
| WO | WO 2018/170270 A1 | 9/2018 |
| WO | WO 2018/170306 A1 | 9/2018 |
| WO | WO 2018/170336 A1 | 9/2018 |
| WO | WO 2018/191719 A1 | 10/2018 |
| WO | WO 2018/232120 A1 | 12/2018 |
| WO | WO 2019/046809 A1 | 3/2019 |
| WO | WO 2019/089828 A1 | 5/2019 |
| WO | WO 2019/152557 A1 | 8/2019 |
| WO | WO 2019/193183 A2 | 10/2019 |
| WO | WO 2019/202035 A1 | 10/2019 |
| WO | WO 2020/002525 A1 | 1/2020 |
| WO | WO 2020/061457 A1 | 3/2020 |
| WO | WO 2020/123300 A2 | 6/2020 |

OTHER PUBLICATIONS

Sabnis et al., "A Novel Amino Lipid Series for mRNA Delivery: Improved Endosomal Escape and Sustained Pharmacology and Safety in Non-human Primates," Molecular Therapy, Jun. 2018, vol. 26, No. 6, pp. 1509-1519.
Yadava, P. et al., "Effect of Lyophilization and Freeze-thawing on the Stability of siRNA-liposome Complexes," AAPS PharmSciTech, Jun. 2008, 9(2): 335-341.
Abdelwahed et al., "Freeze-drying of nanoparticles: Formulation, process and storage considerations," Advanced Drug Delivery Reviews 58 (2006) 1688-1713.
Akinc et al., Development of Lipidoid-siRNA Formulations for Systemic Delivery to the Liver, Molecular Therapy, May 2009, vol. 17, No. 5, pp. 872-879.
Akinc et al., Targeted Delivery of RNAi Therapeutics With Endogenous and Exogenous Ligand-Based Mechanisms, Mol Ther. 2010 18(7):1357-1364.
Anderson, D.M. et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.
Andries, O., et al., Comparison of the gene transfer efficiency of mRNA/GL67 and pDNA/GL67 complexes in respiratory cells. Mol Pharmaceutics. 2012; 9: 2136-2145.
Ashizawa et al., "Liposomal delivery of nucleic acid-based anti-cancer therapeutics: BP-100-1.01," Expert Opin. Drug Deliv., (2014) 12(7):1107-1120.
Bag, J., Recovery of normal protein synthesis in heat-shocked chicken myotubes by liposome-mediated transfer of mRNAs. Can. J. Biochem. Cell Biol. 1985; 63(3): 231-235.
Belliveau, N.M., et al., Microfluidic synthesis of highly potent limit-size lipid nanoparticles for in vivo delivery of siRNA. Mol Ther Nucleic Acids. Aug. 2012; 1(8): e37.
Bettinger, T. et al., Peptide-mediated RNA delivery: a novel approach for enhanced transfection of primary and post-mitotic cells. Nucleic Acids Res. Sep. 15, 2001;29(18):3882-91.
Bolhassani A., et al., Improvement of Different Vaccine Delivery Systems For Cancer Therapy, Molecular Cancer, Biomed Central, London, GB, 2011, vol. 10, No. 3, pp. 1-20.
Bonehill, A., et al., Single-step antigen loading and activation of dendritic cells by mRNA electroporation for the purpose of therapeutic vaccination in melanoma patients. Clin Cancer Res. May 2009; 15(10): 3366-3375.
Bouxsein, N.F., et al., Structure and gene silencing activities of monovalent and pentavalent cationic lipid vectors complexed with siRNA. Biochem. 2007; 46(16): 4785-4792.
Chen, D., et al., Rapid discovery of potent siRNA-containing lipid nanoparticles enabled by controlled microfluidic formulation. J Am Chem Soc. 2012; 134: 6948-6951.
Chen, S. et al., "Development of lipid nanoparticle formulations of siRNA for hepatocyte gene silencing following subcutaneous administration," J Control Release, 2014, 196, 106-112.

Cun, Dongmei, et al., Preparation and characterization of poly(DL-lactide-co-glycolide) nanoparticles for siRNA delivery. International Journal of Pharmaceutics 390 (2010) 70-75.
Dahlman, James E. et al., In vivo endothelial siRNA delivery using polymeric nanoparticles with low molecular weight, Nature Nanotechnology, 2014, No. vol.#, pp. 1-8.
Delehanty, James B., Peptides for Specific Intracellular Delivery and Targeting of Nanoparticles: Implications for Developing Nanoparticle-Mediated Drug Delivery, Future Science, Therapeutic Delivery, 2010, vol. 1, No. 3, pp. 411-433.
El Ouahabi, A., et al., Double long-chain amidine liposome-mediated self replicating RNA transfection. FEBS Letters. Feb. 1996; 380(1-2): 108-112.
Felgner, PL Cationic lipid/polynucleotide condensates for in vitro and in vivo polynucleotide delivery—the cytofectins. J. of Liposome Research. 1993; 3(1): 3-16.
Felgner, PL Particulate systems and polymers for in vitro and in vivo delivery of polynucleotides. Adv. Drug Delivery Rev. 1990; 5(3): 163-187.
Felgner, PL, et al., Lipofection: a highly efficient, lipid-mediated DNA-transfection procedure. Proc Natl Acad Sci U SA. Nov. 1987;84(21):7413-7.
Gao, X. et al., Nonviral gene delivery: what we know and what is next. AAPS J. Mar. 23, 2007;9(1):E92-104.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
He, K. et al., Synthesis and Separation of Diastereomers of Ribonucleoside 5'-(alpha-P-Borano)triphosphates. J Org Chem. Aug. 21, 1998;63(17):5769-5773.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Hoerr, I. et al., In vivo application of RNA leads to induction of specific cytotoxic T lymphocytes and antibodies. EurJ Immunol. Jan. 2000;30(1):1-7.
Jayaraman et al., "Maximizing the Potency of siRNA Lipid Nanoparticles for Hepatic Gene Silencing In Vivo," Angew. Chem. Int. Ed. 2012, 51, 8529-8533.
Juliano, R.L., et al., Cell-targeting and cell-penetrating peptides for delivery of therapeutic and imaging agents. Wiley Interdisciplinary Reviews: Nanomedicine and Nanobiotechnology. May/Jun. 2009; 1(3): 324-335.
Kang, Hyunmin, Inhibition of MDR1 Gene Expression by Chimeric HNA Antisense Oligonucleotides, Nucleic Acids Research, 2004, vol. 32, No. 14, pp. 4411-4419.
Kariko et al., Phosphate-enhanced transfection of cationic lipid-complexed mRNA and plasmid DNA. Biochimica et Biophysica Acta. 1998. 1369:320-34.
Kariko, K., et al., In vivo protein expression from mRNA delivered into adult rat brain. J. of Neuroscience Methods. Jan. 2001; 105(1): 77-86.
Kariko, K., et al., Incorporation of pseudouridine into mRNA yields superior nonimmunogenic vector with increased translational capacity and biological stability, Molecular Therapy, Nature Publishing Group, GB, vol. 16, No. 11, Nov. 1, 2008 (Nov. 1, 2008), pp. 1833-1840.
Keown, Wa, et al., Methods for Introducing DNA into Mammalian Cells. Methods in Enzymology, 1990, 185:527-37.
Kirpotin, D.B., et al., Antibody targeting of long-circulating lipidic nanoparticles does not increase tumor localization but does increase internalization in animal models. Cancer Res. 2006; 66: 6732-6740.
Kozielski, Kristen L. et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8,' No. 4 ',pp. 3232-3241.
Lai, S.K., et al., Mucus-penetrating nanoparticles for drug and gene delivery to mucosal tissues. Adv Drug Deliv Rev. Feb. 27, 2009; 61(2): 158-171.
Lai, S.K., et al., Rapid transport of large polymeric nanoparticles in fresh undiluted human mucus. PNAS. Jan. 30, 2007; 104(5): 1482-1487.

(56) References Cited

OTHER PUBLICATIONS

Lee, Justin B. et al., Lipid Nanoparticle siRNA Systems for Silencing The Androgen Receptor In Human Prostate Cancer in Vivo, International Journal of Cancer, 2012, vol. 131, pp. 781-790.
Lehto, T., et al., Cell-penetrating peptides for the delivery of nucleic acids. Expert Opin. Drug Deliv. Jul. 2012; 9(7): 823-836.
Leung et al., "Lipid Nanoparticles for Short Interfering RNA Delivery", Advances in Genetics, vol. 88, Chapter 4, pp. 71-110.
Lewis, David, Dynamic Polyconjugates (DPC) Technology: An elegant solution to the siRNA delivery problem. Arrowhead Research Corp (NASDAQ: ARWR). Nov. 2011.
Lewis, R., et al., "Studies of the Thermotropie Phase Behavior of Phosphatidylcholines Containing 2-Alkyl Substituted Fatty Alkyl Chains: A New Class of Phosphatidylcholines Forming Inverted Nonlamellar Phases," Biophysical Journal, Apr. 1994, vol. 66, pp. 1088-1103.
Li, L. et al., Overcoming obstacles to develop effective and safe siRNA therapeutics. Expert Opin Biol Ther. May 2009; 9(5): 609-19.
Li, L. et al., Preparation and gene delivery of alkaline amino acids-based cationic liposomes. Arch Pharm Res. Jul. 2008;31(7):924-31. Epub Aug. 14, 2008.
Lian, T. et al., Trends and developments in liposome drug delivery systems. J Pharm Sci. Jun. 2001;90(6):667-80.
Lopez-Berestein, G. et al., Treatment of systemic fungal infections with liposomal amphotericin B. Arch Intern Med. Nov. 1989;149(11):2533-6.
Love et al., Lipid-like materials for low-dose, in vivo gene silencing, PNAS vol. 107 No. 5, pp. 1864-1869, Feb. 2, 2010.
M. Kanapathipillai, et al., Nanoparticle targeting of anti-cancer drugs that alter intracellular signaling or influence the tumor microenvironment, Adv. Drug Deliv. Rev. (2014), , pp. 1-12.
Magee, W .E. et al., Marked stimulation of lymphocyte-mediated attack on tumor cells by target-directed liposomes containing immune RNA, Cancer Res., 1978, 38(4):1173-6.
Malone, R.W. et al., Cationic liposome-mediated RNA transfection. Proc Natl Acad Sci U S A. Aug. 1989;86 (16):6077-81.
Martinon, F. et al., Induction of virus-specific cytotoxic T lymphocytes in vivo by liposome-entrapped mRNA. Eur J Immunol. Jul. 1993;23(7):1719-22.
Maskarinec et al., "Direct Observation of Poloxamer 188 Insertion into Lipid Monolayers," Biophys J., Mar. 2002, vol. 82, 1453-1459.
Maurer, N., et al., Spontaneous entrapment of polynucleotides upon electrostatic interaction with ethanol-destabilized cationic liposomes. Biophys J. May 2001; 80(5): 2310-2326.
Midoux et al., Lipid-based mRNA vaccine delivery systems. Expert Rev Vaccines. Feb. 2015;14(2):221-34. doi: 10.1586/14760584. 2015.986104. Epub Dec. 26, 2014. Review.
Mishra, R.K. et al., Improved leishmanicidal effect of phosphorothioate antisense oligonucleotides by LDL-mediated delivery. Biochim Biophys Acta. Nov. 7, 1995;1264(2):229-37.
Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Morissette et al., "High-throughput crystallization: polymorphs, salts, co-crystals and solvates of pharmaceutical solids," Advanced Drug Delivery Reviews 56 (2004) 275-300.
Müller et al, "Solid lipid nanoparticles (SLN) for controlled drug delivery—a review of the state of the art," European Journal of Pharmaceutics and Biopharmaceutics, 50 (2000) 161-177.
Nair, S. et al., Soluble proteins delivered to dendritic cells via pH-sensitive liposomes induce primary cytotoxic T lymphocyte responses in vitro. J Exp Med. Feb. 1, 1992;175(2):609-12.
Okumura, K., et al., Bax mRNA therapy using cationic liposomes for human malignant melanoma. J Gene Med. 2008; 10: 910-917.
Oster, C.G., et al. Comparative study of DNA encapsulation into PLGA microparticles using modified double emulsion methods and spray drying techniques. Journal of Microencapsulation, May 2005; 22(3): 235-244.

Parker et al., Targeting of Polyelectrolyte RNA Complexes to Cell Surface Integrins as an Efficient, Cytoplasmic Transfection Mechanism, Journal of Bioactive and Compatible Polymers, Jul. 2002, pp. 1-10.
Pollard, C., et al., Type I IFN counteracts the induction of antigen-specific immune responses by lipid-based delivery of mRNA vaccines. Mol Ther. Jan. 2013; 21(1): 251-259.
Pulford, B., et al., Liposome-siRNA-peptide complexes cross the blood-brain barrier and significantly decrease PrP$^\wedge$C on neuronal cells and PrP$^\wedge$RES in infected cell cultures. PLoS ONE. 2010; 5(6): e11085.
Sahay, G. et al., "Efficiency of siRNA delivery by lipid nanoparticles is limited by endocytic recycling," Nat Biotechnol. Jul. 2013 ; 31(7): 653-658.
Saito, R., et al., Distribution of liposomes into brain and rat brain tumor models by convection-enhanced delivery monitored with magnetic resonance imaging. Cancer Res. Apr. 2004; 64: 2572-2579.
Sakuma, S. et al., Mucoadhesion of polystyrene nanoparticles having surface hydrophilic polymeric chains in the gastrointestinal tract. Int J Pharm. Jan. 25, 1999;177(2):161-72.
Schott, J.W., et al., Viral and non-viral approaches for transient delivery of mRNA and proteins. Current Gene Ther. 2011; 11 (5): 382-398.
Semple, S.C., et al., Efficient encapsulation of antisense oligonucleotides in lipid vesicles using ionizable aminolipids: formation of novel small multilamellar vesicle structures. Biochim Biophys Acta. Feb. 9, 2001; 1510(1-2): 152-166.
Shah et al., "Lipid Nanoparticles: Production, Characterization and Stability," Springer International Publishing, 2014, 23 pages.
Shea, R.G. et al., Synthesis, hybridization properties and antiviral activity of lipid-oligodeoxynucleotide conjugates. Nucleic Acids Res.Jul. 11, 1990;18(13):3777-83.
Strobel, I. et al., Human dendritic cells transfected with either RNA or DNA encoding influenza matrix protein M1 differ in their ability to stimulate cytotoxic T lymphocytes. Gene Ther. Dec. 2000; 7(23): 2028-2035.
Svinarchuk, F.P. et al., Inhibition of HIV proliferation in MT-4 cells by antisense oligonucleotide conjugated to lipophilic groups. Biochimie. 1993;75(1-2):49-54.
Tam et al., "Advances in Lipid Nanoparticles for siRNA Delivery," Pharmaceutics 2013, 5, 498-507; doi:10.3390/pharmaceutics5030498.
Tavernier, G., et al., mRNA as gene therapeutic: How to control protein expression. J. of Controlled Release. Mar. 2011; 150(3): 238-247.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015. 103. Epub Jun. 8, 2015.
Torchilin, Vladimir et al., Multifunctional and Stimuli-Sensitive Pharmaceutical Nanocarriers, Eur J. Pharm Biopharm, 2009, vol. 71, No. 3, pp. 431-444.
Tracy, M., "Progress in the Development of LNP Delivery for siRNA Advancing LNPs to the Clinic," International Liposome Research Days Meeting, Vancouver, Canada. Aug. 2010, pp. 1-52.
Treat, J. et al., in Liposomes in the Therapy of Infectious Disease and Cancer, Lopez-Berestein and Fidler (eds.), Liss, New York, 1989. 353-65.
Uzgun, S., et al., PEGylation improves nanoparticle formation and transfection efficiency of messenger RNA. Pharm Res. Sep. 2011; 28(9); 2223-2232.
Van Tendeloo, V.F. et al., Highly efficient gene delivery by mRNA electroporation in human hematopoietic cells: superiority to lipofection and passive pulsing of mRNA and to electroporation of plasmid cDNA for tumor antigen loading of dendritic cells. Blood. Jul. 1, 2001;98(1):49-56.
Wan et al., Lipid nanoparticle delivery systems for siRNA-based therapeutics. Drug Deliv Transl Res. Feb. 2014;4(1):74-83. doi:10. 1007/s13346-013-0161-z.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.

(56) References Cited

OTHER PUBLICATIONS

Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.

Yamamoto et al., Current prospects for mRNA gene delivery, European Journal of Pharmaceutics and Biopharmaceutics 71 (2009) 484-489.

Zhang et al., "A novel cationic cardiolipin analogue for gene delivery," Pharmazie, 2006, 61: 10-14).

Zhigaltsev, I.V., et al., Bottom-Up design and synthesis of limit size lipid nanoparticle systems with aqueous and triglyceride cores using millisecond microfluidic mixing. Langmuir. Feb. 21, 2012; 28(7): 3633-3640.

Zimmermann, E. et al., Electrolyte- and pH-stabilities of aqueous solid lipid nanoparticle (SLN™) dispersions in artificial gastrointestinal media. Eur J Pharm Biopharm. Sep. 2001;52(2):203-10.

Zohra, F.T., et al., Drastic effect of nanoapatite particles on liposome-mediated mRNA delivery to mammalian cells. Analytical Biochem. Oct. 2005; 345(1): 164-166.

Zohra, F.T., et al., Effective delivery with enhanced translational activity synergistically accelerates mRNA-based transfection. Biochem Biophys Res Comm. Jun. 2007; 358(1): 373-378.

* cited by examiner

CRYSTAL FORMS OF AMINO LIPIDS

RELATED APPLICATIONS

This application is a U.S. National Phase application, filed under U.S.C. § 371, of International Application No. PCT/US2018/022740, filed Mar. 15, 2018, which claims priority to, and the benefit of, U.S. Provisional Application No. 62/471,908, filed Mar. 15, 2017; the entire content of which is incorporated herein by reference.

TECHNICAL FIELD

This disclosure relates to solid crystalline forms of each of three compounds: (1) heptadecan-9-yl 8-((2-hydroxyethyl)amino)octanoate ("Compound 1"), (2) heptadecan-9-yl 8-((2-hydroxyethyl)(6-oxo-6-(undecyloxy)hexyl)amino)octanoate ("Compound 2"), and (3) heptadecan-9-yl 8-((2-hydroxyethyl)(8-(nonyloxy)-8-oxooctyl)amino)octanoate ("Compound 3"), and related compositions and methods. This disclosure also relates to solid crystalline forms of (6Z,9Z,28Z,31Z)-heptatriaconta-6,9,28,31-tetraen-19-yl 4-(dimethylamino)butanoate ("MC3"), and related compositions and methods.

BACKGROUND

The effective targeted delivery of biologically active substances such as small molecule drugs, proteins, and nucleic acids represents a continuing medical challenge. In particular, the delivery of nucleic acids to cells is made difficult by the relative instability and low cell permeability of such species. Thus, there exists a need to develop methods and compositions to facilitate the delivery of therapeutic and/or prophylactics such as nucleic acids to cells.

Lipid-containing nanoparticle compositions, liposomes, and lipoplexes have proven effective as transport vehicles into cells and/or intracellular compartments for biologically active substances such as small molecule drugs, proteins, and nucleic acids. Such compositions generally include one or more "cationic" and/or amino (ionizable) lipids, phospholipids including polyunsaturated lipids, structural lipids (e.g., sterols), and/or lipids containing polyethylene glycol (PEG lipids). Cationic and/or ionizable lipids include, for example, amine-containing lipids that can be readily protonated. Though a variety of such lipid-containing nanoparticle compositions have been demonstrated, improvements in safety, efficacy, and specificity are still lacking. In addition, the physical and chemical properties of lipid materials often present challenges relating to the practice of making and using lipid-containing nanoparticles for drug delivery.

SUMMARY

Long-chain amino lipids are usually viscous oils at room temperature. Solid forms of these lipids are desirable for e.g., improving handling, improving stability (such as storage stability) and/or control of physical/chemical properties, simplifying purification process, simplifying large-scale production process and/or increasing accuracy in measurements and characterization of lipids.

Accordingly, provided herein are novel solid forms (e.g., crystalline forms) of each of three compounds (1) heptadecan-9-yl 8-((2-hydroxyethyl)amino)octanoate ("Compound 1"), (2) heptadecan-9-yl 8-((2-hydroxyethyl)(6-oxo-6-(undecyloxy)hexyl)amino)octanoate ("Compound 2"), and (3) heptadecan-9-yl 8-((2-hydroxyethyl)(8-(nonyloxy)-8-oxooctyl)amino)octanoate ("Compound 3"), the structure of each of which is provided below:

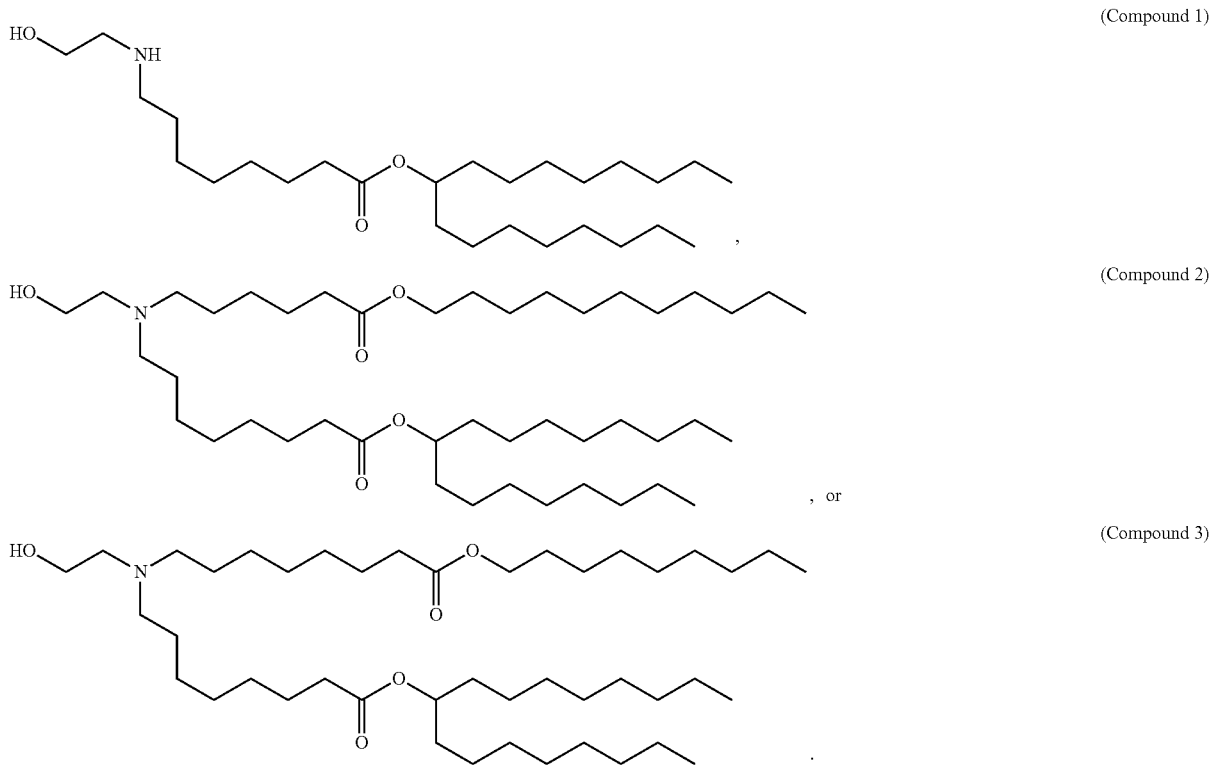

(Compound 1)

(Compound 2)

, or (Compound 3)

In another aspect, provided herein are novel solid forms (e.g., crystalline forms) of (6Z,9Z,28Z,31Z)-heptatriaconta-6,9,28,31-tetraen-19-yl 4-(dimethylamino)butanoate ("MC3"), the structure of which is provided below:

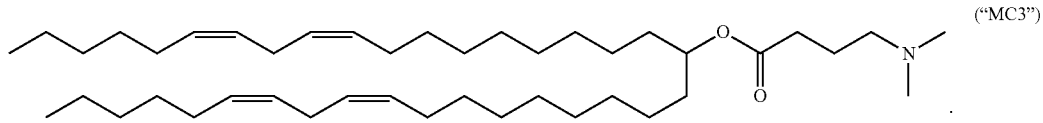
("MC3")

In one aspect, disclosed herein is salt or cocrystal of heptadecan-9-yl 8-((2-hydroxyethyl)amino)octanoate ("Compound 1"), heptadecan-9-yl 8-((2-hydroxyethyl)(6-oxo-6-(undecyloxy)hexyl)amino)octanoate ("Compound 2"), or heptadecan-9-yl 8-((2-hydroxyethyl)(8-(nonyloxy)-8-oxooctyl)amino)octanoate ("Compound 3"). In another aspect, the salt or cocrystal of Compound 1, 2, or 3 has a melting point of about 50° C. or greater (e.g., about 60° C., about 70° C. or greater). In another aspect, the salt or cocrystal of Compound 3 has a melting point of about 270° C. or greater (e.g., about 280° C., about 290° C. or greater). For example, the salt or cocrystal of Compound 1, 2, or 3 is formed between Compound 1, 2, or 3 and a coformer compound (e.g., an acid).

In one aspect, disclosed herein is a salt or cocrystal of (6Z,9Z,28Z,31Z)-heptatriaconta-6,9,28,31-tetraen-19-yl 4-(dimethylamino)butanoate ("MC3"). In another aspect, the salt or cocrystal of MC3 has a melting point of about 150° C. or greater (e.g., about 160° C., about 170° C., about 180° C. or greater, about 190° C. or greater). In another aspect, disclosed herein is a salt or cocrystal of (6Z,9Z,28Z, 31Z)-heptatriaconta-6,9,28,31-tetraen-19-yl 4-(dimethylamino)butanoate ("MC3"). In another aspect, the salt or cocrystal of MC3 has a melting point of about 50° C. or greater (e.g., about 60° C., about 70° C., about 80° C. or greater). For example, the salt or cocrystal of MC3 is formed between MC3 and a coformer compound (e.g., an acid).

In one aspect, this disclosure is directed to a salt or cocrystal of heptadecan-9-yl 8-((2-hydroxyethyl)amino)octanoate ("Compound 1") and a compound (e.g., a coformer compound) selected from the group consisting of 4-hydroxybenzoic acid, oxalic acid, trimellitic acid, orotic acid, trimesic acid, and sulfuric acid.

In another aspect, this disclosure is directed to a salt or cocrystal of heptadecan-9-yl 8-((2-hydroxyethyl)(6-oxo-6-(undecyloxy)hexyl)amino)octanoate ("Compound 2") and a compound (e.g., a coformer compound) selected from the group consisting of trimesic acid, (−)-2,3-dibenzoyl-L-tartaric acid, 4-acetamido benzoic acid, (+)-L-tartaric acid, and methanesulfonic acid.

In yet another aspect, this disclosure is directed to a salt or cocrystal of heptadecan-9-yl 8-((2-hydroxyethyl)(8-(nonyloxy)-8-oxooctyl)amino)octanoate ("Compound 3") and trimesic acid.

In one aspect, this disclosure is directed to a salt or cocrystal of (6Z,9Z,28Z,31Z)-heptatriaconta-6,9,28,31-tetraen-19-yl 4-(dimethylamino)butanoate ("MC3") and a compound selected from the group consisting of (+)-O,O-di-pivaloyl-D-tartaric acid (DPDT), (−)-O,O-di-pivaloyl-L-tartaric acid (DPLT), (+)-2,3-dibenzoyl-D-tartaric acid (DBDT), and trimesic acid. In one embodiment this disclosure is directed to a salt or cocrystal of (6Z,9Z,28Z,31Z)-heptatriaconta-6,9,28,31-tetraen-19-yl 4-(dimethylamino) butanoate ("MC3") and trimesic acid.

The salts or cocrystals disclosed herein may comprise Compound 1 (or Compound 2 or 3) and the coformer compound (e.g., an acid), within a ratio of from about 1:0.2 mol/mol (i.e., 5:1 mol/mol) to 1:5 mol/mol or from about 1:0.5 mol/mol (i.e., 2:1 mol/mol) to 1:2 mol/mol, or within the range of from 1:0.4 mol/mol (i.e., 2.5:1 mol/mol) to 1:1.1 mol/mol.

The salts or cocrystals disclosed herein may comprise (6Z,9Z,28Z,31Z)-heptatriaconta-6,9,28,31-tetraen-19-yl 4-(dimethylamino)butanoate ("MC3") and the coformer compound (e.g., an acid), within a ratio of from about 1:0.5 mol/mol (i.e., 2:1 mol/mol) to 1:2 mol/mol. For example the ratio is about 1:1.2 mol/mol, about 1:1.1 mol/mol, or about 1:1.5 mol/mol).

The salts or cocrystals disclosed herein may be anhydrous and/or essentially solvent-free form, or be in hydrate and/or solvate form. For example, 4-hydroxybenzoate of Compound 1 is anhydrous. For example, Compound 1 orotate may be anhydrous or in a hydrate or solvate form. For example, trimesate of MC3 may be anhydrous or in a hydrate or solvate form.

The salts or cocrystals disclosed herein may be non-hygroscopic. For example, the 4-hydroxybenzoate of Compound 1 is non-hygroscopic. For example, the trimesate of MC3 is non-hygroscopic.

It has been found that under suitable conditions some of the salts or cocrystals can be obtained in the form of different polymorphs. For example, 4-hydroxybenzoate of Compound 1 has at least two polymorphs, Polymorphs A and B. For example, orotate of Compound 1 has at least two polymorphs, Polymorphs A and B. For example, orotate of Compound 7 has at least two polymorphs, Polymorphs A and B. For example trimesate of Compound 3 has at least two polymorphs, Polymorphs A and B. For example, trimesate of MC3 has at least two polymorphs, Polymorphs A and B The polymorphs disclosed herein may be substantially pure, i.e., substantially free of impurities. Non-limiting examples of impurities include other polymorph forms, or residual organic and inorganic molecules such as related impurities (e.g., intermediates used to make the compounds), solvents, water or salts. As used herein "substantially pure" or "substantially free of impurities" means there is not a significant amount of impurities (e.g., other polymorph forms, or residual organic and inorganic molecules such as related impurities, solvents, water or salts) present in a sample of the salt, cocrystal, or polymorph. For example, a salt, cocrystal, or polymorph disclosed herein contains less than 10% weight by weight (wt/wt) total impurities, less than 5% wt/wt total impurities, less than 2% wt/wt total impurities, less than 1% wt/wt total impurities, less than 0.5% wt/wt total impurities, or not a detectable amount of impurities.

In one embodiment, Polymorph A of 4-hydroxybenzoate of Compound 1 is substantially free of impurities, meaning there is not a significant amount of impurities present in the sample of Polymorph A. In another embodiment, Polymorph A is a crystalline solid substantially free of Compound 1 (or any of its amorphous salt forms). In yet another embodiment, Polymorph A is a crystalline solid substantially free of other polymorphs of 4-hydroxybenzoate of Compound 1 and substantially free of amorphous Compound 1 (or any of its amorphous salt forms). For example, Polymorph A is a crystalline solid substantially free of Polymorph B of 4-hydroxybenzoate of Compound 1 and substantially free of amorphous Compound 1 (or any of its amorphous salt forms). The skilled artisan understands that a solid sample of Polymorph A may also include other polymorphs (e.g., Polymorph B), and/or amorphous Compound 1 (or any of its amorphous salt forms).

Polymorph A of 4-hydroxybenzoate of Compound 1 can be defined according to its X-ray powder diffraction pattern. Accordingly, in one embodiment, Polymorph A exhibits an X-ray powder diffraction pattern obtained using Cu Kα radiation, having two, three, or more characteristic peaks expressed in degrees 2-theta (+/−0.2) selected from the group consisting of 4.5, 6.8, 9.1, and 11.4. In one embodiment, Polymorph A exhibits an X-ray powder diffraction pattern obtained using Cu Kα radiation, having peaks with 2-theta values substantially in accordance with FIG. 1. In another embodiment, Polymorph A exhibits an X-ray powder diffraction pattern obtained using Cu Kα radiation, having peaks with 2-theta values substantially in accordance with Table I.

Polymorph A of 4-hydroxybenzoate of Compound 1 can also be defined according to its differential scanning calorimetry thermogram. In one embodiment, the polymorph exhibits a differential scanning calorimetry thermogram showing a primary endotherm expressed in units of ° C. at a temperature of 103+/−2° C. and a second primary endotherm expressed in units of ° C. at a temperature of 68+/−2° C. In another embodiment, Polymorph A exhibits a differential scanning calorimetry thermogram substantially in accordance with the lower curve shown in FIG. 3.

In one embodiment, Polymorph B of Compound 1 orotate is substantially free of impurities (e.g., phase or form impurities), meaning there is not a significant amount of impurities present in the sample of Polymorph B. In another embodiment, Polymorph B is a crystalline solid substantially free of amorphous Compound 1 (or any of its amorphous salt forms). In yet another embodiment, Polymorph B is a crystalline solid substantially free of other polymorphs of Compound 1 orotate and substantially free of amorphous Compound 1 (or any of its amorphous salt forms). For example, Polymorph B is a crystalline solid substantially free of Polymorph A of Compound 1 orotate and substantially free of amorphous Compound 1 (or any of its amorphous salt forms). The skilled artisan understands that a solid sample of Polymorph B of Compound 1 orotate may also include other polymorphs (e.g., Polymorph A), and/or amorphous Compound 1 (or any of its amorphous salt forms).

Polymorph B of Compound 1 orotate can be defined according to its X-ray powder diffraction pattern. Accordingly, in one embodiment, Polymorph B exhibits an X-ray powder diffraction pattern obtained using Cu Kα radiation, having two, three, four, or more characteristic peaks expressed in degrees 2-theta (+/−0.2) selected from the group consisting of 5.1, 7.5, 10.1, 12.7, 15.2, and 17.8. In one embodiment, Polymorph B exhibits an X-ray powder diffraction pattern obtained using Cu Kα radiation, having peaks with 2-theta values substantially in accordance with FIG. 18, upper profile. In another embodiment, Polymorph B exhibits an X-ray powder diffraction pattern obtained using Cu Kα radiation, having peaks with 2-theta values substantially in accordance with Table III.

In one embodiment, Polymorph B of trimesate of Compound 3 is substantially free of impurities, meaning there is not a significant amount of impurities present in the sample of Polymorph B. In another embodiment, Polymorph B is a crystalline solid substantially free of Compound 3 (or any of its amorphous salt forms). In yet another embodiment, Polymorph B is a crystalline solid substantially free of other polymorphs of trimesate of Compound 3 and substantially free of amorphous trimesate of Compound 3 (or any of its amorphous salt forms). For example Polymorph B is a crystalline solid substantially free of Polymorph A of trimesate of Compound 3 and substantially free of amorphous trimesate of Compound 3 (or any of its amorphous salt forms). The skilled artisan understands that a solid sample of Polymorph B may also include other polymorphs (e.g., Polymorph A) and/or amorphous Compound 3 (or any of its amorphous salt forms).

Polymorph B of Compound 3 trimesate can be defined according to its X-ray powder diffraction pattern. Accordingly, Polymorph B of Compound 3 trimesate exhibits an X-ray powder diffraction pattern obtained using Cu Kα radiation, having two, three, four or more characteristic peaks expressed in degrees 2-theta (+/−0.4) at 6.2, 10.8, 16.5, and 26.7. In one embodiment, Polymorph B exhibits an X-ray powder diffraction pattern obtained using Cu Kα radiation, having peaks with 2-theta values substantially in accordance with FIG. 48. In another embodiment, Polymorph B exhibits an X-ray powder diffraction pattern obtained using Cu Kα radiation, having peaks with 2-theta values substantially in accordance with Table XII.

In other embodiments, Polymorph B of trimesate of Compound 3 is identifiable on the basis of a characteristic peak observed in a differential scanning calorimetry thermogram. In one embodiment, the polymorph exhibits a differential scanning calorimetry thermogram showing a characteristic melting endotherm peak expressed in units of ° C. with an onset temperature of about 305+/−2° C. In another embodiment, the polymorph exhibits a differential scanning calorimetry thermogram showing a second primary endotherm expressed in units of ° C. at a temperature of 240+/−2° C. In another embodiment, the polymorph exhibits a differential scanning calorimetry thermogram substantially in accordance with FIG. 49.

In one embodiment, Polymorph A of trimesate of MC3 is substantially free of impurities, meaning there is not a significant amount of impurities present in the sample of Polymorph A. In another embodiment, Polymorph A is a crystalline solid substantially free of MC3 (or any of its amorphous salt forms). In yet another embodiment, Polymorph A is a crystalline solid substantially free of other polymorphs of trimesate of MC3 and substantially free of amorphous MC3 (or any of its amorphous salt forms). For example, Polymorph A is a crystalline solid substantially free of Polymorph B of trimesate of MC3 and substantially free of amorphous MC3 (or any of its amorphous salt forms). The skilled artisan understands that a solid sample of Polymorph A may also include other polymorphs (e.g., Polymorph B), and/or amorphous MC3 (or any of its amorphous salt forms).

Polymorph A of MC3 trimesate can be defined according to its X-ray powder diffraction pattern. Accordingly, Polymorph A of MC3 trimesate exhibits an X-ray powder diffraction pattern obtained using Cu Kα radiation, having two, three, four or more characteristic peaks expressed in degrees 2-theta (+/−0.4) at 5.2, 7.8, 10.4, 18.3, 20.9, 23.6, or 26.2. In one embodiment, Polymorph A exhibits an X-ray powder diffraction pattern obtained using Cu Kα radiation, having peaks with 2-theta values substantially in accordance with FIG. 52. In one embodiment, Polymorph A exhibits an X-ray powder diffraction pattern obtained using Cu Kα radiation, having peaks with 2-theta values substantially in accordance with Table XIII.

Polymorph A of MC3 trimesate can also be defined according to its differential scanning calorimetry thermogram. In one embodiment, the polymorph exhibits a differential scanning calorimetry thermogram showing a primary endotherm expressed in units of ° C. at a temperature of 184+/−2° C. In one embodiment, the polymorph exhibits a differential scanning calorimetry thermogram showing a primary endotherm expressed in units of ° C. at a temperature of 186+/−2° C. and a second primary endotherm expressed in units of ° C. at a temperature of 90+/−2° C. In yet another embodiment, the polymorph exhibits a differential scanning calorimetry thermogram substantially in accordance with FIG. 53 or FIG. 54.

Polymorph B of MC3 trimesate can be defined according to its X-ray powder diffraction pattern. Accordingly, Polymorph B of MC3 trimesate exhibits an X-ray powder diffraction pattern obtained using Cu Kα radiation, having two, three, four or more characteristic peaks expressed in degrees 2-theta (+/−0.4) at 4.8, 5.4, 7.2, 9.7, 12.1, 14.5, 17.0, 19.4, 21.9, 24.3, 26.8, 29.3, or 31.8. In one embodiment, Polymorph B exhibits an X-ray powder diffraction pattern obtained using Cu Kα radiation, having peaks with 2-theta values substantially in accordance with FIG. 59. In another embodiment, Polymorph B exhibits an X-ray powder diffraction pattern obtained using Cu Kα radiation, having peaks with 2-theta values substantially in accordance with Table XIV.

Polymorph B of MC3 trimesate can also be defined according to its differential scanning calorimetry thermogram. In one embodiment, the polymorph exhibits a differential scanning calorimetry thermogram showing a primary endotherm expressed in units of ° C. at a temperature of 187+/−2° C. In another embodiment, the polymorph exhibits a differential scanning calorimetry thermogram substantially in accordance with FIG. 60.

Another aspect of the disclosure relates to the preparation of the salt or cocrystal of heptadecan-9-yl 8-((2-hydroxyethyl)amino)octanoate ("Compound 1") and a compound selected from the group consisting of 4-hydroxybenzoic acid, oxalic acid, trimellitic acid, orotic acid, trimesic acid, and sulfuric acid.

Also provided herein is a method for preparing the salt or cocrystal of heptadecan-9-yl 8-((2-hydroxyethyl)(6-oxo-6-(undecyloxy)hexyl)amino)octanoate ("Compound 2") and a compound selected from the group consisting of trimesic acid, (−)-2,3-dibenzoyl-L-tartaric acid, 4-acetamido benzoic acid, (+)-L-tartaric acid, and methanesulfonic acid.

This disclosure also provides a method of preparing the salt or cocrystal of heptadecan-9-yl 8-((2-hydroxyethyl)(8-(nonyloxy)-8-oxooctyl)amino)octanoate ("Compound 3") and trimesic acid.

This disclosure also provides a method of preparing the salt or cocrystal of (6Z,9Z,28Z,31Z)-heptatriaconta-6,9,28,31-tetraen-19-yl 4-(dimethylamino)butanoate ("MC3") ("MC3") and trimesic acid.

In still another aspect, provided herein is a process of synthesizing Compound 2, Compound 3, or an analog thereof by reacting a salt or cocrystal of Compound 1 disclosed herein with a suitable electrophile, such as an ester substituted with a halogen (e.g., Br or I).

Also provided herein is a process of purifying Compound 1, 2, or 3 by forming a salt or cocrystal thereof disclosed herein to separate the salt or cocrystal thereof from the impurities. The method may further comprise neutralizing the salt or cocrystal to convert to Compound 1, 2, or 3 (i.e., a free base).

In one embodiment, the process of the present disclosure is advantageous as compared to other processes in that the process of the disclosure produces Compound 1, 2, or 3 or a salt or cocrystal thereof at a large scale and/or at a high purity, e.g., such that cumbersome purification (e.g., column chromatography, extraction, phase separation, distillation and solvent evaporation) is not needed. In one embodiment, the process of the present disclosure is able to process at least 100 g, 200 g, 500 g, or more (e.g., 1 kg, 2 kg, 5 kg, 10 kg, 20 kg, 50 kg, 100 kg, 200 kg, 500 kg, or 1000 kg or more) Compound 1, 2, or 3 or a salt or cocrystal thereof. In one embodiment, the process of the present disclosure is able to produce Compound 1, 2, or 3 or a salt or cocrystal thereof at least at a purity of at least 75%, 80%, 85%, 90%, 95%, 96%, 97%, 98%, 99%, or 99.5%, or higher. In one embodiment, the process of the present disclosure is able to produce Compound 1, 2, or 3 or a salt or cocrystal thereof with little or no impurity. In one embodiment, the impurity produced in the process of the present disclosure, even if produced, is easy to be separated from Compound 1, 2, or 3 or a salt or cocrystal thereof, without cumbersome purification (e.g., column chromatography, extraction, phase separation, distillation and solvent evaporation).

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Other features and advantages of the invention will be apparent from the following drawings, detailed description and claims.

DETAILED DESCRIPTION

Figure 1:
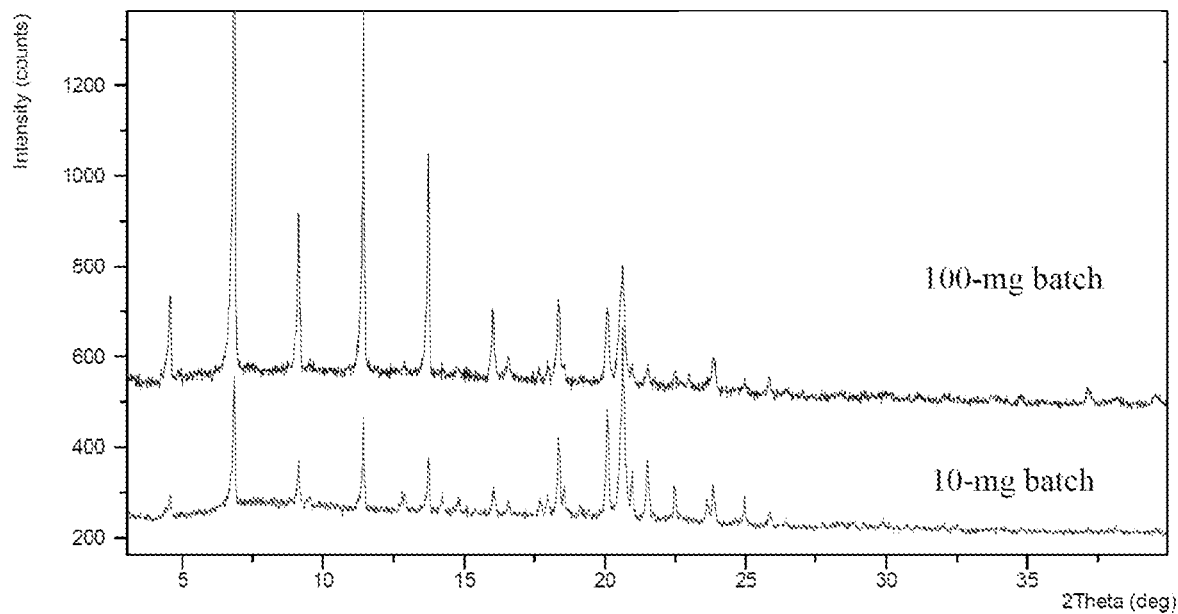
FIG. 1 depicts a representative X-ray powder diffraction (XRPD) pattern overlay of heptadecan-9-yl 8-((2-hydroxyethyl)amino)octanoate 4-hydroxybenzoate Polymorph A batches, i.e., 100 mg and 10 mg batches or batches Nos. 1 and 2.

The solid form (e.g., crystal state) of a compound may be important when the compound is used for pharmaceutical purposes. Compared with an amorphous solid or viscous oil, the physical properties of a crystalline compound are generally enhanced. These properties change from one solid form to another, which may impact its suitability for pharmaceutical use. In addition, different solid forms of a crystalline compound may incorporate different types and/or different amounts of impurities. Different solid forms of a compound may also have different chemical stability upon exposure to heat, light and/or moisture (e.g., atmospheric moisture) over a period of time, or different rates of dissolution. Long-chain amino lipids are usually oils at room temperature. Solid forms of these lipids are desirable for e.g., improving handling, improving stability (such as storage stability), simplifying purification process, simplifying large-scale production process and/or increasing accuracy in measurements and characterization of lipids.

Provided herein are novel solid forms (e.g., crystalline forms) of each of Compound 1, Compound 2, and Compound 3, the structure of each of which is provided below:

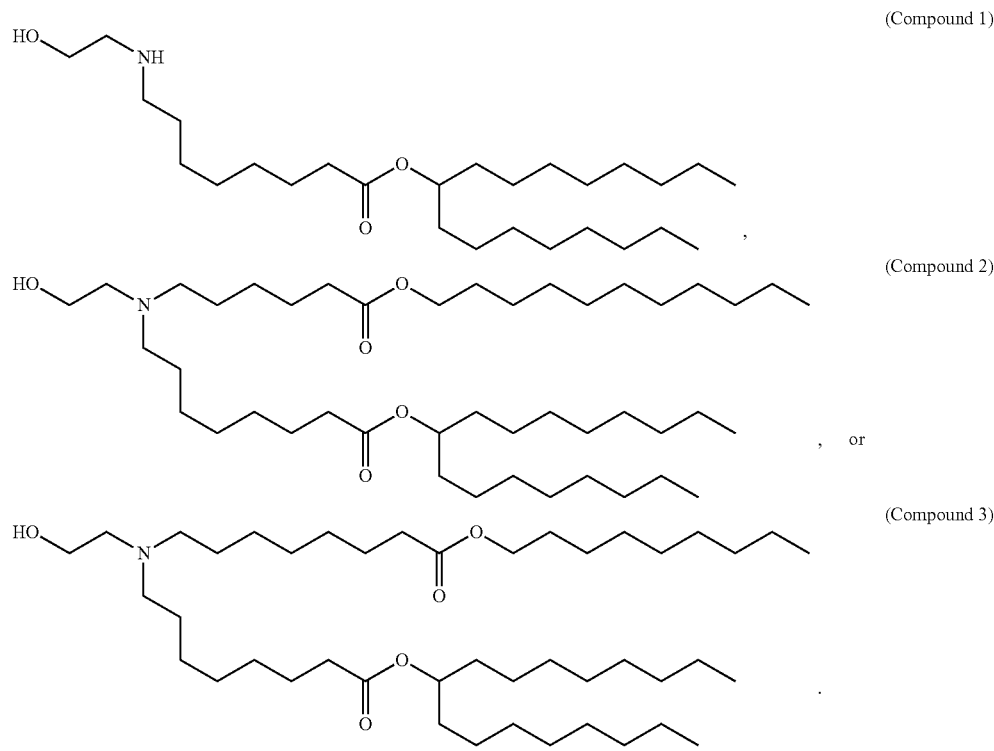

(Compound 1)

(Compound 2)

, or (Compound 3)

In another aspect, provided herein are novel solid forms (e.g., crystalline forms) of (6Z,9Z,28Z,31Z)-heptatriaconta- 6,9,28,31-tetraen-19-yl 4-(dimethylamino)butanoate ("MC3"), the structure of which is provided below:

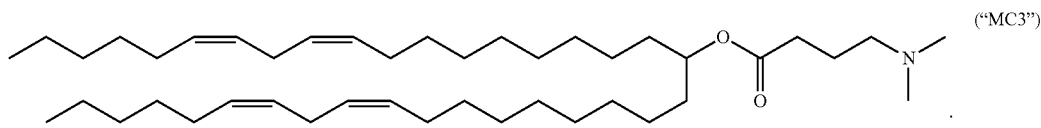 [SMILES: CCCCC/C=C\C/C=C\CCCCCCCCC(CCCCCCCC/C=C\C/C=C\CCCCC)OC(=O)CCCN(C)C]

In one aspect, disclosed herein is salt or cocrystal of Compound 1, 2, or 3, which has a melting point of about 50° C. or greater (e.g., about 60° C., about 70° C. or greater). For example, the salt or cocrystal of Compound 1, 2, or 3 is formed between Compound 1, 2, or 3 and a coformer compound (e.g., an acid). In another aspect, the salt or cocrystal of Compound 3 has a melting point of about 270° C. or greater (e.g., about 280° C., about 290° C. or greater).

As used herein, "Compound 1" refers to heptadecan-9-yl 8-((2-hydroxyethyl)amino)octanoate; "Compound 2" refers to heptadecan-9-yl 8-((2-hydroxyethyl)(6-oxo-6-(undecyloxy)hexyl)amino)octanoate; and "Compound 3" refers to heptadecan-9-yl 8-((2-hydroxyethyl)(8-(nonyloxy)-8-oxooctyl)amino)octanoate. Compound 1 can be used as a starting material for the synthesis of Compound 2 or 3.

As used herein, "MC 3" refers to (6Z,9Z,28Z,31Z)-heptatriaconta-6,9,28,31-tetraen-19-yl 4-(dimethylamino) butanoate.

In one aspect, this disclosure is directed to a salt or cocrystal of Compound 1 and a compound selected from the group consisting of 4-hydroxybenzoic acid, oxalic acid, trimellitic acid, orotic acid, trimesic acid, and sulfuric acid. For example, the compound is 4-hydroxybenzoic acid. For example, the compound is oxalic acid.

Also described herein are polymorphic forms of a salt or cocrystal of Compound 1, e.g., Polymorphs A and B of 4-hydroxybenzoate of Compound 1, or Polymorphs A and B of orotate of Compound 1.

In one aspect, this disclosure is directed to a salt or cocrystal of (6Z,9Z,28Z,31Z)-heptatriaconta-6,9,28,31-tetraen-19-yl 4-(dimethylamino)butanoate ("MC3"). In another aspect, the salt or cocrystal of MC3 has a melting point of about 150° C. or greater (e.g., about 160° C., about 170° C., about 180° C. or greater, about 190° C. or greater). In another aspect, disclosed herein is a salt or cocrystal of (6Z,9Z,28Z,31Z)-heptatriaconta-6,9,28,31-tetraen-19-yl 4-(dimethylamino)butanoate ("MC3"). In another aspect, the salt or cocrystal of MC3 has a melting point of about 50° C. or greater (e.g., about 60° C., about 70° C., about 80° C. or greater). For example, the salt or cocrystal of MC3 is formed between MC3 and a coformer compound (e.g., an acid).

The ability of a substance to exist in more than one crystal form is defined as polymorphism; the different crystal forms of a particular substance are referred to as "polymorphs" of one another. In general, polymorphism is affected by the ability of a molecule of a substance (or its salt, cocrystal, or hydrate) to change its conformation or to form different intermolecular or intra-molecular interactions, (e.g., different hydrogen bond configurations), which is reflected in different atomic arrangements in the crystal lattices of different polymorphs. In contrast, the overall external form of a substance is known as "morphology," which refers to the external shape of the crystal and the planes present, without reference to the internal structure. A particular crystalline polymorph can display different morphology based on different conditions, such as, for example, growth rate, stirring, and the presence of impurities.

The different polymorphs of a substance may possess different energies of the crystal lattice and, thus, in solid state they can show different physical properties such as form, density, melting point, color, stability, solubility, dissolution rate, etc., which can, in turn, effect the stability, dissolution rate and/or bioavailability of a given polymorph and its suitability for use as a pharmaceutical and in pharmaceutical compositions.

Polymorph A of 4-hydroxybenzoate of Compound 1 has a number of advantageous physical properties over its free base form, as well as other salts of the free base. In particular, Polymorph A of 4-hydroxybenzoate of Compound 1 has low hygroscopicity compared to other salt forms of Compound 1. More particularly, Polymorph A of 4-hydroxybenzoate of Compound 1 has low hygroscopicity compared to Polymorph A of Compound 1 trimellitate and Polymorph B of Compound 1 orotate (see, e.g., Table 1-2). Crystal forms that are highly hygroscopic may also be unstable, as the compound's dissolution rate (and other physico-chemical properties) may change as it is stored in settings with varying humidity. Also, hygroscopicity can impact large-scale handling and manufacturing of a compound, as it can be difficult to determine the true weight of a hygroscopic agent when using it for reactions or when preparing a pharmaceutical composition comprising that agent. For example, in large scale medicinal formulating preparations, highly hygroscopic compounds can result in batch manufacturing inconsistency creating clinical and/or prescribing difficulties. For example, when Compound 1 is used as a starting material for the synthesis of Compound 2 or 3, Polymorph A of 4-hydroxybenzoate of Compound 1 has a low hygoscopicity compared to other salt forms of Compound 1, and as such, it may be stored over appreciable periods or conditions (e.g., relative humidity conditions), and not suffer from weight changes that would be detrimental for consistent production of Compound 2 or 3.

In certain embodiments, Polymorph A of 4-hydroxybenzoate of Compound 1 is identifiable on the basis of characteristic peaks in an X-ray powder diffraction analysis. X-ray powder diffraction pattern, also referred to as XRPD pattern, is a scientific technique involving the scattering of x-rays by crystal atoms, producing a diffraction pattern that yields information about the structure of the crystal. In certain embodiments, Polymorph A of 4-hydroxybenzoate of Compound 1 exhibits an X-ray powder diffraction (XRPD) pattern obtained using Cu Kα radiation, having from two (2) to seven (7) characteristic peaks expressed in degrees 2-theta at 4.5, 6.8, 9.1, 11.4, 13.7, 18.3, 20.1, and 20.6.

The skilled artisan recognizes that some variation is associated with 2-theta measurements in XRPD. Typically, 2-theta values may vary from ±0.1 to ±0.2. Such slight variation can be caused, for example, by sample preparation, instrument configurations and other experimental factors. The skilled artisan appreciates that such variation in values are greatest with low 2-theta values, and least with high 2-theta values. The skilled artisan recognizes that different instruments may provide substantially the same XRPD pattern, even though the 2-theta values vary slightly. Moreover, the skilled artisan appreciates that the same instrument may provide substantially the same XRPD pattern for the same or different samples even though the XRPD of the respectively collected XRPD patterns vary slightly in the 2-theta values.

The skilled artisan also appreciates that XRPD patterns of the same sample (taken on the same or different instruments) may exhibit variations in peak intensity at the different 2-theta values. The skilled artisan also appreciates that XRPD patterns of different samples of the same polymorph (taken on the same or different instruments) may also exhibit variations in peak intensity at the different 2-theta values. XRPD patterns can be substantially the same pattern even though they have corresponding 2-theta signals that vary in their peak intensities.

In one embodiment, Polymorph A of 4-hydroxybenzoate of Compound 1 exhibits an X-ray powder diffraction pattern obtained using Cu Kα radiation, having two or more characteristic peaks expressed in degrees 2-theta (+/−0.2) selected from the group consisting of 4.5, 6.8, 9.1, and 11.4. In another embodiment, Polymorph A of 4-hydroxybenzoate of Compound 1 exhibits an X-ray powder diffraction pattern obtained using Cu Kα radiation, having three or more characteristic peaks expressed in degrees 2-theta (+/−0.2) selected from the group consisting of 4.5, 6.8, 9.1, 11.4, and 13.7. In another embodiment, Polymorph A of 4-hydroxybenzoate of Compound 1 exhibits an X-ray powder diffraction pattern obtained using Cu Kα radiation, having four or more characteristic peaks expressed in degrees 2-theta (+/−0.2) selected from the group consisting of 4.5, 6.8, 9.1, 11.4, and 13.7. In another embodiment, Polymorph A of 4-hydroxybenzoate of Compound 1 exhibits an X-ray powder diffraction pattern obtained using Cu Kα radiation, having characteristic peaks expressed in degrees 2-theta (+/−0.2) at 4.5, 6.8, 9.1, 11.4, 13.7, 18.3, 20.1, and 20.6. In one embodiment, Polymorph A of 4-hydroxybenzoate of Compound 1 exhibits an X-ray powder diffraction pattern obtained using Cu Kα radiation, having two, three, four, or more characteristic peaks expressed in degrees 2-theta (+/−0.2) selected from the group consisting of 4.5, 6.8, 9.1, 11.4, and 13.7.

In a particular embodiment, Polymorph A of 4-hydroxybenzoate of Compound 1 exhibits an X-ray powder diffraction pattern obtained using Cu Kα radiation, having at least eight characteristic peaks expressed in degrees 2-theta (+/−0.2), selected from the group consisting of 4.5, 6.8, 9.1, 11.4, 13.7, 16.0, 18.3, 20.1, and 20.6. In another particular embodiment, Polymorph A of 4-hydroxybenzoate of Compound 1 exhibits an X-ray powder diffraction pattern obtained using Cu Kα radiation, having at least nine characteristic peaks expressed in degrees 2-theta (+/−0.2), selected from the group consisting of 4.5, 6.8, 9.1, 11.4, 13.7, 16.0, 16.6, 18.3, 20.1, and 20.6. In a further embodiment, Polymorph A of 4-hydroxybenzoate of Compound 1 exhibits an X-ray powder diffraction pattern obtained using Cu Kα radiation, having at least ten characteristic peaks expressed in degrees 2-theta (+/−0.2), selected from the group consisting of 4.5, 6.8, 9.1, 11.4, 13.7, 16.0, 16.6, 18.3, 20.1, 20.6, and 21.5. In one embodiment, Polymorph A exhibits an X-ray powder diffraction pattern obtained using Cu Kα radiation, having peaks with 2-theta values substantially in accordance with FIG. 1. In another embodiment, Polymorph A exhibits an X-ray powder diffraction pattern obtained using Cu Kα radiation, having peaks with 2-theta values substantially in accordance with Table I below.

TABLE I

| Peak | Position [°2Th.] |
|---|---|
| 1. | 4.5 |
| 2. | 6.8 |
| 3. | 9.1 |
| 4. | 11.4 |
| 5. | 13.7 |
| 6. | 16.0 |
| 7. | 16.6 |
| 8. | 18.3 |
| 9. | 20.1 |
| 10. | 20.6 |
| 11. | 21.5 |
| 12. | 23.8 |
| 13. | 24.9 |
| 14. | 25.8 |

In other embodiments, Polymorph A of 4-hydroxybenzoate of Compound 1 is identifiable on the basis of a characteristic peak observed in a differential scanning calorimetry thermogram. Differential scanning calorimetry, or DSC, is a thermoanalytical technique in which the difference in the amount of heat required to increase the temperature of a sample and reference is measured as a function of temperature. In one embodiment, Polymorph A of 4-hydroxybenzoate of Compound 1 exhibits a differential scanning calorimetry thermogram showing a characteristic primary endotherm peak expressed in units of ° C. with an onset temperature of about 103+1-2° C. In another embodiment, Polymorph A of 4-hydroxybenzoate of Compound 1 exhibits a differential scanning calorimetry thermogram showing a characteristic second primary endotherm expressed in units of ° C. with an onset temperature of about 68+/−2° C. In another embodiment, Polymorph A of 4-hydroxybenzoate of Compound 1 exhibits a differential scanning calorimetry thermogram substantially in accordance with the lower curve shown in FIG. 3.

In another embodiment, provided herein is Polymorph A of 4-hydroxybenzoate of Compound 1, wherein the solid form undergoes a weight increase of less than 1.5% (e.g., less than 1%, or less than 0.6%) upon increasing relative humidity from 5.0% to 95.0% at e.g., 25° C. In another embodiment, Polymorph A of 4-hydroxybenzoate of Compound 1 is characterized as having a dynamic vapor sorption profile that is substantially in accordance with FIG. 8.

In one embodiment, Polymorph A of 4-hydroxybenzoate of Compound 1 is substantially free of impurities, meaning there is not a significant amount of impurities present in the sample of Polymorph A. In another embodiment, Polymorph A is a crystalline solid substantially free of amorphous Compound 1 (or any of its amorphous salt forms). In yet another embodiment, Polymorph A is a crystalline solid substantially free of other polymorphs of 4-hydroxybenzoate of Compound 1 and substantially free of amorphous Compound 1 (or any of its amorphous salt forms). For example, Polymorph A is a crystalline solid substantially free of Polymorph B of 4-hydroxybenzoate of Compound 1 and substantially free of amorphous Compound 1 (or any of its amorphous salt forms). The skilled artisan understands that a solid sample of Polymorph A may also include other polymorphs (e.g., Polymorph A), and/or amorphous Compound 1 (or any of its amorphous salt forms)

As used herein, the term "substantially free of amorphous Compound 1" means that the compound contains no significant amount of amorphous Compound 1 (or any of its amorphous salt forms). In another embodiment, a sample of a salt or cocrystal of Compound 1 comprises Polymorph A of 4-hydroxybenzoate of Compound 1 substantially free of other polymorphs (e.g., Polymorph B of 4-hydroxybenzoate of Compound 1). As used herein, the term "substantially free of other polymorphs" means that a sample of crystalline Compound 1 4-hydroxybenzoate contains no significant amount of other polymorphs (e.g., Polymorph B). In certain embodiments, at least about 90% by weight of a sample is Polymorph A, with only 10% being other polymorphs (e.g., Polymorph B) and/or amorphous Compound 1 (or any of its amorphous salt forms). In certain embodiments, at least about 95% by weight of a sample is Polymorph A, with only 5% being other polymorphs (e.g., Polymorph B) and/or amorphous Compound 1 (or any of its amorphous salt forms). In still other embodiments, at least about 98% by weight of a sample is Polymorph A, with only 2% by weight being other polymorphs (e.g., Polymorph B) and/or amorphous Compound 1 (or any of its amorphous salt forms). In still other embodiments, at least about 99% by weight of a sample is Polymorph A, with only 1% by weight being other polymorphs (e.g., Polymorph B) and/or amorphous Compound 1 (or any of its amorphous salt forms). In still other embodiments, at least about 99.5% by weight of a sample is Polymorph A, with only 0.5% by weight being other polymorphs (e.g., Polymorph B) and/or amorphous Compound 1 (or any of its amorphous salt forms). In still other embodiments, at least about 99.9% by weight of a sample is Polymorph A, with only 0.1% by weight being other polymorphs (e.g., Polymorph B) and/or amorphous Compound 1 (or any of its amorphous salt forms).

In certain embodiments, a sample of a salt or cocrystal of Compound 1 (e.g., Compound 1 oxalate or 4-hydroxybenzoate) may contain impurities. Non-limiting examples of impurities include other polymorph forms, or residual organic and inorganic molecules such as related impurities (e.g., intermediates used to make Compound 1 or by-products, e.g., heptadecan-9-yl 8-bromooctanoate and di(heptadecan-9-yl) 8,8'-((2-hydroxyethyl)azanediyl)dioctanoate), solvents, water or salts. In one embodiment, a sample of a salt or cocrystal of Compound 1, e.g., oxalate or 4-hydroxybenzoate Polymorph A is substantially free from impurities, meaning that no significant amount of impurities are present. In another embodiment, a sample of the salt or cocrystal of Compound 1 contains less than 10% weight by weight (wt/wt) total impurities. In another embodiment, a sample of the salt or cocrystal of Compound 1 contains less than 5% wt/wt total impurities. In another embodiment, a sample of the salt or cocrystal of Compound 1 contains less than 2% wt/wt total impurities. In another embodiment, a sample of the salt or cocrystal of Compound 1 contains less than 1% wt/wt total impurities. In yet another embodiment, a sample of the salt or cocrystal of Compound 1 contains less than 0.1% wt/wt total impurities. In yet another embodiment, a sample of the salt or cocrystal of Compound 1 does not contain a detectable amount of impurities.

Also disclosed herein are Polymorphs A and B of Compound 1 orotate. In a particular embodiment, Polymorph A of Compound 1 orotate exhibits an X-ray powder diffraction pattern obtained using Cu Kα radiation, having two, three, four, or more characteristic peaks expressed in degrees 2-theta (+/−0.2) selected from the group consisting of 5.3, 10.7, 13.3, 16.1, and 18.7. In one embodiment, Polymorph A exhibits an X-ray powder diffraction pattern obtained using Cu Kα radiation, having peaks with 2-theta values substantially in accordance with FIG. 18, lower profile. In another embodiment, Polymorph A exhibits an X-ray powder diffraction pattern obtained using Cu Kα radiation, having peaks with 2-theta values substantially in accordance with Table II below.

TABLE II

| Peak | Position [°2Th.] |
|---|---|
| 1. | 5.3 |
| 2. | 10.7 |
| 3. | 13.3 |
| 4. | 16.1 |
| 5. | 18.7 |
| 6. | 24.3 |
| 7. | 26.9 |

Polymorph B of Compound 1 orotate can be defined according to its X-ray powder diffraction pattern. Accordingly, in one embodiment, Polymorph B exhibits an X-ray powder diffraction pattern obtained using Cu Kα radiation, having two, three, four, or more characteristic peaks expressed in degrees 2-theta (+/−0.2) selected from the group consisting of 5.1, 7.5, 10.1, 12.7, 15.2, and 17.8. In one embodiment, Polymorph B exhibits an X-ray powder diffraction pattern obtained using Cu Kα radiation, having peaks with 2-theta values substantially in accordance with FIG. 18, upper profile. In another embodiment, Polymorph B exhibits an X-ray powder diffraction pattern obtained using Cu Kα radiation, having peaks with 2-theta values substantially in accordance with Table III.

TABLE III

| Peak | Position [°2Th.] |
|---|---|
| 1. | 5.1 |
| 2. | 7.5 |
| 3. | 10.1 |
| 4. | 12.7 |
| 5. | 15.2 |
| 6. | 17.8 |
| 7. | 20.2 |
| 8. | 25.5 |
| 9. | 28.2 |

In yet another embodiment, this disclosure provides Polymorph A of Compound 1 trimesate. In a particular embodiment, Polymorph A of Compound 1 trimesate exhibits an X-ray powder diffraction pattern obtained using Cu Kα radiation, having two, three, four, or more characteristic peaks expressed in degrees 2-theta (+1-0.2) selected from the group consisting of 3.3, 5.3, 6.7, 7.9, 10.5, 18.5, 21.3, 23.9, and 26.5. In one embodiment, Polymorph A exhibits an X-ray powder diffraction pattern obtained using Cu Kα radiation, having peaks with 2-theta values substantially in accordance with FIG. 32. In another embodiment, Polymorph A exhibits an X-ray powder diffraction pattern obtained using Cu Kα radiation, having peaks with 2-theta values substantially in accordance with Table IV below.

TABLE IV

| Peak | Position [°2Th.] |
|---|---|
| 1. | 3.3 |
| 2. | 5.3 |
| 3. | 6.7 |
| 4. | 7.9 |
| 5. | 10.5 |
| 6. | 13.6 |
| 7. | 18.5 |

TABLE IV-continued

| Peak | Position [°2Th.] |
|---|---|
| 8. | 21.3 |
| 9. | 23.9 |
| 10. | 26.5 |
| 11. | 29.1 |

This disclosure also provides Polymorph A of Compound 1 trimellitate. In a particular embodiment, Polymorph A of Compound 1 trimellitate exhibits an X-ray powder diffraction pattern obtained using Cu Kα radiation, having two, three, four, or more characteristic peaks expressed in degrees 2-theta (+/−0.2) selected from the group consisting of 4.6, 6.8, 9.2, 11.5, 23.1, and 25.4. In one embodiment, Polymorph A exhibits an X-ray powder diffraction pattern obtained using Cu Kα radiation, having peaks with 2-theta values substantially in accordance with FIG. 11. In another embodiment, Polymorph A exhibits an X-ray powder diffraction pattern obtained using Cu Kα radiation, having peaks with 2-theta values substantially in accordance with Table V below.

TABLE V

| Peak | Position [°2Th.] |
|---|---|
| 1. | 4.6 |
| 2. | 6.8 |
| 3. | 9.2 |
| 4. | 11.5 |
| 5. | 23.1 |
| 6. | 25.4 |
| 7. | 27.7 |

Also provided herein is Polymorph A of Compound 1 sulfate. In a particular embodiment, Polymorph A of Compound 1 sulfate exhibits an X-ray powder diffraction pattern obtained using Cu Kα radiation, having two, three, four, or more characteristic peaks expressed in degrees 2-theta (+/−0.2) selected from the group consisting of 4.0, 11.8, 21.4, 21.8, and 22.8. In one embodiment, Polymorph A exhibits an X-ray powder diffraction pattern obtained using Cu Kα radiation, having peaks with 2-theta values substantially in accordance with FIG. 30. In another embodiment, Polymorph A exhibits an X-ray powder diffraction pattern obtained using Cu Kα radiation, having peaks with 2-theta values substantially in accordance with Table VI below.

TABLE VI

| Peak | Position [°2Th.] |
|---|---|
| 1. | 4.0 |
| 2. | 11.4 |
| 3. | 11.8 |
| 4. | 19.8 |
| 5. | 21.4 |
| 6. | 21.8 |
| 7. | 22.8 |

In another aspect, this disclosure is directed to a salt or cocrystal of heptadecan-9-yl 8-((2-hydroxyethyl)(6-oxo-6-(undecyloxy)hexyl)amino)octanoate ("Compound 2") and a compound selected from the group consisting of trimesic acid, (−)-2,3-dibenzoyl-L-tartaric acid, 4-acetamido benzoic acid, (+)-L-tartaric acid, and methanesulfonic acid.

In one embodiment, this disclosure also provides Polymorph A of Compound 2 trimesate. In a particular embodiment, Polymorph A of Compound 2 trimesate exhibits an X-ray powder diffraction pattern obtained using Cu Kα radiation, having two, three, four, or more characteristic peaks expressed in degrees 2-theta (+/−0.2) selected from the group consisting of 3.4, 6.8, 10.2, 20.5, and 23.8. In one embodiment, Polymorph A exhibits an X-ray powder diffraction pattern obtained using Cu Kα radiation, having peaks with 2-theta values substantially in accordance with FIG. 38. In another embodiment, Polymorph A exhibits an X-ray powder diffraction pattern obtained using Cu Kα radiation, having peaks with 2-theta values substantially in accordance with Table VII below.

TABLE VII

| Peak | Position [°2Th.] |
|---|---|
| 1. | 3.4 |
| 2. | 6.8 |
| 3. | 10.2 |
| 4. | 20.5 |
| 5. | 23.8 |

In another embodiment, this disclosure also provides Polymorph A of Compound 2 dibenzoyl-L-tartrate. In a particular embodiment, Polymorph A of Compound 2 dibenzoyl-L-tartrate exhibits an X-ray powder diffraction pattern obtained using Cu Kα radiation, having two characteristic peaks expressed in degrees 2-theta (+1-0.2) at 6.1 and 9.1. In one embodiment, Polymorph A exhibits an X-ray powder diffraction pattern obtained using Cu Kα radiation, having peaks with 2-theta values substantially in accordance with FIG. 36, upper profile. In another embodiment, Polymorph A exhibits an X-ray powder diffraction pattern obtained using Cu Kα radiation, having peaks with 2-theta values substantially in accordance with Table VIII below.

TABLE VIII

| Peak | Pos. [°2Th.] |
|---|---|
| 1 | 6.1 |
| 2 | 9.1 |

In yet another embodiment, this disclosure also provides Polymorph A of Compound 2 L-tartrate. In a particular embodiment, Polymorph A of Compound 2 L-tartrate exhibits an X-ray powder diffraction pattern obtained using Cu Kα radiation, having two characteristic peaks expressed in degrees 2-theta (+1-0.2) at 5.4 and 8.1. In one embodiment, Polymorph A exhibits an X-ray powder diffraction pattern obtained using Cu Kα radiation, having peaks with 2-theta values substantially in accordance with FIG. 40, upper profile. In another embodiment, Polymorph A exhibits an X-ray powder diffraction pattern obtained using Cu Kα radiation, having peaks with 2-theta values substantially in accordance with Table IX below.

TABLE IX

| Peak | Position [°2Th.] |
|---|---|
| 1 | 5.4 |
| 2 | 8.1 |

In yet another embodiment, this disclosure also provides Polymorph A of Compound 2 mesylate. In a particular embodiment, Polymorph A of Compound 2 mesylate exhibits an X-ray powder diffraction pattern obtained using Cu Kα radiation, having two, three, or four characteristic peaks expressed in degrees 2-theta (+1-0.2) selected from the group consisting of 4.0, 11.4, 11.8, and 19.8. In one embodiment, Polymorph A exhibits an X-ray powder diffraction pattern obtained using Cu Kα radiation, having peaks with 2-theta values substantially in accordance with FIG. 42. In another embodiment, Polymorph A exhibits an X-ray powder diffraction pattern obtained using Cu Kα radiation, having peaks with 2-theta values substantially in accordance with Table X below.

TABLE X

| Peak | Position [°2Th.] |
|---|---|
| 1. | 4.0 |
| 2. | 11.4 |
| 3. | 11.8 |
| 4. | 19.8 |
| 5. | 27.9 |
| 6. | 36.0 |

In yet another aspect, this disclosure is directed to a salt or cocrystal of heptadecan-9-yl 8-((2-hydroxyethyl)(8-(nonyloxy)-8-oxooctyl)amino)octanoate ("Compound 3") and trimesic acid.

In one embodiment, this disclosure also provides Polymorph A of Compound 3 trimesate. In a particular embodiment, Polymorph A of Compound 3 trimesate exhibits an X-ray powder diffraction pattern obtained using Cu Kα radiation, having two, three, four or more characteristic peaks expressed in degrees 2-theta (+/−0.4) selected from the group consisting of 3.5, 6.8, 10.4, 18.9 and 20.9. In one embodiment, Polymorph A exhibits an X-ray powder diffraction pattern obtained using Cu Kα radiation, having peaks with 2-theta values substantially in accordance with FIG. 46. In another embodiment, Polymorph A exhibits an X-ray powder diffraction pattern obtained using Cu Kα radiation, having peaks with 2-theta values substantially in accordance with Table XI below.

TABLE XI

| Peak | Position [°2Th.] |
|---|---|
| 1. | 3.5 |
| 2. | 6.8 |
| 3. | 10.4 |
| 4. | 18.9 |
| 5. | 20.9 |
| 6. | 24.3 |
| 7. | 27.5 |

In one embodiment, this disclosure also provides Polymorph B of Compound 3 trimesate. In a particular embodiment, Polymorph B of Compound 3 trimesate exhibits an X-ray powder diffraction pattern obtained using Cu Kα radiation, comprising two, three, or more characteristic peaks expressed in degrees 2-theta (+/−0.2) selected from the group consisting of 6.2, 10.8, 16.5, and 26.7. In another embodiment, Polymorph B of Compound 3 trimesate exhibits an X-ray powder diffraction pattern obtained using Cu Kα radiation, having characteristic peaks expressed in degrees 2-theta (+/−0.2) at 6.2, 10.8, 16.5, and 26.7.

In a further embodiment, Polymorph B of Compound 3 trimesate exhibits an X-ray powder diffraction pattern obtained using Cu Kα radiation, having at least five characteristic peaks expressed in degrees 2-theta (+/−0.2), selected from the group consisting of 6.2, 10.8, 12.4, 16.5, 18.7, 22.5, and 26.7. In one embodiment, Polymorph B of Compound 3 trimesate exhibits an X-ray powder diffraction pattern obtained using Cu Kα radiation, pattern having at least six characteristic peaks expressed in degrees 2-theta (+/−0.2), selected from the group consisting of 6.2, 10.8, 12.4, 16.5, 18.7, 22.5, and 26.7.

Figure 48:
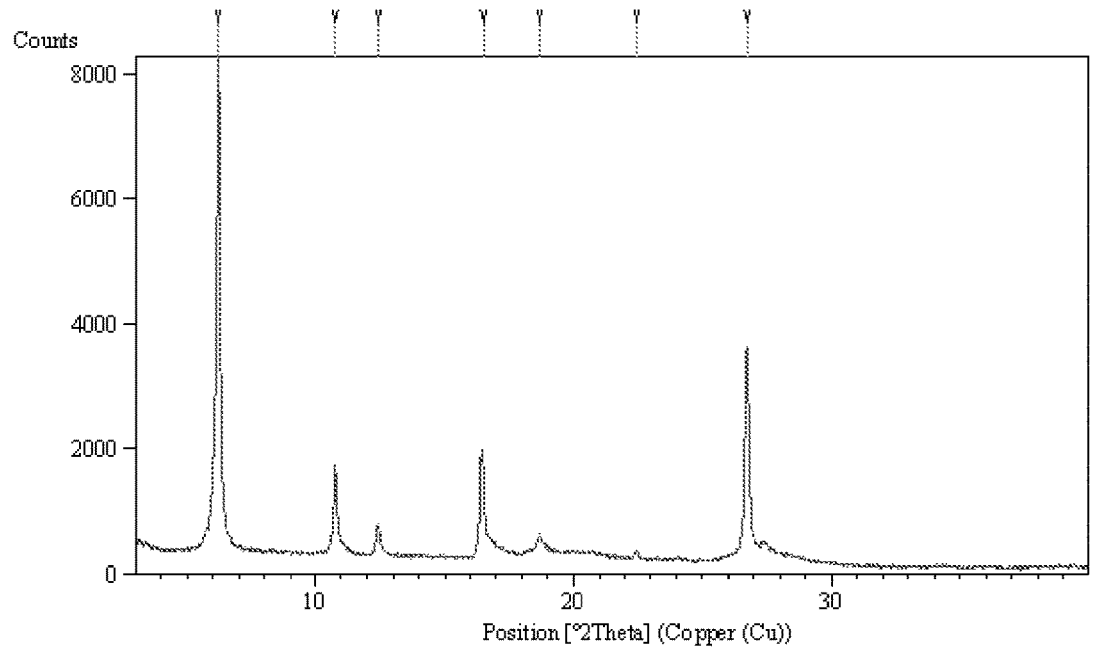
FIG. 48 depicts an XRPD pattern of heptadecan-9-yl 8-((2-hydroxyethyl)(8-(nonyloxy)-8-oxooctyl)amino)octanoate trimesate Polymorph B.

In a particular embodiment, Polymorph B of Compound 3 trimesate exhibits an X-ray powder diffraction pattern obtained using Cu Kα radiation, having two, three, four, or more characteristic peaks expressed in degrees 2-theta (+/−0.4) selected from the group consisting of 6.2, 10.8, 12.4, 16.5, 18.7, 22.5 and 26.7. In one embodiment, Polymorph B exhibits an X-ray powder diffraction pattern obtained using Cu Kα radiation, having peaks with 2-theta values substantially in accordance with FIG. 48. In another embodiment, Polymorph B exhibits an X-ray powder diffraction obtained using Cu Kα radiation, pattern having peaks with 2-theta values substantially in accordance with Table XII below.

TABLE XII

| Peak | Position [°2Th.] |
|---|---|
| 1. | 6.2 |
| 2. | 10.8 |
| 3. | 12.4 |
| 4. | 16.5 |
| 5. | 18.7 |
| 6. | 22.5 |
| 7. | 26.7 |

In other embodiments, Polymorph B of trimesate of Compound 3 is identifiable on the basis of a characteristic peak observed in a differential scanning calorimetry thermogram. In one embodiment, Polymorph B of trimesate of Compound 3 exhibits a differential scanning calorimetry thermogram showing a characteristic melting endotherm peak expressed in units of ° C. with an onset temperature of about 305+/−2° C. In another embodiment, Polymorph A of trimesate of Compound 3 exhibits a differential scanning calorimetry thermogram showing a second primary endotherm expressed in units of ° C. at a temperature of 240+/−2° C. In another embodiment, Polymorph B of trimesate of Compound 3 exhibits a differential scanning calorimetry thermogram substantially in accordance with FIG. 49.

In one embodiment, Polymorph A of trimesate of Compound 3 is substantially free of impurities, meaning there is not a significant amount of impurities present in the sample of Polymorph A. In another embodiment, Polymorph A is a crystalline solid substantially free of amorphous Compound 3 (or any of its amorphous salt forms). In yet another embodiment, Polymorph A is a crystalline solid substantially free of other polymorphs of 4-hydroxybenzoate of Compound 3 and substantially free of amorphous Compound 3 (or any of its amorphous salt forms). For example, Polymorph A is a crystalline solid substantially free of Polymorph B of trimesate of Compound 3 and substantially free of amorphous Compound 3 (or any of its amorphous salt forms). The skilled artisan understands that a solid sample of Polymorph B may also include other polymorphs (e.g., Polymorph A), and/or amorphous Compound 3 (or any of its amorphous salt forms).

In another embodiment, a sample of a salt or cocrystal of Compound 3 comprises Polymorph A of trimesate of Compound 3 substantially free of other polymorphs (e.g., Polymorph B of trimesate of Compound 3). As used herein, the term "substantially free of other polymorphs" means that a sample of crystalline Compound 3 trimesate contains no significant amount of other polymorphs (e.g., Polymorph B). In certain embodiments, at least about 90% by weight of a sample is Polymorph A, with only 10% being other polymorphs (e.g., Polymorph B) and/or amorphous Compound 3 (or any of its amorphous salt forms). In certain embodiments, at least about 95% by weight of a sample is Polymorph A, with only 5% being other polymorphs (e.g., Polymorph B) and/or amorphous Compound 3 (or any of its amorphous salt forms). In still other embodiments, at least about 98% by weight of a sample is Polymorph A, with only 2% by weight being other polymorphs (e.g., Polymorph B) and/or amorphous Compound 3 (or any of its amorphous salt forms). In still other embodiments, at least about 99% by weight of a sample is Polymorph A, with only 1% by weight being other polymorphs (e.g., Polymorph B) and/or amorphous Compound 3 (or any of its amorphous salt forms). In still other embodiments, at least about 99.5% by weight of a sample is Polymorph A, with only 0.5% by weight being other polymorphs (e.g., Polymorph B) and/or amorphous Compound 3 (or any of its amorphous salt forms). In still other embodiments, at least about 99.9% by weight of a sample is Polymorph A, with only 0.1% by weight being other polymorphs (e.g., Polymorph B) and/or amorphous Compound 3 (or any of its amorphous salt forms).

In certain embodiments, a sample of a salt or cocrystal of Compound 3 (e.g., Compound 3 trimesate) may contain impurities. Non-limiting examples of impurities include other polymorph forms, or residual organic and inorganic molecules such as related impurities (e.g., intermediates used to make Compound 3 or by-products), solvents, water or salts. In one embodiment, a sample of a salt or cocrystal of Compound 3, e.g., trimesate Polymorph A is substantially free from impurities, meaning that no significant amount of impurities are present. In another embodiment, a sample of the salt or cocrystal of Compound 3 contains less than 10% weight by weight (wt/wt) total impurities. In another embodiment, a sample of the salt or cocrystal of Compound 3 contains less than 5% wt/wt total impurities. In another embodiment, a sample of the salt or cocrystal of Compound 3 contains less than 2% wt/wt total impurities. In another embodiment, a sample of the salt or cocrystal of Compound 3 contains less than 1% wt/wt total impurities. In yet another embodiment, a sample of the salt or cocrystal of Compound 3 contains less than 0.1% wt/wt total impurities. In yet another embodiment, a sample of the salt or cocrystal of Compound 3 does not contain a detectable amount of impurities.

In one embodiment, this disclosure also provides Polymorph A of MC3 trimesate. In one embodiment, Polymorph A of MC3 trimesate exhibits an X-ray powder diffraction pattern obtained using Cu Kα radiation, comprising two, three, or more characteristic peaks expressed in degrees 2-theta (+/−0.2) selected from the group consisting of 5.2, 7.8, 20.9, and 23.6. In another embodiment, Polymorph A of MC3 trimesate exhibits an X-ray powder diffraction pattern obtained using Cu Kα radiation, having two, three, four, or more characteristic peaks expressed in degrees 2-theta (+/−0.2) selected from the group consisting of 5.2, 7.8, 10.4, 20.9, and 23.6. In a further embodiment, Polymorph A of MC3 trimesate exhibits an X-ray powder diffraction pattern obtained using Cu Kα radiation, having characteristic peaks expressed in degrees 2-theta (+/−0.2) at 5.2, 7.8, 10.4, 18.3, 20.9, 23.6, and 26.2.

In one embodiment, Polymorph A of MC3 trimesate exhibits an X-ray powder diffraction pattern obtained using Cu Kα radiation, having at least seven characteristic peaks expressed in degrees 2-theta (+/−0.2), selected from the group consisting of 5.2, 7.8, 9.7, 10.4, 18.3, 20.9, 23.6, and 26.2. In another embodiment, Polymorph A of MC3 trimesate exhibits an X-ray powder diffraction pattern obtained using Cu Kα radiation, having at least nine characteristic peaks expressed in degrees 2-theta (+/−0.2), selected from the group consisting of 5.2, 7.8, 9.7, 10.4, 11.5, 13.0, 18.3, 20.9, 23.6, and 26.2.

In a particular embodiment, Polymorph A of MC3 trimesate exhibits an X-ray powder diffraction pattern obtained using Cu Kα radiation, having two, three, four or more characteristic peaks expressed in degrees 2-theta (+/−0.2) selected from the group consisting of 5.2, 7.8, 10.4, 18.3, 20.9, 23.6, and 26.2. In one embodiment, Polymorph A exhibits an X-ray powder diffraction pattern obtained using Cu Kα radiation, having peaks with 2-theta values substantially in accordance with FIG. 52. In another embodiment, Polymorph A exhibits an X-ray powder diffraction pattern obtained using Cu Kα radiation, having peaks with 2-theta values substantially in accordance with Table XIII below.

TABLE XIII

| Peak | Position [°2Th.] |
|---|---|
| 1. | 5.2 |
| 2. | 7.8 |
| 3. | 9.7 |
| 4. | 10.4 |
| 5. | 11.5 |
| 6. | 13.0 |
| 7. | 18.3 |
| 8. | 20.9 |
| 9. | 23.6 |
| 10. | 26.2 |

In other embodiments, Polymorph A of trimesate of MC3 is identifiable on the basis of a characteristic peak observed in a differential scanning calorimetry thermogram. In one embodiment, Polymorph A of trimesate of MC3 exhibits a differential scanning calorimetry thermogram showing a characteristic melting endotherm peak expressed in units of ° C. with an onset temperature of about 184+/−2° C. In another embodiment, Polymorph A of trimesate of MC3 exhibits a differential scanning calorimetry thermogram substantially in accordance with the lower curve shown in FIG. 53. In another embodiment, Polymorph A of trimesate of MC3 exhibits a differential scanning calorimetry thermogram showing a characteristic melting endotherm peak expressed in units of ° C. with an onset temperature of about 186+/−2° C. In another embodiment, Polymorph A of trimesate of MC3 exhibits a differential scanning calorimetry thermogram showing a second primary endotherm expressed in units of ° C. at a temperature of 90+/−2° C. In another embodiment, Polymorph A of trimesate of MC3 exhibits a differential scanning calorimetry thermogram substantially in accordance with FIG. 54.

Figure 57:
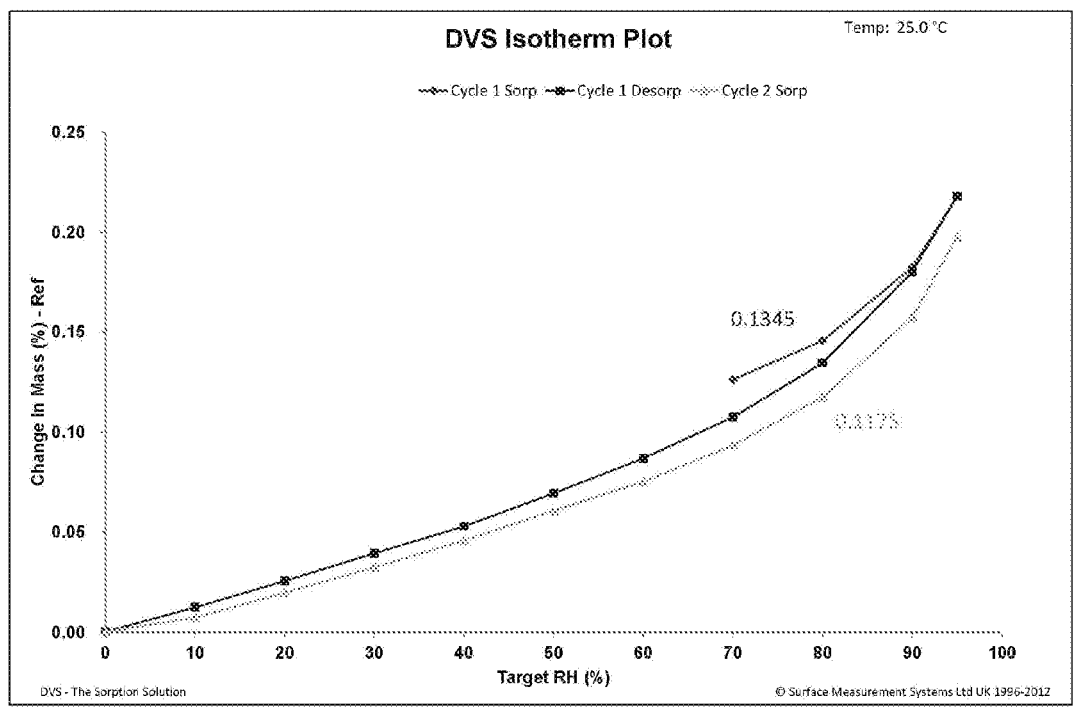
FIG. 57 depicts DVS data at 25° C. for (6Z,9Z,28Z,31Z)-heptatriaconta-6,9,28,31-tetraen-19-yl 4-(dimethylamino) butanoate trimesate Type A polymorphs before and after DVS.
Figure 58:
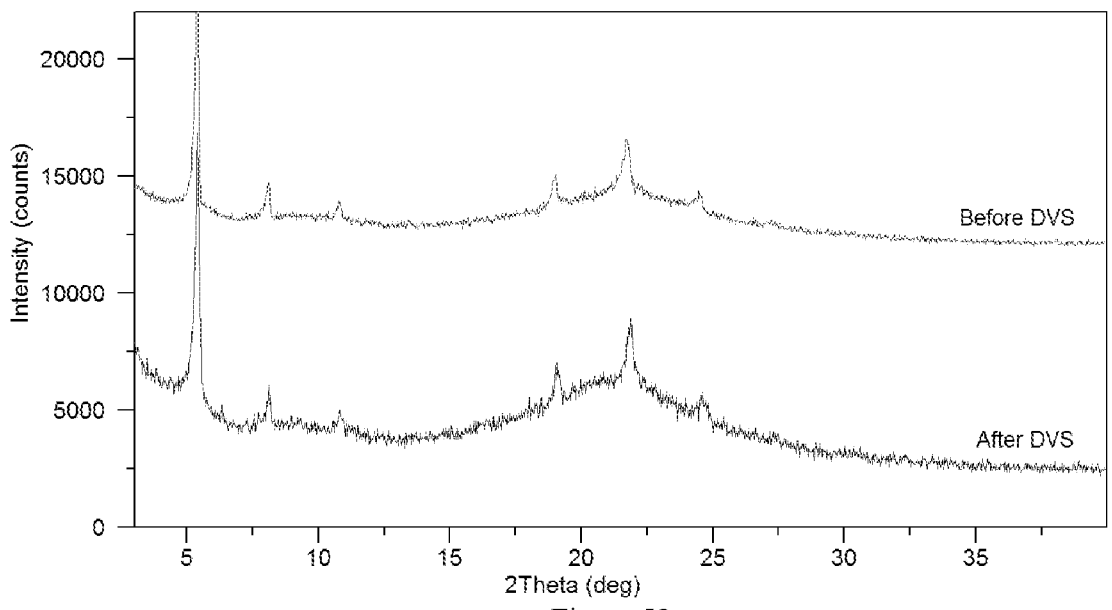
FIG. 58 is an XRPD pattern overlay of (6Z,9Z,28Z,31Z)-heptatriaconta-6,9,28,31-tetraen-19-yl 4-(dimethylamino) butanoate trimesate Type A polymorphs before and after DVS.

In another embodiment, provided herein is Polymorph A of trimesate of MC3, wherein the solid form undergoes a weight increase of less than 1.0% (e.g., less than 0.5%, or less than 0.3%) upon increasing relative humidity from 5.0% to 95.0% at e.g., 25° C. In another embodiment, Polymorph A of trimesate of MC3 is characterized as having a dynamic vapor sorption profile that is substantially in accordance with FIG. 57.

In one embodiment, Polymorph A of trimesate of MC3 is substantially free of impurities, meaning there is not a significant amount of impurities present in the sample of Polymorph A. In another embodiment, Polymorph A is a crystalline solid substantially free of amorphous MC3 (or any of its amorphous salt forms). In yet another embodiment, Polymorph A is a crystalline solid substantially free of other polymorphs of trimesate of MC3 and substantially free of amorphous MC3 (or any of its amorphous salt forms). For example, Polymorph A is a crystalline solid substantially free of Polymorph B of trimesate of MC3 and substantially free of amorphous MC3 (or any of its amorphous salt forms). The skilled artisan understands that a solid sample of Polymorph A may also include other polymorphs (e.g., Polymorph B), and/or amorphous MC3 (or any of its amorphous salt forms).

As used herein, the term "substantially free of amorphous MC3" means that the compound contains no significant amount of amorphous MC3 (or any of its amorphous salt forms). In another embodiment, a sample of a salt or cocrystal of MC3 comprises Polymorph A of trimesate of MC3 substantially free of other polymorphs (e.g., Polymorph B of trimesate of MC3). As used herein, the term "substantially free of other polymorphs" means that a sample of crystalline MC3 trimesate contains no significant amount of other polymorphs (e.g., Polymorph B). In certain embodiments, at least about 90% by weight of a sample is Polymorph A, with only 10% being other polymorphs (e.g., Polymorph B) and/or amorphous MC3 (or any of its amorphous salt forms). In certain embodiments, at least about 95% by weight of a sample is Polymorph A, with only 5% being other polymorphs (e.g., Polymorph B) and/or amorphous MC3 (or any of its amorphous salt forms). In still other embodiments, at least about 98% by weight of a sample is Polymorph A, with only 2% by weight being other polymorphs (e.g., Polymorph B) and/or amorphous MC3 (or any of its amorphous salt forms). In still other embodiments, at least about 99% by weight of a sample is Polymorph A, with only 1% by weight being other polymorphs (e.g., Polymorph B) and/or amorphous MC3 (or any of its amorphous salt forms). In still other embodiments, at least about 99.5% by weight of a sample is Polymorph A, with only 0.5% by weight being other polymorphs (e.g., Polymorph B) and/or amorphous MC3 (or any of its amorphous salt forms). In still other embodiments, at least about 99.9% by weight of a sample is Polymorph A, with only 0.1% by weight being other polymorphs (e.g., Polymorph B) and/or amorphous MC3 (or any of its amorphous salt forms).

In certain embodiments, a sample of a salt or cocrystal of MC3 (e.g., MC3 trimesate) may contain impurities. Non-limiting examples of impurities include other polymorph forms, or residual organic and inorganic molecules such as related impurities (e.g., intermediates used to make MC3 or by-products), solvents, water or salts. In one embodiment, a sample of a salt or cocrystal of MC3, e.g., trimesate Polymorph A is substantially free from impurities, meaning that no significant amount of impurities are present. In another embodiment, a sample of the salt or cocrystal of MC3 contains less than 10% weight by weight (wt/wt) total impurities. In another embodiment, a sample of the salt or cocrystal of MC3 contains less than 5% wt/wt total impurities. In another embodiment, a sample of the salt or cocrystal of MC3 contains less than 2% wt/wt total impurities. In another embodiment, a sample of the salt or cocrystal of MC3 contains less than 1% wt/wt total impurities. In yet another embodiment, a sample of the salt or cocrystal of MC3 contains less than 0.1% wt/wt total impurities. In yet another embodiment, a sample of the salt or cocrystal of MC3 does not contain a detectable amount of impurities.

In one embodiment, this disclosure also provides Polymorph B of MC3 trimesate. In one embodiment, Polymorph B of MC3 trimesate exhibits an X-ray powder diffraction pattern obtained using Cu Kα radiation, having two, three, four or more characteristic peaks expressed in degrees 2-theta (+/−0.2) selected from the group consisting of (+/−0.2) at 4.8, 19.4, 24.3, and 26.8. In a further embodiment, Polymorph B of MC3 trimesate exhibits an X-ray powder diffraction pattern obtained using Cu Kα radiation, having characteristic peaks expressed in degrees 2-theta (+/−0.2) at 4.8, 5.4, 7.2, 9.7, 19.4, 24.3, 26.8, and 29.3.

In one embodiment, Polymorph B of MC3 trimesate exhibits an X-ray powder diffraction pattern obtained using Cu Kα radiation, having at least seven characteristic peaks expressed in degrees 2-theta (+/−0.2), selected from the group consisting of 4.8, 5.4, 7.2, 9.7, 12.1, 19.4, 21.9, 24.3, 26.8, 29.3, and 31.8. In another embodiment, Polymorph B of MC3 trimesate exhibits an X-ray powder diffraction pattern obtained using Cu Kα radiation, having at least nine characteristic peaks expressed in degrees 2-theta (+/−0.2), selected from the group consisting 4.8, 5.4, 7.2, 9.7, 12.1, 14.5, 17.0, 19.4, 21.9, 24.3, 26.8, and 29.3.

In a particular embodiment, Polymorph B of MC3 trimesate exhibits an X-ray powder diffraction pattern obtained using Cu Kα radiation, having two, three, four or more characteristic peaks expressed in degrees 2-theta (+/−0.2) selected from the group consisting of 4.8, 5.4, 7.2, 9.7, 19.4, 24.3, 26.8, and 29.3. In one embodiment, Polymorph B exhibits an X-ray powder diffraction pattern obtained using Cu Kα radiation, having peaks with 2-theta values substantially in accordance with FIG. 59. In another embodiment, Polymorph B exhibits an X-ray powder diffraction pattern obtained using Cu Kα radiation, having peaks with 2-theta values substantially in accordance with Table XIV below.

TABLE XIV

| Peak | Position [°2Th.] |
| --- | --- |
| 1. | 4.8 |
| 2. | 5.4 |
| 3. | 7.2 |
| 4. | 9.7 |
| 5. | 12.1 |
| 6. | 14.5 |
| 7. | 17.0 |
| 8. | 19.4 |
| 9. | 21.9 |
| 10. | 24.3 |
| 11. | 26.8 |
| 12. | 29.3 |
| 13. | 31.8 |

In other embodiments, Polymorph B of trimesate of MC3 is identifiable on the basis of a characteristic peak observed in a differential scanning calorimetry thermogram. In one embodiment, Polymorph B of trimesate of MC3 exhibits a differential scanning calorimetry thermogram showing a characteristic melting endotherm peak expressed in units of ° C. with an onset temperature of about 187+/−2° C. In another embodiment, Polymorph B of trimesate of MC3 exhibits a differential scanning calorimetry thermogram substantially in accordance with FIG. 60.

In one embodiment, Polymorph B of trimesate of MC3 is substantially free of impurities, meaning there is not a significant amount of impurities present in the sample of Polymorph B. In another embodiment, Polymorph B is a crystalline solid substantially free of amorphous MC3 (or any of its amorphous salt forms). In yet another embodiment, Polymorph B is a crystalline solid substantially free of other polymorphs of trimesate of MC3 and substantially free of amorphous trimesate of MC3 (or any of its amorphous salt forms). For example, Polymorph B is a crystalline solid substantially free of Polymorph A of trimesate of MC3 and substantially free of amorphous trimesate of MC3 (or any of its amorphous salt forms). The skilled artisan understands that a solid sample of Polymorph B may also include other polymorphs (e.g., Polymorph A), and/or amorphous MC3 (or any of its amorphous salt forms). As used herein, the term "substantially free of amorphous MC3" means that the compound contains no significant amount of amorphous MC3 (or any of its amorphous salt forms).

In another embodiment, a sample of a salt or cocrystal of MC3 comprises Polymorph B of trimesate of MC3 substantially free of other polymorphs (e.g., Polymorph A of trimesate of MC3).

As used herein, the term "substantially free of other polymorphs" means that a sample of crystalline MC3 trimesate contains no significant amount of other polymorphs (e.g., Polymorph A). In certain embodiments, at least about 90% by weight of a sample is Polymorph B, with only 10% being other polymorphs (e.g., Polymorph A) and/or amorphous MC3 (or any of its amorphous salt forms). In certain embodiments, at least about 95% by weight of a sample is Polymorph B, with only 5% being other polymorphs (e.g., Polymorph A) and/or amorphous MC3 (or any of its amorphous salt forms). In still other embodiments, at least about 98% by weight of a sample is Polymorph B, with only 2% by weight being other polymorphs (e.g., Polymorph A) and/or amorphous MC3 (or any of its amorphous salt forms). In still other embodiments, at least about 99% by weight of a sample is Polymorph B, with only 1% by weight being other polymorphs (e.g., Polymorph A) and/or amorphous MC3 (or any of its amorphous salt forms). In still other embodiments, at least about 99.5% by weight of a sample is Polymorph B, with only 0.5% by weight being other polymorphs (e.g., Polymorph A) and/or amorphous MC3 (or any of its amorphous salt forms). In still other embodiments, at least about 99.9% by weight of a sample is Polymorph B, with only 0.1% by weight being other polymorphs (e.g., Polymorph A) and/or amorphous MC3 (or any of its amorphous salt forms).

In certain embodiments, a sample of a salt or cocrystal of MC3 (e.g., MC3 trimesate) may contain impurities. Non-limiting examples of impurities include other polymorph forms, or residual organic and inorganic molecules such as related impurities (e.g., intermediates used to make MC3 or by-products), solvents, water or salts. In one embodiment, a sample of a salt or cocrystal of MC3, e.g., trimesate Polymorph B is substantially free from impurities, meaning that no significant amount of impurities are present. In another embodiment, a sample of the salt or cocrystal of MC3 contains less than 10% weight by weight (wt/wt) total impurities. In another embodiment, a sample of the salt or cocrystal of MC3 contains less than 5% wt/wt total impurities. In another embodiment, a sample of the salt or cocrystal of MC3 contains less than 2% wt/wt total impurities. In another embodiment, a sample of the salt or cocrystal of MC3 contains less than 1% wt/wt total impurities. In yet another embodiment, a sample of the salt or cocrystal of MC3 contains less than 0.1% wt/wt total impurities.

Also disclosed herein is a salt or cocrystal of an alkylated Compound 1 (structure of which is shown below, wherein R is an alkyl having, e.g., 1-20 carbon atoms) and a coformer compound such as those disclosed herein, e.g., 4-hydroxybenzoic acid, oxalic acid, trimellitic acid, orotic acid, trimesic acid, sulfuric acid, (−)-2,3-dibenzoyl-L-tartaric acid, 4-acetamido benzoic acid, (+)-L-tartaric acid, and methanesulfonic acid. For example, the salt or cocrystal of an alkylated Compound 1 has a melting point of about 50° C. or greater (e.g., about 60° C., 70° C., or greater).

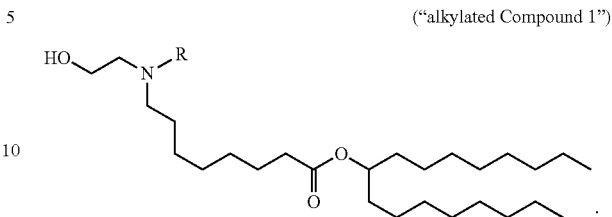

("alkylated Compound 1")

The salts or cocrystals disclosed herein may comprise Compound 1 (or Compound 2 or 3) and the coformer compound (e.g., an acid), within a ratio from 1:0.2 mol/mol to 1:5 mol/mol or from about 1:0.5 mol/mol to 1:2 mol/mol, or from 1:0.4 mol/mol to 1:1.1 mol/mol. For example, the molar ratio is about 1:1 mol/mol.

The salts or cocrystals disclosed herein may comprise (6Z,9Z,28Z,31Z)-heptatriaconta-6,9,28,31-tetraen-19-yl 4-(dimethylamino)butanoate ("MC3") and the coformer compound (e.g., an acid), within a ratio from 1:0.5 mol/mol (i.e., 2:1 mol/mol) to 1:2 mol/mol.

The salts or cocrystals disclosed herein may be anhydrous and/or essentially solvent-free form, or be in hydrate and/or solvate form. For example, 4-hydroxybenzoate of Compound 1 is anhydrous. For example, Compound 1 orotate may be anhydrous or in a hydrate or solvate form.

Preparation of Salts or Cocrystals and Polymorphs Thereof

General techniques for making polymorphs are understood by the skilled artisan. Conventionally, a salt form or cocrystal is prepared by combining in solution the free base compound and a coformer (e.g., an acid coformer) containing the anion of the salt form desired, and then isolating the solid salt or cocrystal product from the reaction solution (e.g., by crystallization, precipitation, evaporation, etc.). Other salt-forming or cocrystallization techniques may be employed.

In one aspect, provided herein is a method of preparing a salt or cocrystal of Compound 1 by combining Compound 1 with a compound selected from the group consisting of 4-hydroxybenzoic acid, oxalic acid, trimellitic acid, orotic acid, trimesic acid, and sulfuric acid. In one embodiment, the method comprises the steps: a) dissolving Compound 1 in a solvent to obtain a solution; b) combining the coformer compound with the solution; c) precipitating or crystallizing the salt or cocrystal from the solution; and d) collecting the salt or cocrystal. In one embodiment, the solvent used in step a) is n-heptane, ethyl acetate, or cyclohexane. In one embodiment, step c) is carried out substantively free of evaporation to obtain 4-hydroxybenzoate, trimellitate, orotate, and trimesate of Compound 1. In another embodiment, step c) is carried out by slow evaporation, at e.g., 5° C., to obtain, e.g., sulfate of Compound 1. In some embodiments, the molar ratio of Compound 1 and the compound is about 1:1.

Also provided herein is a method for preparing a salt or cocrystal of Compound 2 by combining Compound 2 with a compound selected from the group consisting of trimesic acid, (−)-2,3-dibenzoyl-L-tartaric acid, 4-acetamido benzoic acid, (+)-L-tartaric acid, and methanesulfonic acid. In one embodiment, the method comprises the steps: a) dissolving Compound 2 in a solvent to obtain a solution; b) combining the coformer compound with the solution; c) precipitating or crystallizing the salt or cocrystal from the solution; and d) collecting the salt or cocrystal. In one embodiment, the solvent used in step a) is n-heptane, ethyl acetate, or cyclohexane. In one embodiment, step c) is carried out substantively free of evaporation to obtain trimesate, dibenzoyl-L-tartrate, or 4-acetamido benzoate of Compound 2. In another embodiment, step c) is carried out by slow evaporation, at e.g., 5° C., to obtain, e.g., dibenzoyl-L-tartrate, L-tartrate, or mesylate of Compound 2. In some embodiments, the molar ratio of Compound 2 and the compound is about 1:1.

This disclosure also provides a method of preparing the salt or cocrystal of Compound 3 by combining Compound 3 and trimesic acid. In one embodiment, the method comprises the steps: a) dissolving Compound 3 in a solvent to obtain a solution; b) combining trimesic acid with the solution; c) precipitating or crystallizing the salt or cocrystal from the solution; and d) collecting the salt or cocrystal. In one embodiment, the solvent used in step a) is n-heptane or toluene. In one embodiment, step c) is carried out substantively free of evaporation. In another embodiment, step c) is carried out by slow evaporation. In some embodiments, the molar ratio of Compound 3 and the compound is about 1:1.

This disclosure also provides a method of preparing the salt or cocrystal of MC3 by combining MC3 and a compound selected from (+)-O,O-di-pivaloyl-D-tartaric acid (DPDT), (−)-O,O-di-pivaloyl-L-tartaric acid (DPLT), (+)-2,3-dibenzoyl-D-tartaric acid (DBDT), and trimesic acid. In one embodiment, the method comprises the steps: a) dissolving MC3 in a solvent to obtain a solution; b) combining the compound with the solution; c) precipitating or crystallizing the salt or cocrystal from the solution; and d) collecting the salt or cocrystal. In one embodiment, the solvent used in step a) is ethyl acetate, toluene, or cyclohexane. In one embodiment, step c) is carried out substantively free of evaporation. In another embodiment, step c) is carried out by slow evaporation. In some embodiments, the molar ratio of MC3 and the compound is about 1:1.

This disclosure also provides a method of preparing the salt or cocrystal of MC3 by combining MC3 and a compound selected from (+)-O,O-di-pivaloyl-D-tartaric acid (DPDT), (−)-O,O-di-pivaloyl-L-tartaric acid (DPLT), (+)-2,3-dibenzoyl-D-tartaric acid (DBDT), and trimesic acid. In one embodiment, the method comprises the steps: a) combining MC3 and trimesic acid; b) dissolving the combination of MC3 and the compound to obtain a solution; c) precipitating or crystallizing the salt or cocrystal from the solution; and d) collecting the salt or cocrystal. In one embodiment, the solvent used in step a) is ethyl acetate, toluene, or cyclohexane. In one embodiment, step c) is carried out substantively free of evaporation. In another embodiment, step c) is carried out by slow evaporation. In some embodiments, the molar ratio of MC3 and the compound is about 1:1.

In one embodiment of the method, the solvent comprises an aprotic solvent. In one embodiment of the method, the solvent comprises a nonpolar aprotic solvent. In certain embodiments, one or more of the solutions of steps a) or b) is heated. For example, the solution from step b) is subject to temperature cycling, e.g., from about 50° C. to about 5° C. (for e.g., twice, three, or four times) before step c).

Also provided herein is a process of purifying Compound 1, 2, or 3 by forming a salt or cocrystal thereof disclosed herein to separate the salt or cocrystal thereof from the impurities. The method may further comprise neutralizing the salt or cocrystal to convert to Compound 1, 2, or 3 (i.e., a free base).

Also provided herein is a process of purifying MC3 by forming a salt or cocrystal thereof disclosed herein to separate the salt or cocrystal thereof from the impurities. The method may further comprise neutralizing the salt or cocrystal to convert to MC3 (i.e., a free base).

In still another aspect, provided herein is a process of synthesizing Compound 2, Compound 3, or an analog thereof by reacting a salt or cocrystal of Compound 1 disclosed herein with a suitable electrophile, such as an ester substituted with a halogen (e.g., Br or I). The scheme below illustrates one embodiment of the process.

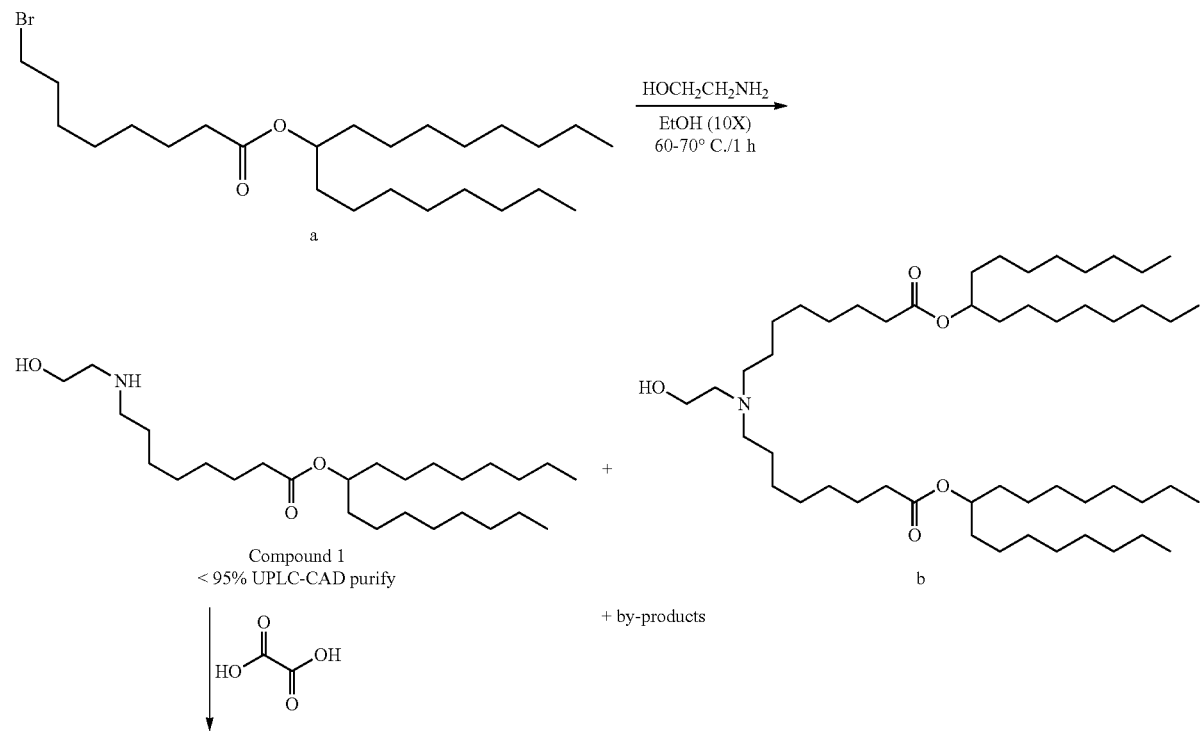

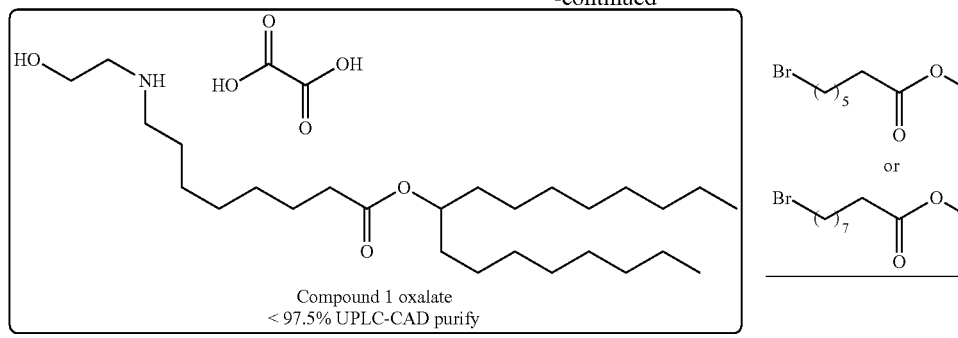

Compound 1 oxalate
< 97.5% UPLC-CAD purify or Compound 2 or 3

In the scheme above, Compound 1 is oil and it is hard to purify it, e.g., by separating it from a and b, and other by-products. Compound 1 oxalate is a crystal, thus is easy to separate from a, b, and/or other by-products. Forming a salt or cocrystal of Compound 1, e.g., oxalate, improves purification. Also, Compound 1 oxalate can be used to synthesize Compound 2 or 3 without converting back to Compound 1 (i.e., neutralization).

A process for synthesizing MC3 is described in Jayaraman, M.; Maximizing the Potency of siRNA Lipid Nanoparticles for Hepatic Gene Silencing In Vivo, Angew. Chem. Int. Ed. 2012, 51, 8529-8533, which is incorporated herein by reference in its entirety. MC3 corresponds to compound 16 in this article.

In one embodiment, the process of the present disclosure is advantageous as compared to other processes in that the process of the disclosure produces Compound 1, 2, or 3 or a salt or cocrystal thereof at a large scale and/or at a high purity, e.g., such that cumbersome purification (e.g., column chromatography, extraction, phase separation, distillation and solvent evaporation) is not needed. In one embodiment, the process of the present disclosure is able to process at least 100 g, 200 g, 500 g or more (e.g., 1 kg, 2 kg, 5 kg, 10 kg, 20 kg, 50 kg, 100 kg, 200 kg, 500 kg, or 1000 kg or more) Compound 1, 2, or 3 or a salt or cocrystal thereof without the need to scale up. In one embodiment, the process of the present disclosure is able to produce Compound 1, 2, or 3 or a salt or cocrystal thereof at least at a purity of at least 75%, 80%, 85%, 90%, 95%, 96%, 97%, 98%, 99%, or 99.5%, or higher. In one embodiment, the process of the present disclosure is able to produce Compound 1, 2, or 3 or a salt or cocrystal thereof with little or none impurity. In one embodiment, the impurity produced in the process of the present disclosure, even if produced, is easy to be separated from Compound 1, 2, or 3 or a salt or cocrystal thereof, without cumbersome purification (e.g., column chromatography, extraction, phase separation, distillation and solvent evaporation).

All percentages and ratios used herein, unless otherwise indicated, are by weight (i.e., weight by weight or wt/wt). Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

X-Ray Powder Diffraction

XRPD was performed with PANalytical Empyrean, X' Pert3, and Bruker D2 X-ray powder diffractometers. The parameters used are listed in the table below.

| Parameters | XRPD | | |
|---|---|---|---|
| Model | Empyrean | X' Pert3 | Bruker D2 |
| X-Ray wavelength | Cu, kα, Kα1 (Å): 1.540598, Kα2 (Å): 1.544426 Kα2/Kα1 intensity ratio: 0.50 | | |
| X-Ray tube setting | 45 kV, 40 mA | | 30 kV, 10 mA |
| Divergence slit | Automatic | 1/8° | 0.6 mm |
| Scan mode | Continuous | | |
| Scan range (°2-theta) | 3-40 | | |
| Scan step time (s) | 17.8 | 46.7 | 0.1 |
| Step size (°2-theta) | 0.0167 | 0.0263 | 0.0201 |
| Scan speed (°/min) | 5 min 30 s | 5 min 04 s | 3 min 27 s |

TGA/DSC

TGA data were collected using a TA Q500/Q5000 TGA from TA Instruments. DSC was performed using a TA Q200/Q2000 DSC from TA Instruments. Detailed parameters used are listed in the following table.

| Parameters | TGA | DSC |
|---|---|---|
| Method | Ramp | Ramp |
| Sample pan | Aluminum or platinum, open | Aluminum or platinum, crimped |
| Temperature | RT—desired temperature; or -60° C.—desired temperature; RT-350° C. | or -60° C.—desired temperature; or RT-300° C. |
| Heating rate | 10° C./min | |
| Purge gas | $N_2$ | |

HPLC

Agilent 1100 or Agilent 1100/1260 HPLC was utilized to analyze purity, with the detailed method listed in the table below.

| HPLC | Agilent 1100 with DAD Detector | Agilent 1100/1260 |
|---|---|---|
| Column | Agilent Eclipse Plus C18, 150 × 4.6 mm, 5 μm | Agilent ZORBAX SB-Phenyl, 150 × 4.6 mm, 3.5 μm |
| Mobile phase | A: 0.1% TFA in H2O B: 0.1% TFA in Acetonitrile | |

-continued

|  | Time (min) | % B | Time (min) | % B |
|---|---|---|---|---|
| Gradient table | 0.0 | 30 | 0.0 | 10 |
|  | 15.0 | 100 | 4.0 | 80 |
|  | 22.0 | 100 | 6.0 | 80 |
|  | 22.1 | 30 | 6.10 | 10 |
|  | 25.0 | 30 | 8.0 | 10 |
| Run time | 25.0 min | | 8.0 min | |
| Post time | 0.0 min | | 0.0 min | |
| Flow rate | 0.8 mL/min | | 1.0 mL/min | |
| Injection volume | 5 µL | | 10 µL | |
| Column temperature | | 40° C. | | |
| Sample temperature | | RT | | |
| Diluent | MeOH | | EtOH | |
| Detector | ELSD | Grace 3300 | Detector wavelength | |
|  | Temperature | 50° C. | UV at 210 nm, reference 500 nm | |
|  | Flow | 2 L/min | | |
|  | Gain | 1 | | |

Agilent 1100/1260 HPLC with Halo C18 column was utilized for purity and concentration measurements of MC3 free base, with the detailed method listed in the table below.

| Parameter | Condition |
|---|---|
| Column | Halo C18, 100 × 4.6 mm, 2.7 µm |
| Mobile phase | A: 20% $NH_4HCO_3$ (10 mM) + 40% MeOH + 40% THF |
|  | B: 20% IPA + 40% MeOH + 40% THF |

|  | Time (min) | % B |
|---|---|---|
| Gradient table | 0.00 | 0 |
|  | 30.00 | 40 |
|  | 35.00 | 50 |
|  | 35.01 | 0 |
|  | 40.00 | 0 |
| Run time | 40.0 min | |
| Post time | 0.0 min | |
| Flow rate | 10 mL/min | |
| Injection volume | 10 µL | |
| Detector wavelength | UV at 207 nm, reference 500 nm | |
| Column temperature | 40° C. | |
| Sample temperature | RT | |
| Diluent | EtOH | |

Dynamic Vapor Sorption

DVS was measured on via a SMS (Surface Measurement Systems) DVS Intrinsic. The relative humidity at 25° C. were calibrated against deliquescence point of LiCl, $Mg(NO_3)_2$ and KCl. Actual parameters for DVS test are listed in the table below.

| Parameters | DVS |
|---|---|
| Temperature | 25° C. |
| Sample size | 10~20 mg |
| Gas and flow rate | N2, 200 mL/min |
| dm/dt | 0.002%/min |
| Min. dm/dt stability duration | 10 min |
| Max. equilibrium time | 180 min |

-continued

| Parameters | DVS |
|---|---|
| RH range | 0%RH-95%RH |
| RH step size | 10% (0% RH-90% RH, 90% RH-0% RH) |
|  | 5% (90% RH-95% RH, 95% RH-90% RH) |

$^1$H NMR spectrum was collected on Bruker 400M NMR Spectrometer using DMSO-d6 as solvent.

Polarized light microscopic (PLM) images were captured on Axio Lab A1 upright microscope at room temperature.

Example 1: Salts or Cocrystals of Compound 1

Preparation

Figure 34:
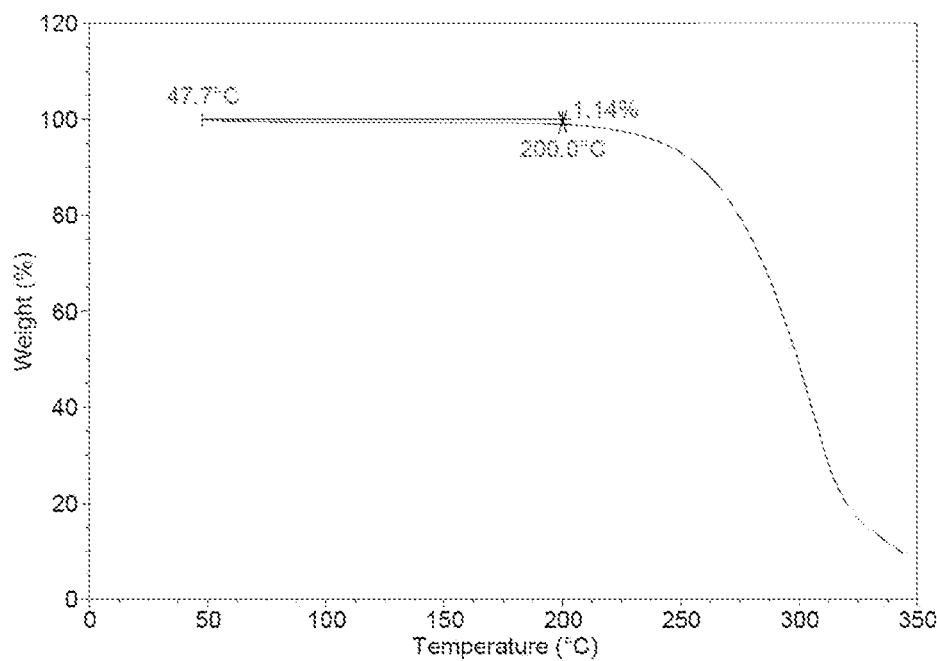
FIG. 34 depicts TGA data of heptadecan-9-yl 8-((2-hydroxyethyl)amino)octanoate.
Figure 35:
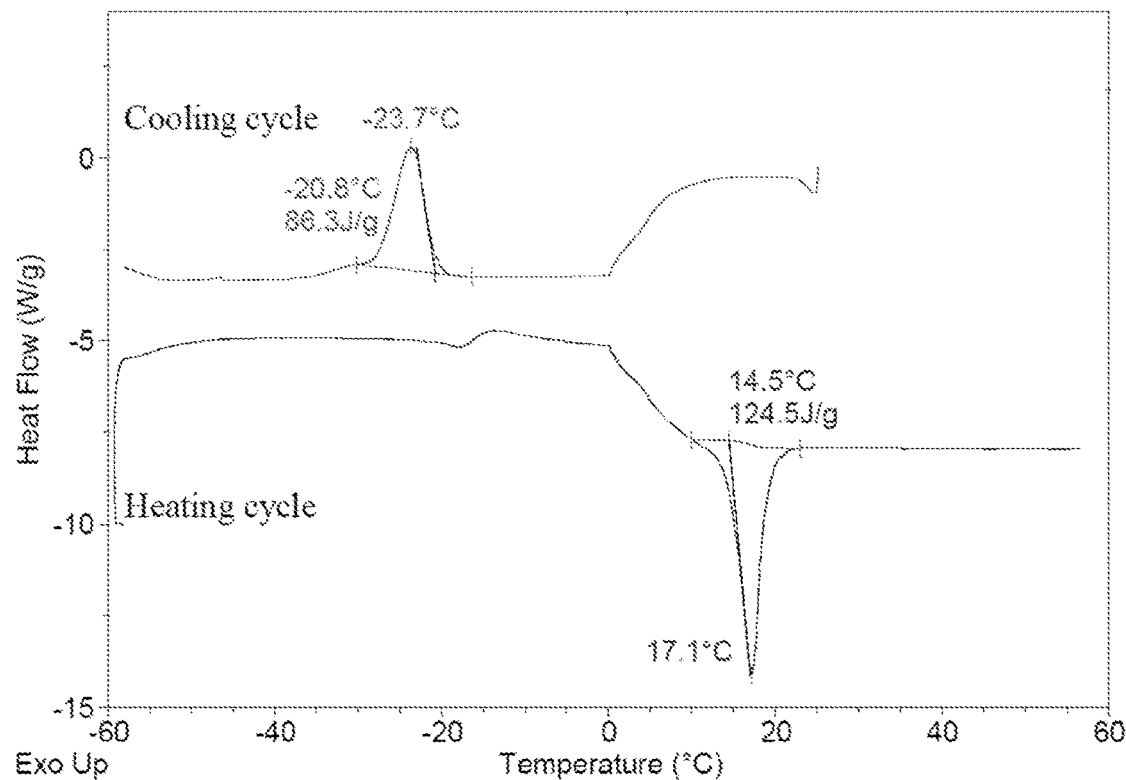
FIG. 35 depicts cyclic DSC data of heptadecan-9-yl 8-((2-hydroxyethyl)amino)octanoate (heating/cooling rate: 10° C./min).

Compound 1 freebase is an oil at ambient conditions. As per the results in FIGS. 34 and 35, the freebase showed minor weight loss of 1.1% before 200° C. in TGA, and possible crystallization and melting signals in cyclic DSC, suggesting the existence of a crystalline form which melts around 17° C. (peak). Purity of the material was determined to be 99.95 area % by HPLC with ELSD detector.

To identify a crystalline salt form or cocrystal of Compound 1, screening was performed under 96 conditions using 32 acids and three solvent systems. Compound 1 freebase was dispersed in selected solvent with a 1.5-mL glass vial and corresponding salt former was added with a molar charge ratio of 1:1. The mixtures of freebase and the coformer compound (e.g., an acid) were first transferred to temperature cycling from 50° C. to 5° C. for two cycles (heating rate of 4.5° C./min, cooling rate of 0.1° C./min) and then stirred at 5° C. to induce precipitation. If the samples were still clear, they would be subjected to evaporation at different temperatures (5° C. or RT) to dryness. Resulted solids were isolated and analyzed.

Isolated crystal solids were characterized by X-ray powder diffraction (XRPD), thermo-gravimetric analysis (TGA) and differential scanning calorimetry (DSC), with proton nuclear magnetic resonance ($^1$H NMR) to confirm the freebase chemical structure and also potential co-existence with some organic acids. Exemplary data from the initial findings are summarized in Table 1.

TABLE 1

|   | | n-Heptane | EtOAc | Cyclohexane |
|---|---|---|---|---|
| 1 | Hexanoic acid | Amorphous* | Amorphous* | Oil** |
| 2 | Fumaric acid | Acid + two extra peaks | Acid + two extra peaks* | Acid + two extra peaks |
| 3 | Adipic acid | Amorphous* | Amorphous* | Acid + one extra peak** |
| 4 | Suberic acid | Amorphous* | Acid* | Oil** |
| 5 | Cinnamic acid | Amorphous* | Amorphous* | Oil** |
| 6 | Benzoic acid, 4-acetamido | Acid | Two peaks* | Acid |
| 7 | (S)-Mandelic acid | Two peaks* | Two peaks* | Oil** |
| 8 | (−)-O,O-Di-pivaloyl-L-tartaric acid | Amorphous* | Amorphous* | Oil** |
| 9 | Terephthalic acid | Acid | Acid | Acid |
| 10 | Trimesic acid | Amorphous | Trimesate Polymorph A | Oil** |
| 11 | Citric acid | Two peaks* | Amorphous* | Two peaks** |
| 12 | Succinic acid | Two peaks* | Two peaks* | Two peaks** |
| 13 | Malonic acid | Amorphous* | Amorphous* | Oil** |
| 14 | (+)-Camphor-10-sulfonic acid | Amorphous* | Amorphous* | Oil** |
| 15 | Nicotinic acid | Amorphous* | Acid* | Oil** |
| 16 | (+)-L-tartaric acid | Two peaks | Two peaks* | Oil** |
| 17 | p-Toluenesulfonic acid | Amorphous* | Two peaks* | Oil** |
| 18 | Hydrochloric acid | Amorphous* | Amorphous* | Amorphous** |
| 19 | Sulfuric acid | Sulfate Polymorph A* | Amorphous* | Oil** |
| 20 | Phosphoric acid | Two peaks* | Amorphous* | Oil** |
| 20 | Acetic acid | Amorphous* | Amorphous* | Oil** |
| 21 | Methanesulfonic acid | Amorphous* | Amorphous* | Oil** |
| 22 | Sebacic acid | Sebacic acid | Sebacic acid* | Sebacic acid* |
| 23 | Benzoic acid | Amorphous* | Amorphous* | Amorphous* |
| 24 | 1,2,4-Trimellitic acid | Trimellitate Polymorph A | Trimellitate Polymorph A | Trimellitate Polymorph A |
| 25 | Phthalic acid | Oil* | Oil* | Oil* |
| 26 | Isophthalic acid | Isophthalic acid | Isophthalic acid | Isophthalic acid |
| 27 | Orotic acid | Orotate Polymorph A | Orotate Polymorph A | Orotate Polymorph A |
| 28 | 4-Hydroxybenzoic acid | 4-Hydroxybenzoate Polymorph A | 4-Hydroxybenzoate Polymorph A | 4-Hydroxybenzoate Polymorph A |
| 29 | (−)-Dibenzoyl-L-tartaric acid | Weakly crystalline | Amorphous* | Weakly crystalline |
| 30 | 2,5-Dihydroxybenzoic acid | Oil* | Oil* | 2,5-Dihydroxybenzoic acid |
| 31 | 2-Hydroxy benzoic acid | Oil** | Oil** | Oil** |
| 32 | 3-Hydroxy benzoic acid | Oil** | Oil** | Oil** |

*clear solutions obtained after 5° C. stirring were transferred to 5° C. evaporation.
**clear solutions obtained after 5° C. stirring were slow evaporated at RT.

Among them, five crystalline hits were discovered, including 4-hydroxybenzoate, trimellitate, orotate, trimesate and sulfate. Table 2 summarizes the properties of certain polymorphs of the salts or cocrystals.

TABLE 2

| | 4-Hydroxybenzoate | Trimellitate | Orotate | |
|---|---|---|---|---|
| | Polymorph A | Polymorph A | Polymorph A | Polymorph B |
| Appearance | White powder | Wax-like solid | Wax-like solid | |
| Solid form | Anhydrate | Hydrate | Anhydrate/Hydrate | Hydrate/solvate |
| Crystallinity | High | Medium | Medium | |
| Purity, area % | 99.96 | 99.97 | — | 99.97 |
| TGA weight loss, % | 0.7-1.7 | 1.5-3.4 | 4.0 | 4.0 |
| DSC endotherm, ° C. (onset) | 66.8, 101.8 (batch 1) 68.2, 103.5 (batch 2) | 78.3, 137.1 (batch 1) 80.0*, 137.1 (batch 2) | 78.8*, 85.1*, 176.3* | 83.5* |
| Hygroscopicity (form change after DVS) | Non-hygroscopic (no) | Slightly hygroscopic (no) | — | Hygroscopic (convert to orotate Polymorph A) |

*peak temperature.
—: no data available.

Three crystalline polymorphs of Compound 1 (4-hydroxybenzoate Polymorph A, trimellitate Polymorph A and orotate Polymorph B) were prepared to larger scale for further investigation, with the detailed procedure shown below:

1. About 100 mg of freebase Compound 1 was added into a 3-mL glass vial;
2. Add corresponding acids (molar charge ratio is 1:1) into the vial;
3. Add 0.5 mL of solvent and transfer the suspension to temperature cycling from 50° C. to 5° C. (cooling rate of 0.1° C./min, two cycles) with magnetic stirring.
4. Centrifuge to isolate solids and vacuum dry at RT.

Characterization of 4-hydroxybenzoate

Figure 2:
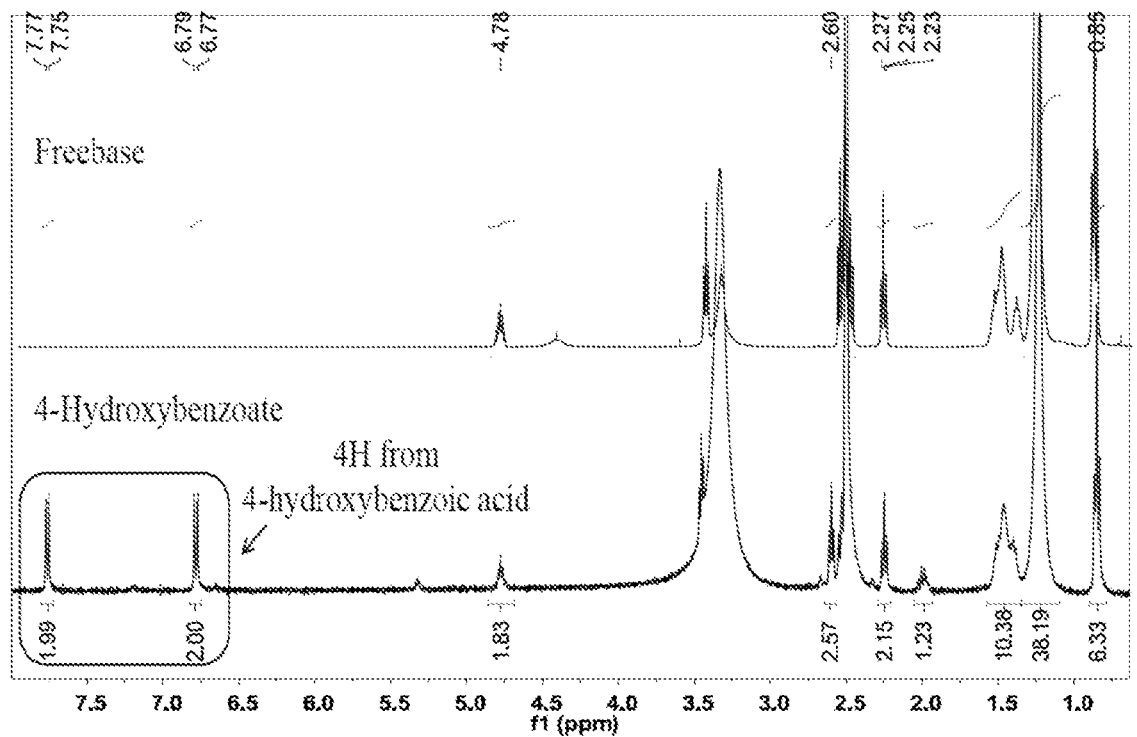
FIG. 2 depicts a $^1$H NMR spectrum of heptadecan-9-yl 8-((2-hydroxyethyl)amino)octanoate 4-hydroxybenzoate Polymorph A, batch No. 2.

Two batches of 4-hydroxybenzoate Polymorph A (or Type A) (batch Nos. 1 and 2) were prepared by slurry in n-heptane and showed high crystallinity as characterized by XRPD in FIG. 1. The $^1$H NMR of sample (batch No. 2) was collected with spectrum shown in FIG. 2. Besides freebase, a certain amount of 4-hydroxybenzic acid was detected in $^1$H NMR (signals around 6.7 and 7.7 ppm), indicating the possibility of salt formation.

Figure 3:
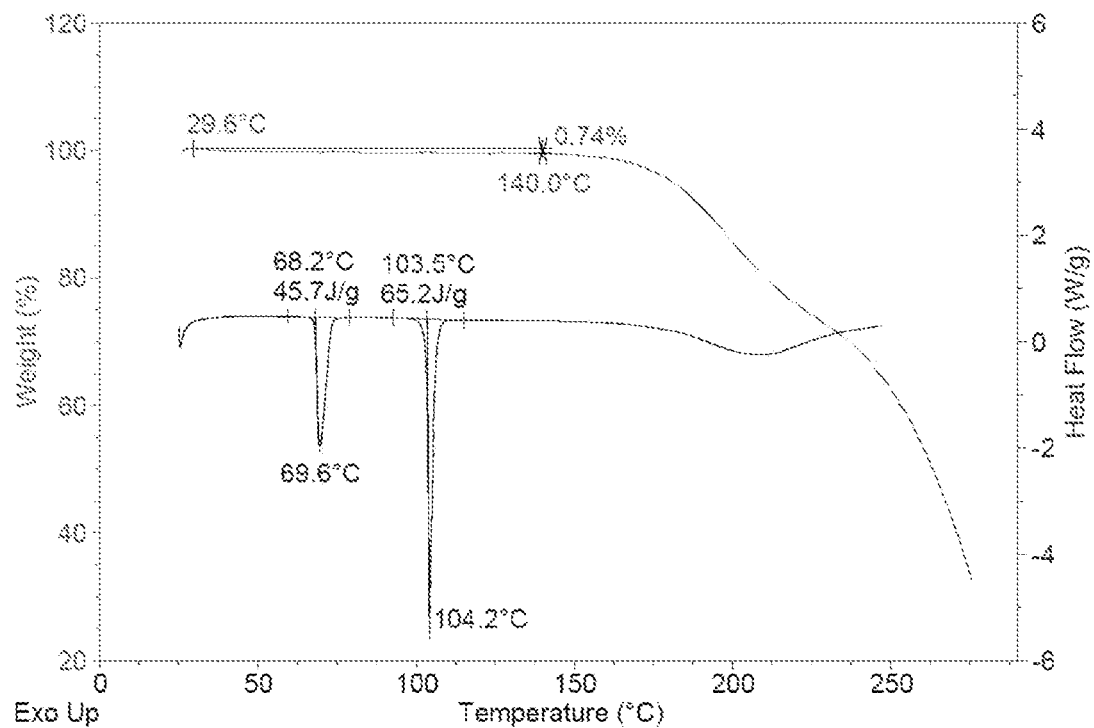
FIG. 3 depicts thermo-gravimetric analysis (TGA) and differential scanning calorimetry (DSC) data for heptadecan-9-yl 8-((2-hydroxyethyl)amino)octanoate 4-hydroxybenzoate Polymorph A, batch No. 2.

As indicated by the TGA and DSC data in FIG. 3, sample (batch No. 2) showed a weight loss of 0.7% up to 140° C. and two sharp endothermic peaks at 68.2° C. and 103.5° C. (onset temperature) before decomposition. Based on the negligible weight loss in TGA, 4-hydroxybenzoate Polymorph A was considered to be an anhydrous form. In addition, the two sharp endothermic signals in DSC curve implied the possible existence of another anhydrous form at higher temperature.

Figure 4:
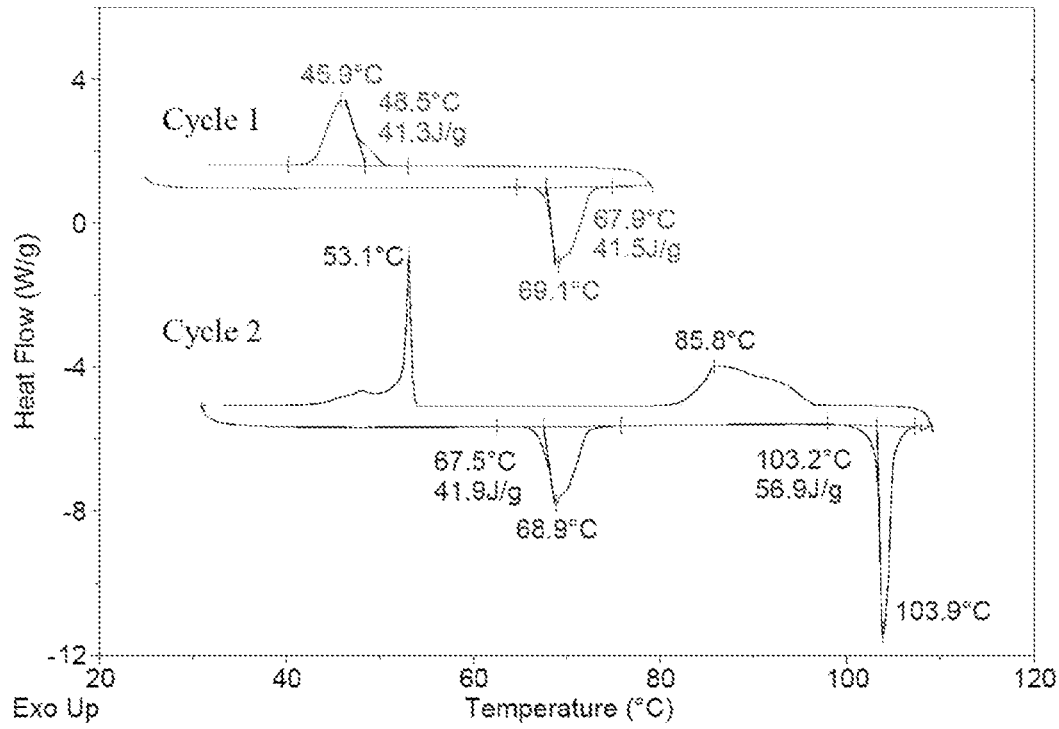
FIG. 4 depicts cyclic DSC data for heptadecan-9-yl 8-((2-hydroxyethyl)amino)octanoate 4-hydroxybenzoate Polymorph A, batch No. 2.
Figure 5:
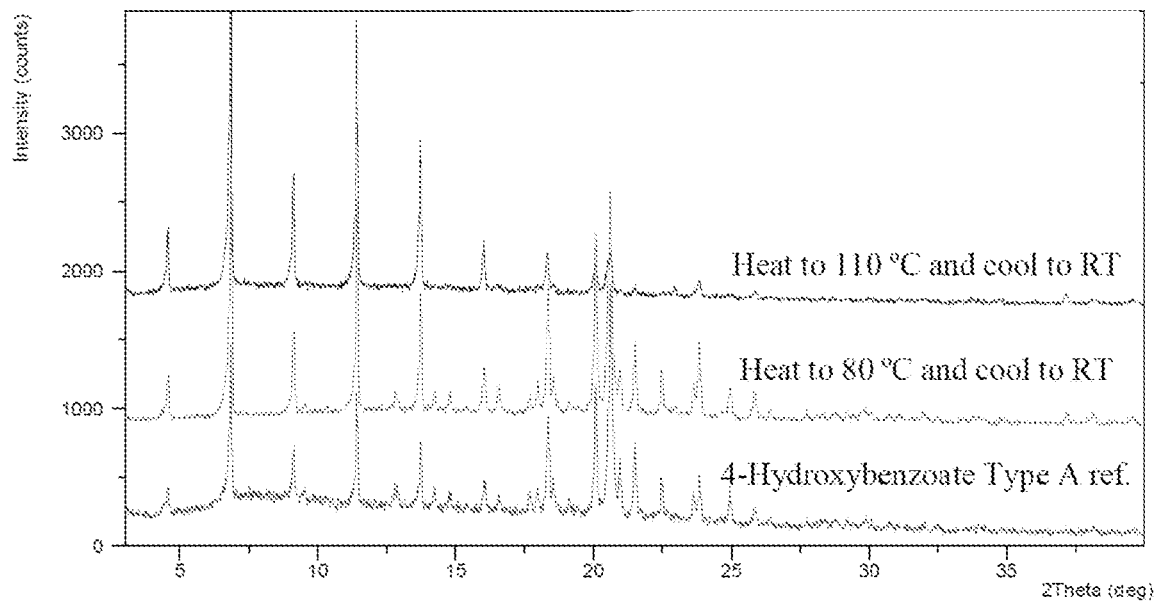
FIG. 5 depicts a representative XRPD pattern overlay of heptadecan-9-yl 8-((2-hydroxyethyl)amino)octanoate 4-hydroxybenzoate Polymorph A (i.e., Type A in the figure), batch No. 2, before and after heating.
Figure 6:
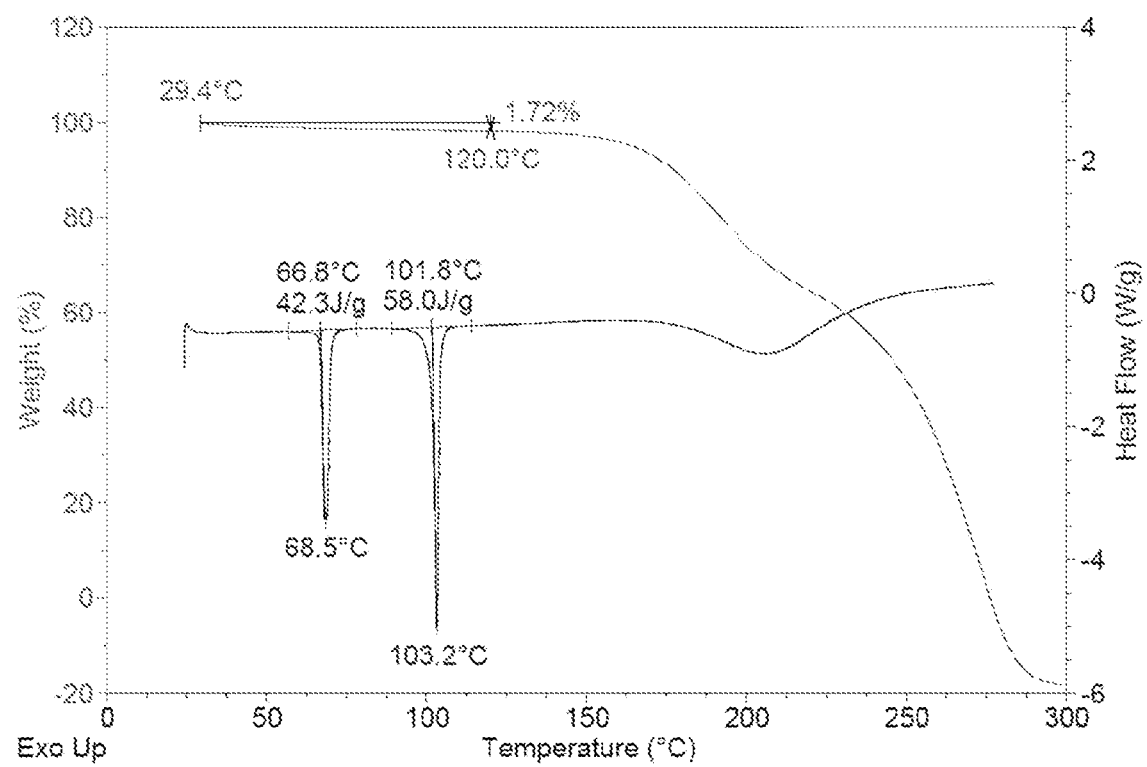
FIG. 6 depicts TGA and DSC data for heptadecan-9-yl 8-((2-hydroxyethyl)amino)octanoate 4-hydroxybenzoate Polymorph A, batch No. 1.
Figure 7:
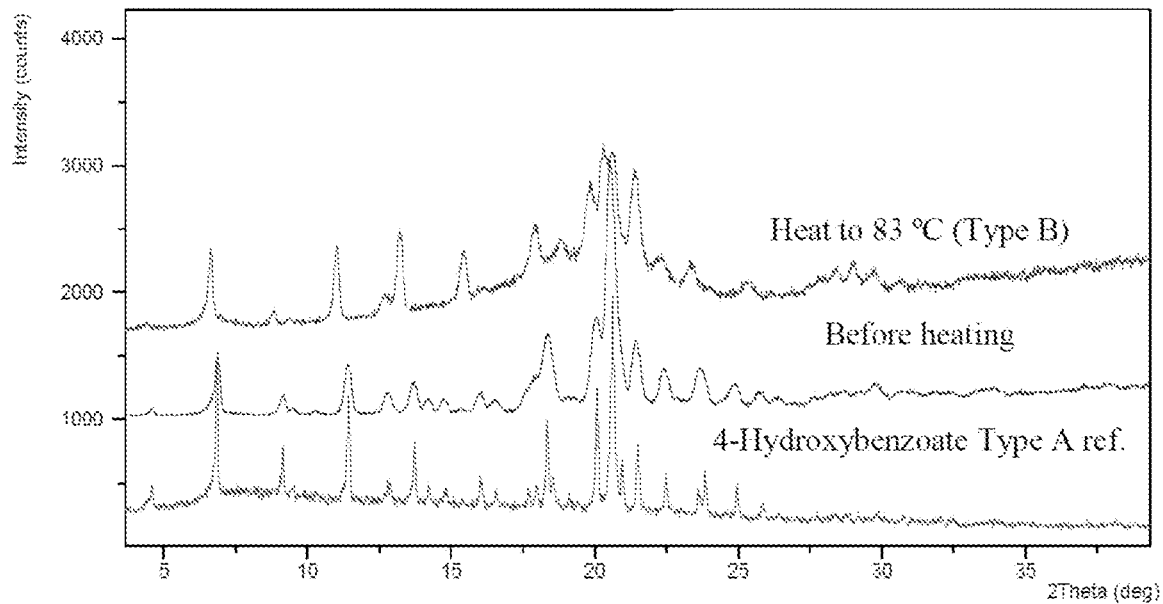
FIG. 7 depicts variable temperature X-ray powder diffraction (VT-XRPD) pattern overlay of heptadecan-9-yl 8-((2-hydroxyethyl)amino)octanoate 4-hydroxybenzoate Polymorph A batch No. 1, before and after heating. Type A ref. in this figure is heptadecan-9-yl 8-((2-hydroxyethyl)amino)octanoate 4-hydroxybenzoate Polymorph A, batch No. 2.

As evidenced by heating experiments in FIG. 5 and VT-XRPD results in FIGS. 6 and 7, form change (new form assigned as 4-hydroxybenzoate Polymorph B) was observed after heating sample (batch No. 1) to 83° C. (over the first endotherm in DSC) in VT-XRPD test and no form change was observed after heating sample (batch No. 2) over the first endotherm and cooling back to RT. Considering results of heating experiments and thermal signals in cyclic DSC (FIG. 4), 4-hydroxybenzoate Polymorphs A and B are possibly enantiotropically related and Polymorph A is more stable at lower temperature (RT).

Figure 8:
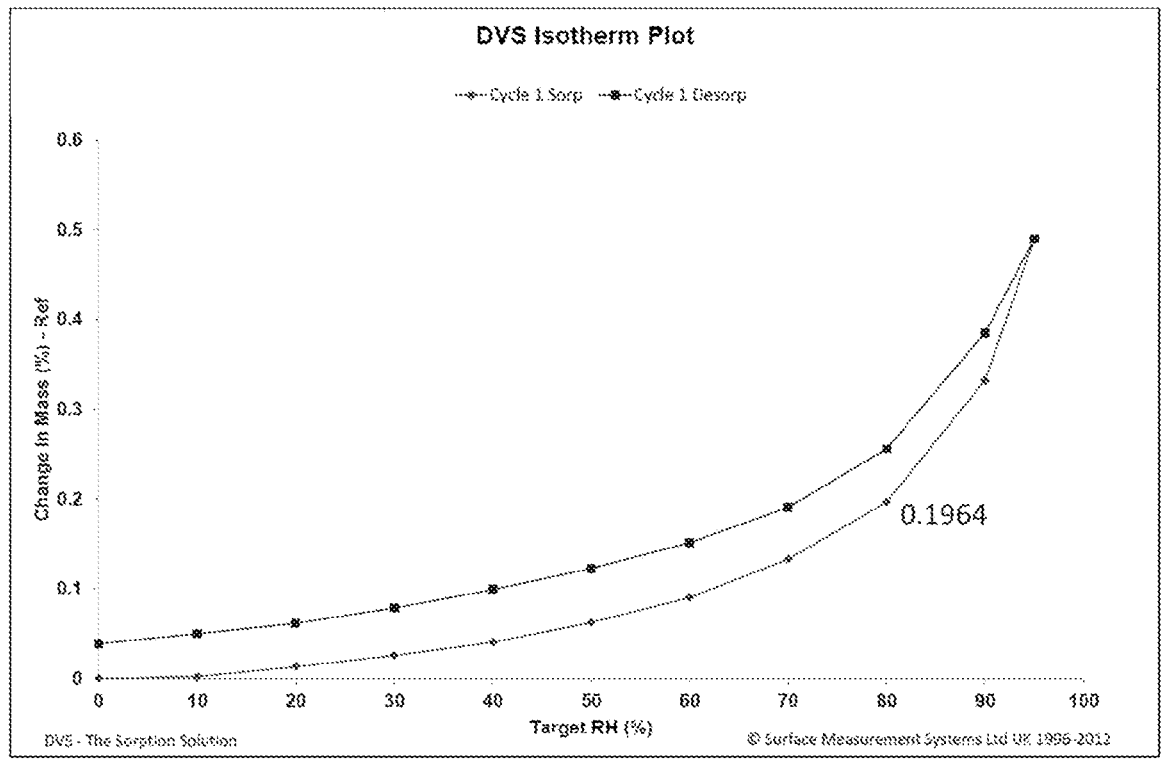
FIG. 8 depicts dynamic vapor sorption (DVS) data at 25° C. for heptadecan-9-yl 8-((2-hydroxyethyl)amino)octanoate 4-hydroxybenzoate Polymorph A, batch No. 1.
Figure 9:
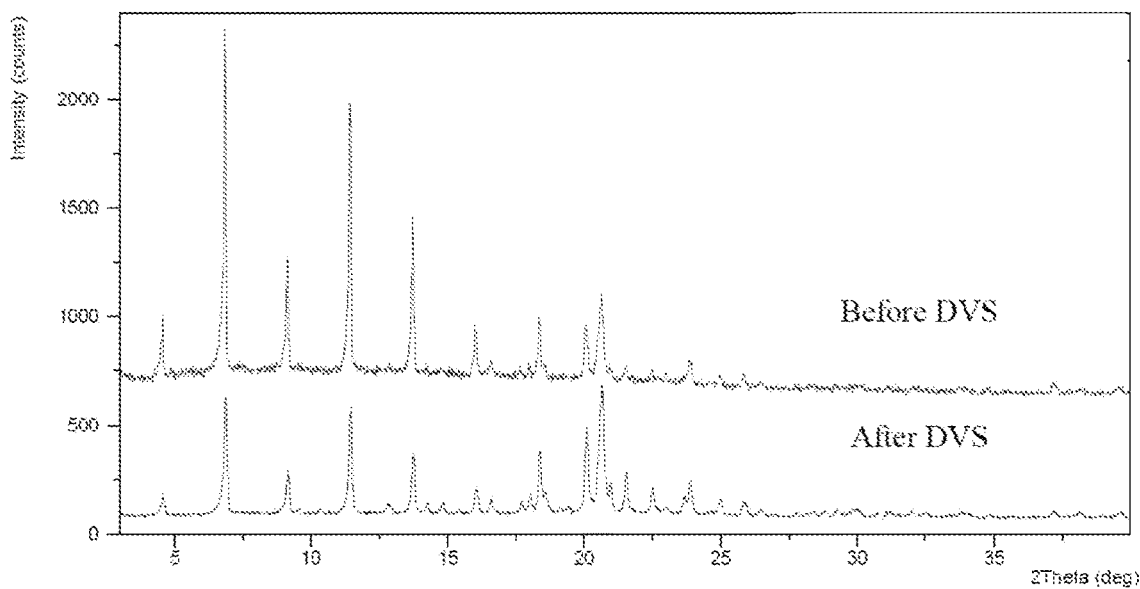
FIG. 9 depicts an XRPD pattern overlay of heptadecan-9-yl 8-((2-hydroxyethyl)amino)octanoate 4-hydroxybenzoate Polymorph A, batch No. 1, before and after DVS.
Figure 10:
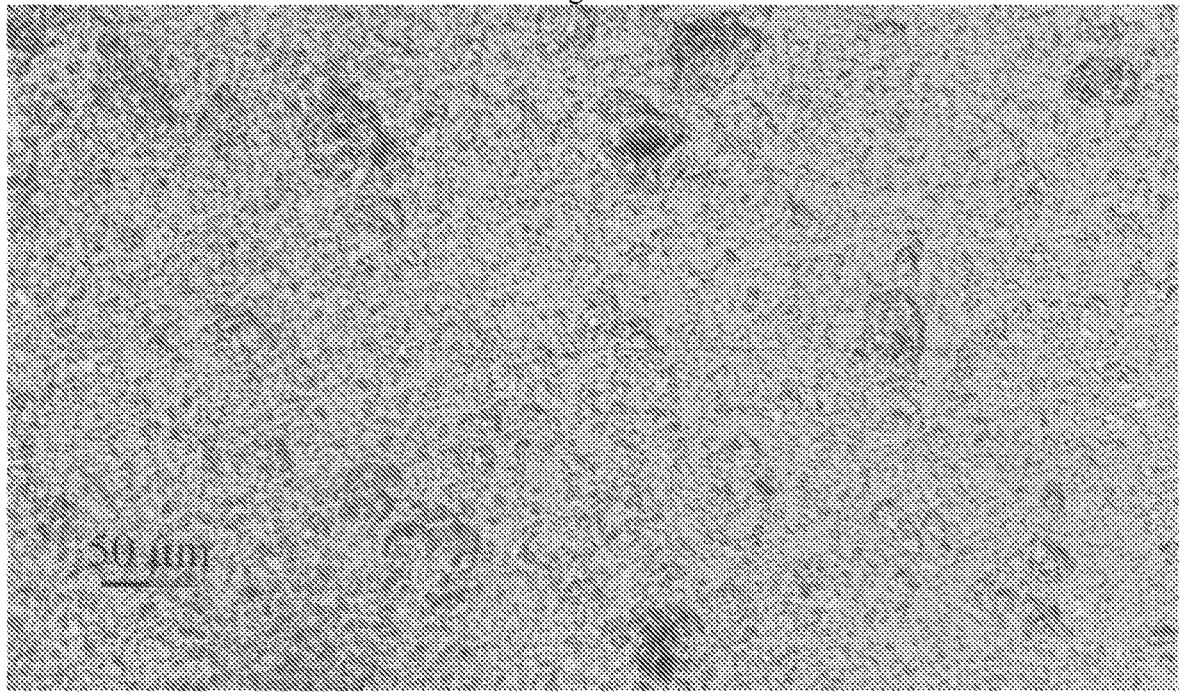
FIG. 10 depicts a polarized light microscopy (PLM) image for heptadecan-9-yl 8-((2-hydroxyethyl)amino)octanoate 4-hydroxybenzoate Polymorph A, batch No. 1.

Further evaluation on hygroscopicity of 4-hydroxybenzoate Polymorph A was conducted via DVS isotherm collection at 25° C. Results in FIGS. 8 and 9 showed that sample (batch No. 1) is non-hygroscopic with no form change before and after DVS test. Moreover, sample (batch No. 1) showed aggregation of small particles (<10 μm) in PLM image (FIG. 10) and a purity of 99.96 area % determined by HPLC (Table 3).

TABLE 3

| # Peak | Time (min) | RRT | Area (mAU*S) | Area (%) |
|---|---|---|---|---|
| 1 | 16.58 | 1.00 | 2070.9 | 99.96 |
| 2 | 16.99 | 1.02 | 0.8 | 0.04 |

Characterization of Trimellitate

Figure 11:
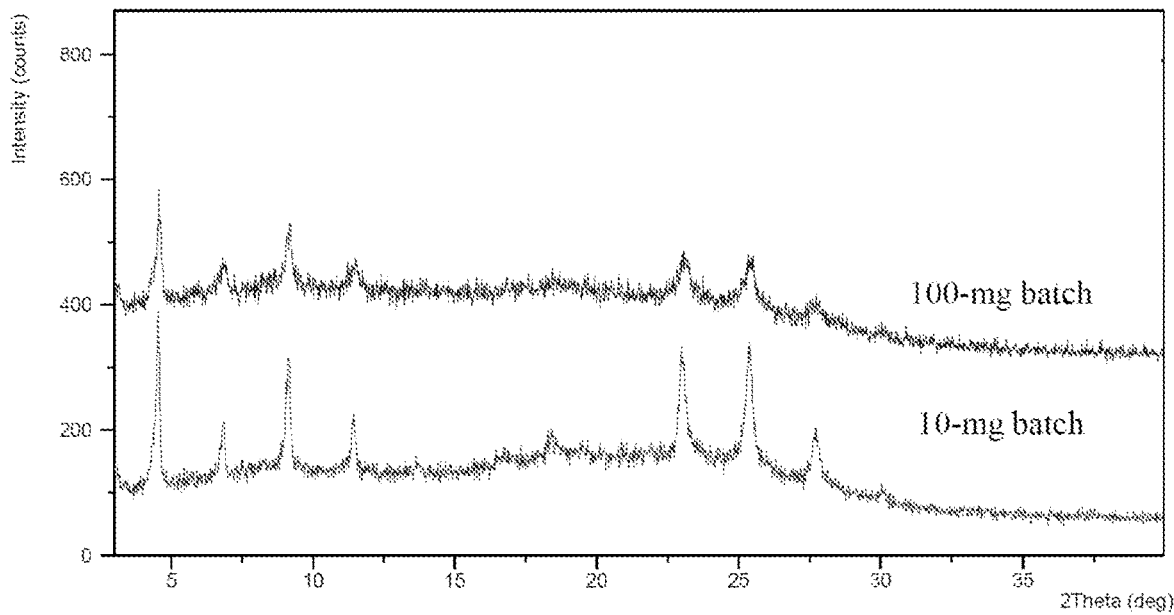
FIG. 11 depicts a representative XRPD pattern overlay of heptadecan-9-yl 8-((2-hydroxyethyl)amino)octanoate trimellitate Polymorph A batches, i.e., 100 mg and 10 mg batches or batches Nos. 1 and 2.
Figure 12:
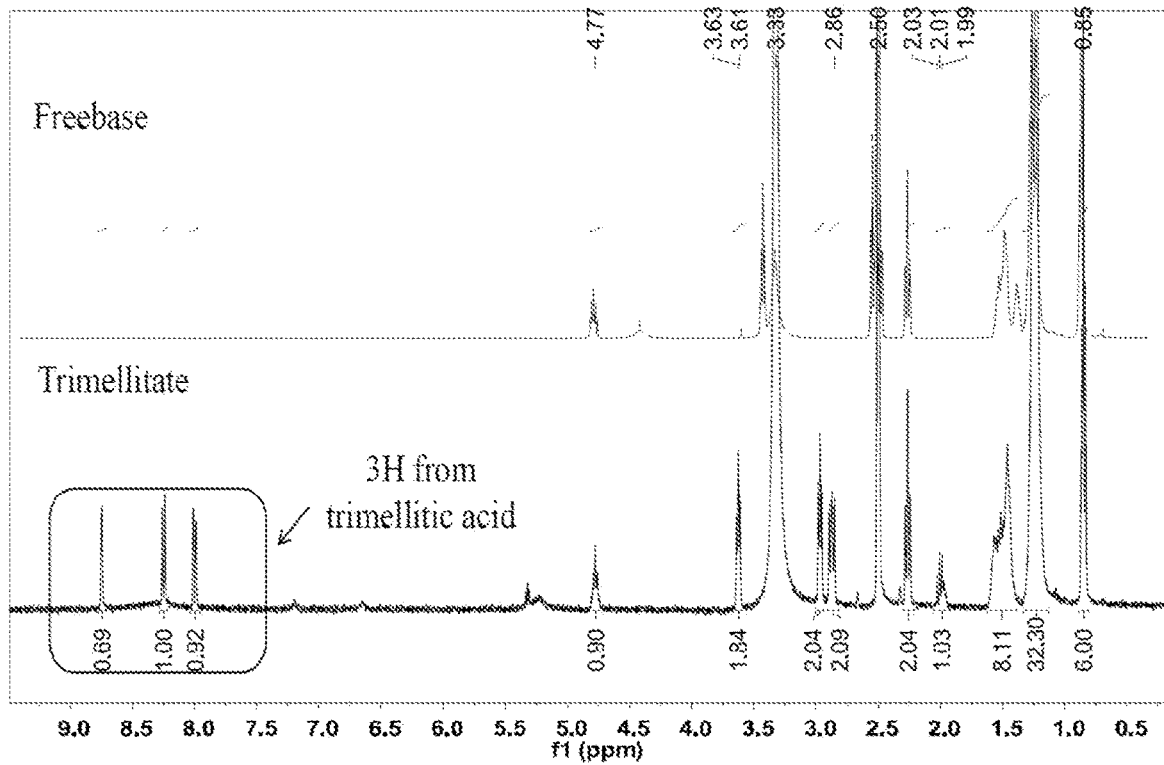
FIG. 12 depicts an $^1$H NMR spectrum of heptadecan-9-yl 8-((2-hydroxyethyl)amino)octanoate trimellitate Polymorph A, batch No. 2.

Trimellitate Polymorph A samples (batch Nos. 1 and 2) were prepared by reactive crystallization in EtOAc with XRPD patterns shown in FIG. 11. The $^1$H NMR spectrum was collected for sample (batch No. 2) and is shown in FIG. 12. Compared to freebase, a certain amount of trimellitic acid was detected (signals between 8.0 and 9.0 ppm), indicating the salt formation.

Figure 13:
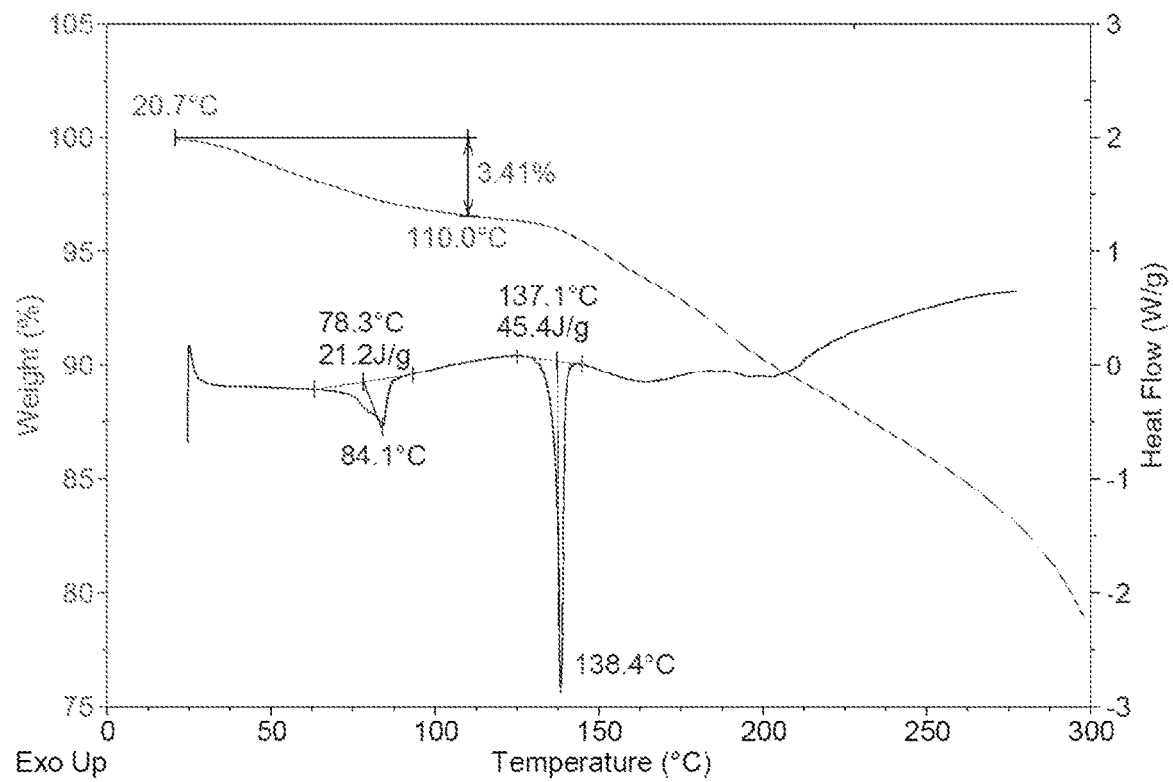
FIG. 13 depicts TGA and DSC data for heptadecan-9-yl 8-((2-hydroxyethyl)amino)octanoate trimellitate Polymorph A, batch No. 1.
Figure 14:
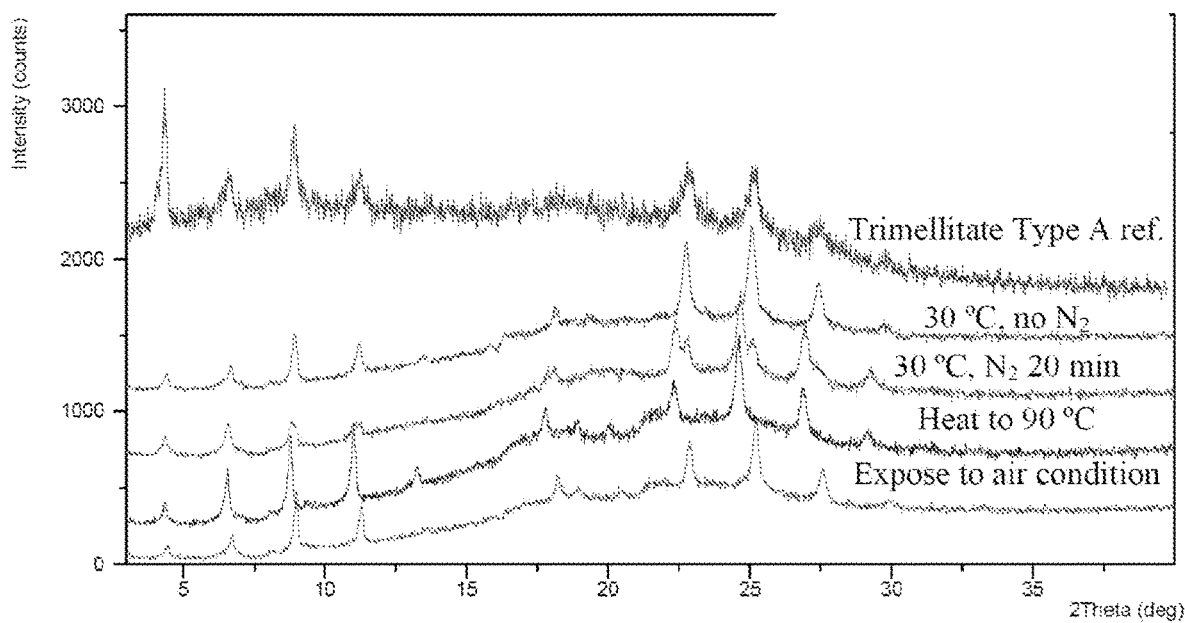
FIG. 14 depicts a VT-XRPD pattern overlay of heptadecan-9-yl 8-((2-hydroxyethyl)amino)octanoate trimellitate Polymorph A batch No. 1, before and after heating.

As per the TGA and DSC data in FIG. 13, sample (batch No. 1) showed a weight loss of 3.4% up to 110° C. and two endothermic peaks at 78.3° C. and 137.1° C. (onset temperature) before decomposition. As demonstrated by VT-XRPD results in FIG. 14, extra diffraction peaks appeared after 20 minutes of $N_2$ flow, and new form was observed at 90° C., which converted back to trimellitate Polymorph A after being heated and exposed to ambient condition, suggesting that Polymorph A is a hydrated form.

Figure 15:
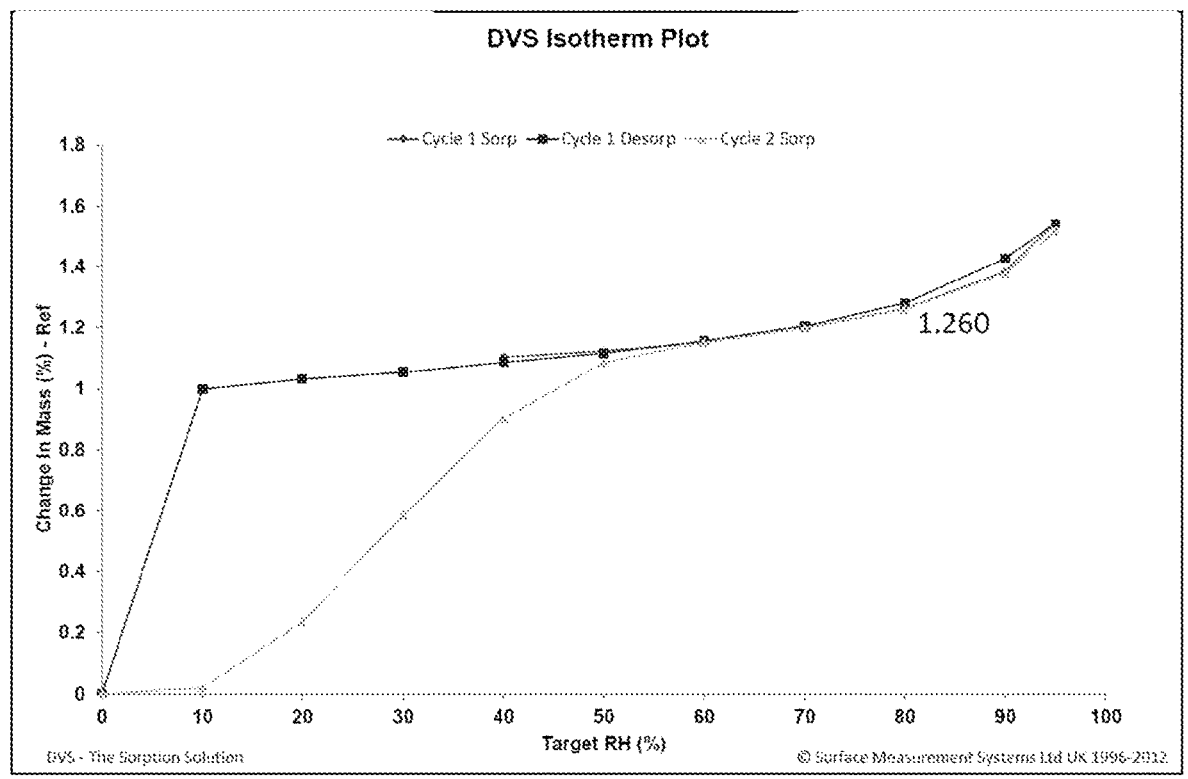
FIG. 15 depicts DVS data at 25° C. for heptadecan-9-yl 8-((2-hydroxyethyl)amino)octanoate trimellitate Polymorph A, batch No. 1.
Figure 16:
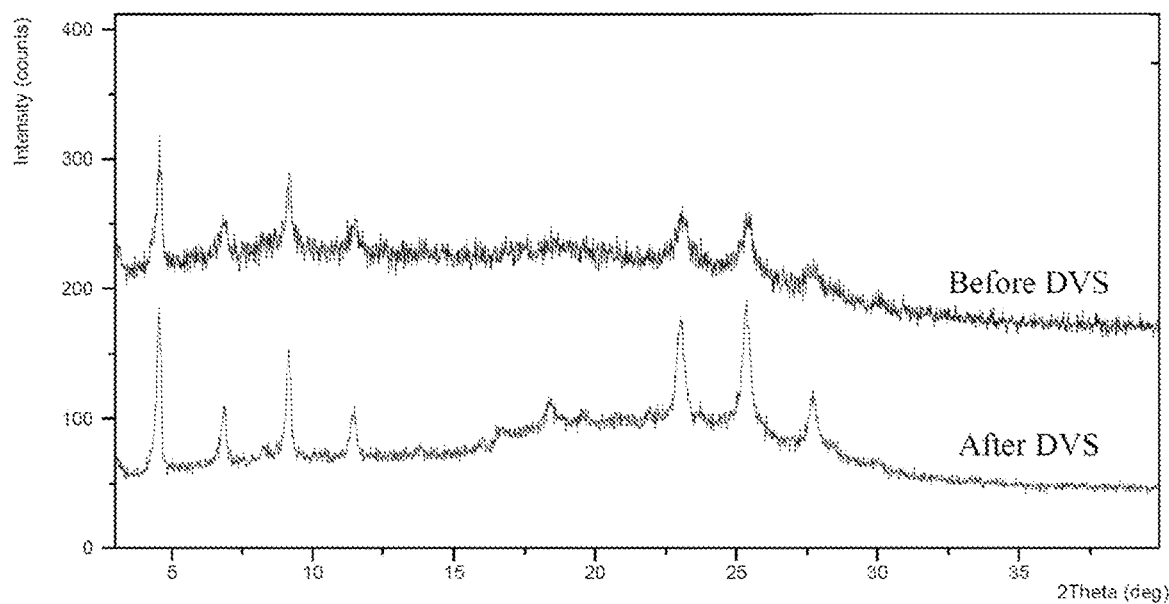
FIG. 16 depicts an XRPD pattern overlay of heptadecan-9-yl 8-((2-hydroxyethyl)amino)octanoate trimellitate Polymorph A, batch No. 1, before and after DVS.
Figure 17:
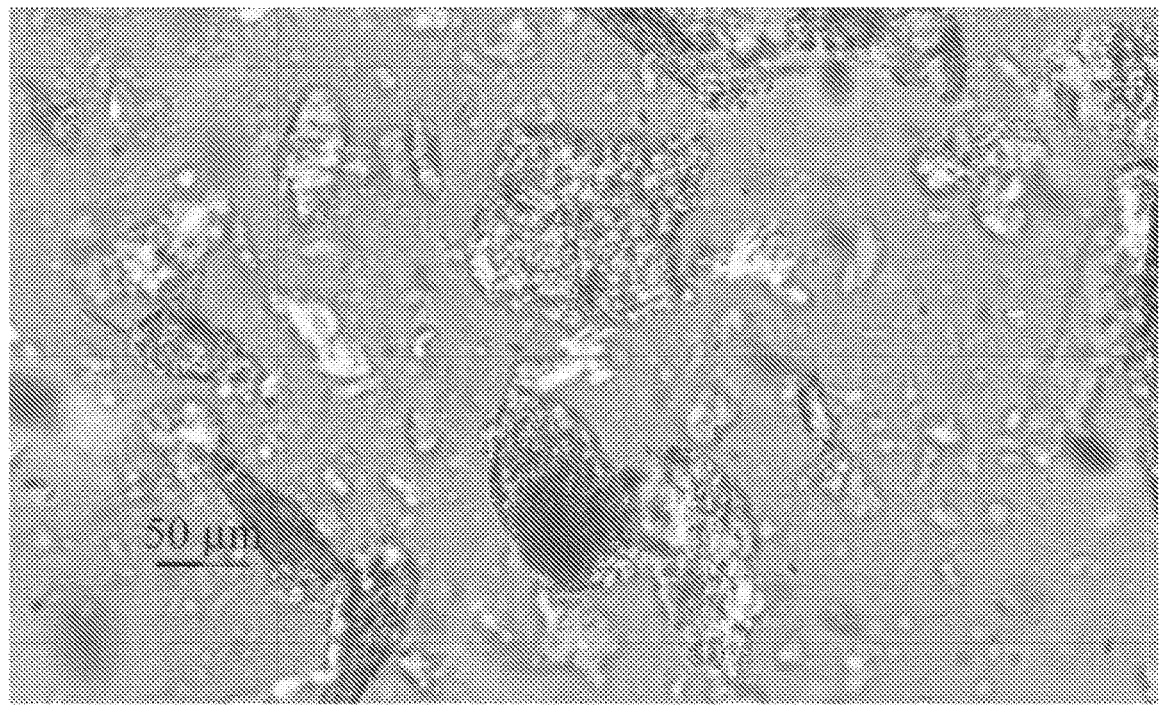
FIG. 17 depicts a polarized light microscopy (PLM) image for heptadecan-9-yl 8-((2-hydroxyethyl)amino)octanoate trimellitate Polymorph A, batch No. 1.

Further evaluation on hygroscopicity of trimellitate Polymorph A was performed via DVS isotherm collection at 25° C. Results in FIGS. 15 and 16 showed that sample (batch No. 1) is slightly hygroscopic with no form change before and after DVS test. Platform observed in DVS plot (FIG. 15) also indicated that Polymorph A is a hydrated form. Moreover, sample (batch No. 1) showed irregular particles (<10 μm) in PLM image (FIG. 17) and a purity of 99.97 area % determined by HPLC (Table 4).

TABLE 4

| # Peak | Time (min) | RRT | Area (mAU*S) | Area (%) |
|---|---|---|---|---|
| 1 | 16.62 | 1.00 | 1404.2 | 99.97 |
| 2 | 16.99 | 1.02 | 0.5 | 0.03 |

Characterization of Orotate

Figure 18:
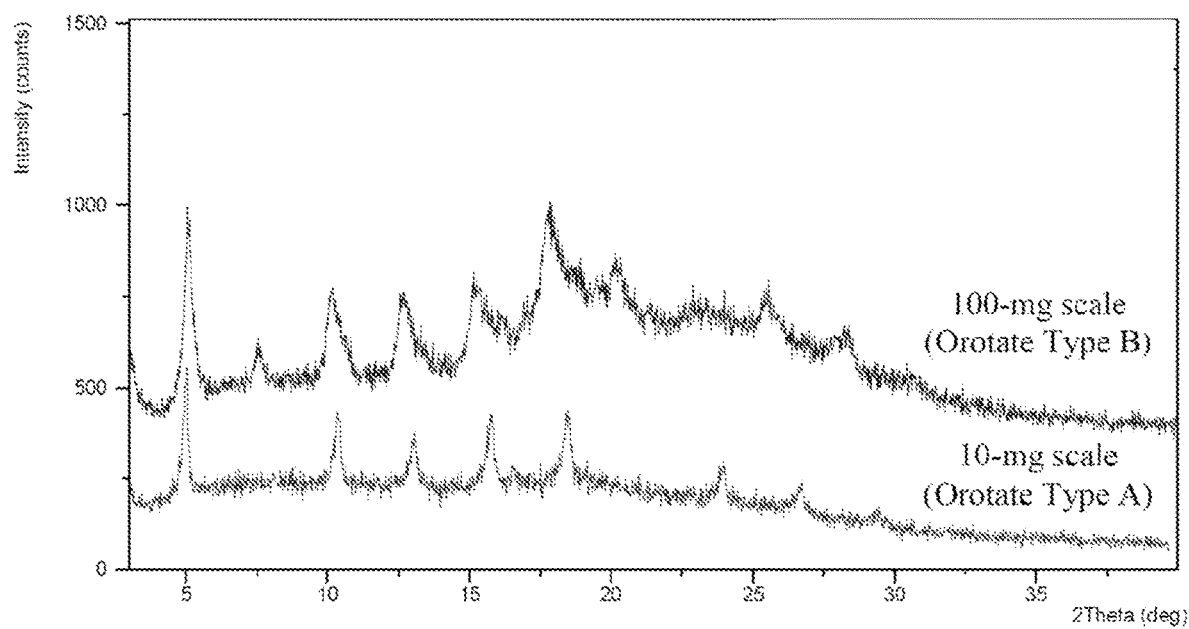
FIG. 18 depicts a representative XRPD pattern overlay of heptadecan-9-yl 8-((2-hydroxyethyl)amino)octanoate orotate Polymorphs A and B.
Figure 19:
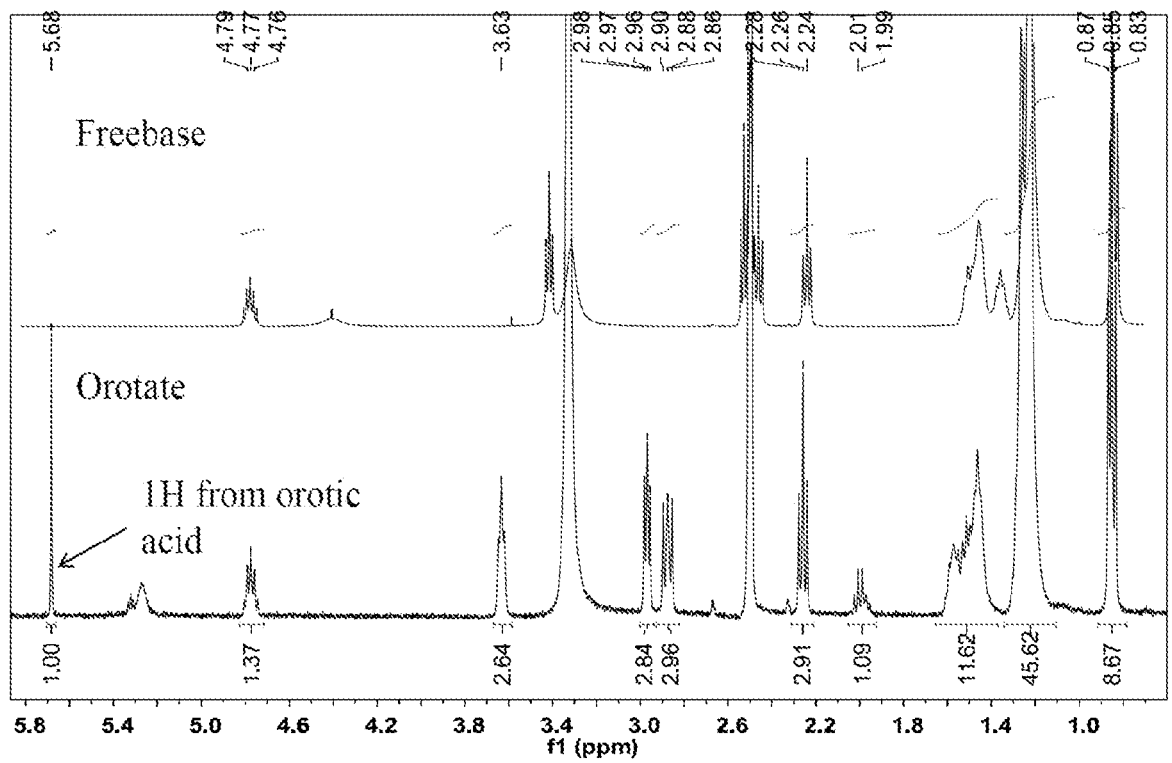
FIG. 19 depicts an $^1$H NMR spectrum of heptadecan-9-yl 8-((2-hydroxyethyl)amino)octanoate orotate Polymorph A.

Orotate Polymorph A and Polymorph B were generated via reactive crystallization in EtOAc with XRPD patterns shown in FIG. 18. The $^1$H NMR spectrum of Polymorph A was collected and is shown in FIG. 19. In addition to freebase, a certain amount of orotic acid was detected (signal at 5.7 ppm).

Figure 20:
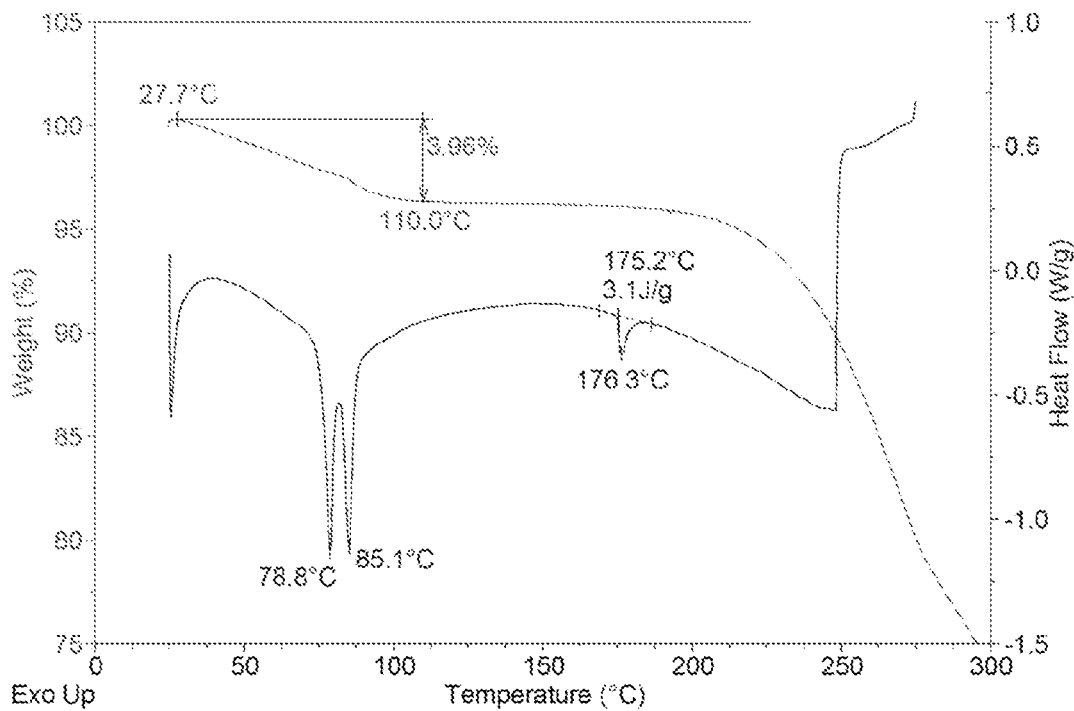
FIG. 20 depicts TGA and DSC data for heptadecan-9-yl 8-((2-hydroxyethyl)amino)octanoate orotate Polymorph A.
Figure 21:
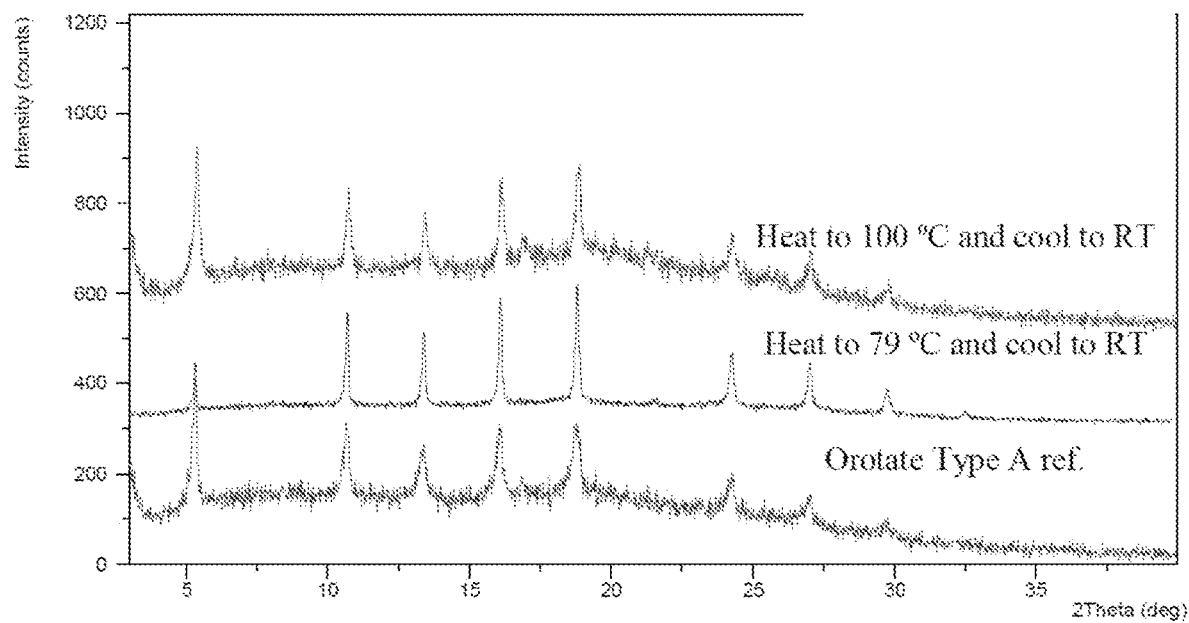
FIG. 21 depicts a VT-XRPD pattern overlay of heptadecan-9-yl 8-((2-hydroxyethyl)amino)octanoate orotate Polymorph A, before and after heating.
Figure 22:
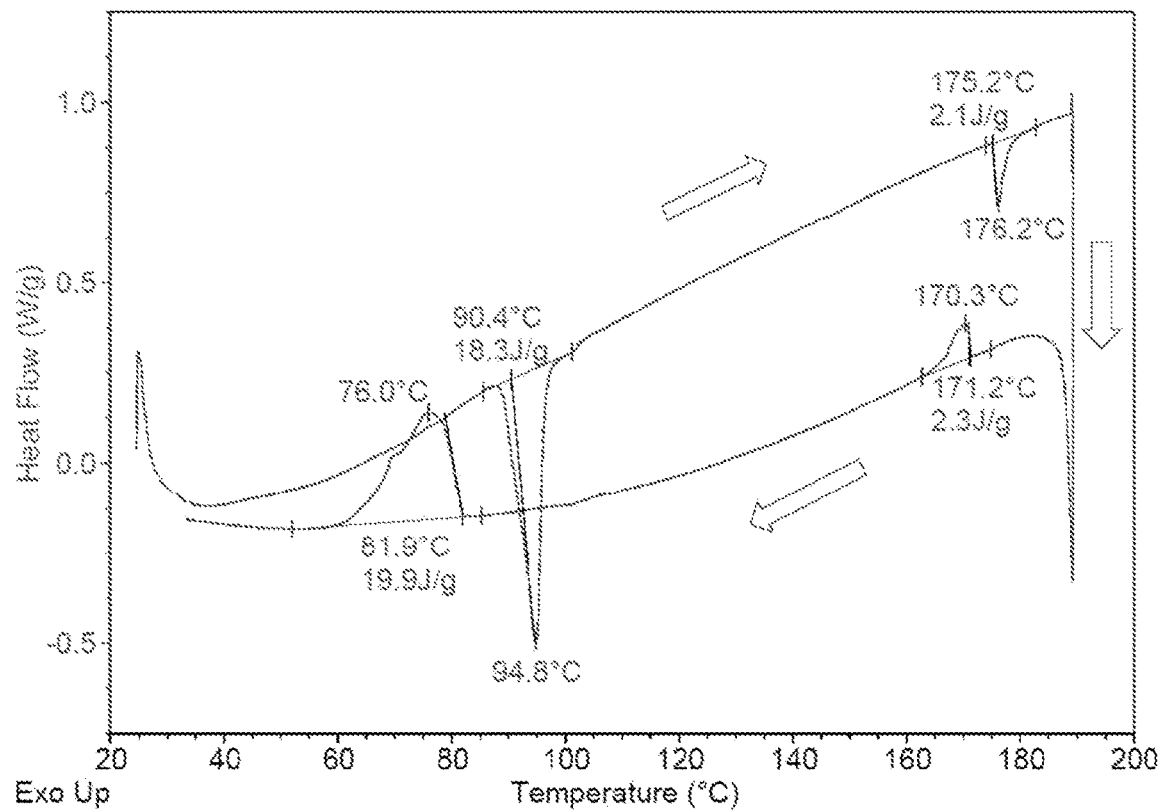
FIG. 22 depicts heating-cooling DSC curve for heptadecan-9-yl 8-((2-hydroxyethyl)amino)octanoate orotate Polymorph A.

As per the TGA and DSC data in FIG. 20, Polymorph A sample showed a weight loss of 4.0% up to 110° C. and endothermic peaks at 78.8, 85.1 and 176.3° C. (peak temperature) before decomposition. Results of heating experiments in FIG. 21 showed that no form change was observed after heating Polymorph A sample over the first two endothermic signals and cooling back to RT, suggesting Polymorph A is anhydrous or a hydrated form which can rapidly absorb water at ambient conditions after de-hydration. In addition, as evidenced by the heating-cooling DSC curve of Polymorph A in FIG. 22, endothermic and exothermic signals with similar enthalpy were observed at 170~175° C. and 80~90° C., suggesting the possible form transition and the existence of anhydrate form at higher temperature.

Figure 23:
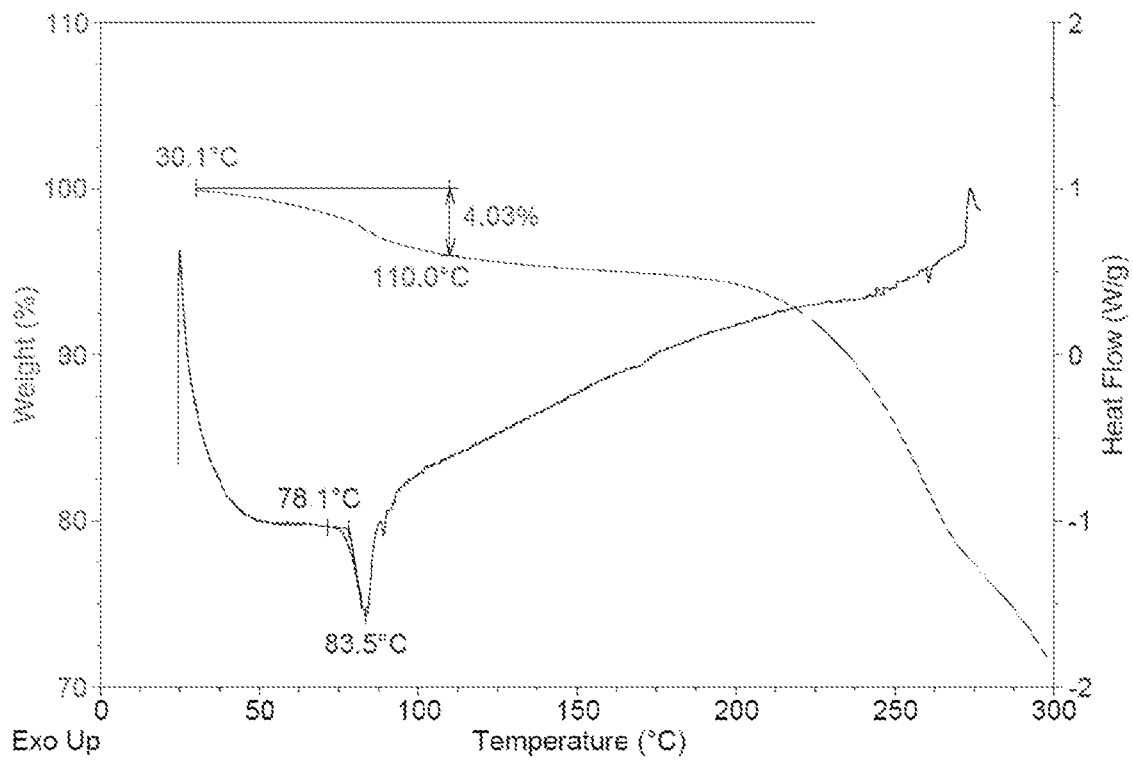
FIG. 23 depicts TGA and DSC data for heptadecan-9-yl 8-((2-hydroxyethyl)amino)octanoate orotate Polymorphs B.
Figure 24:
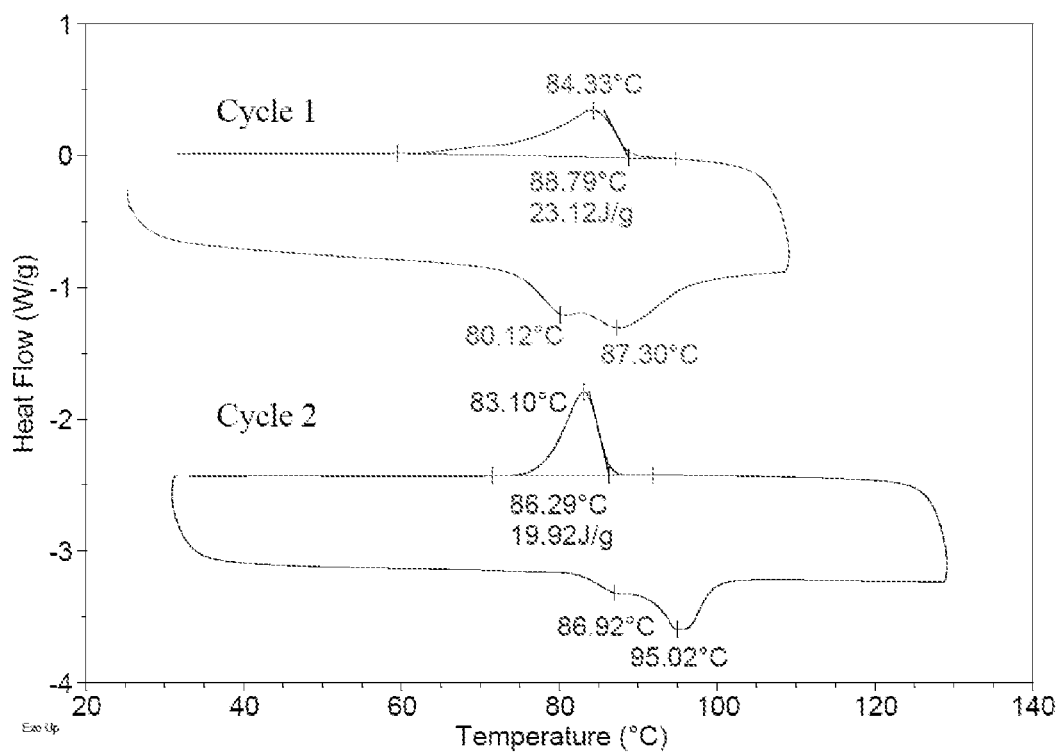
FIG. 24 depicts cyclic DSC data for heptadecan-9-yl 8-((2-hydroxyethyl)amino)octanoate orotate Polymorphs B.
Figure 25:
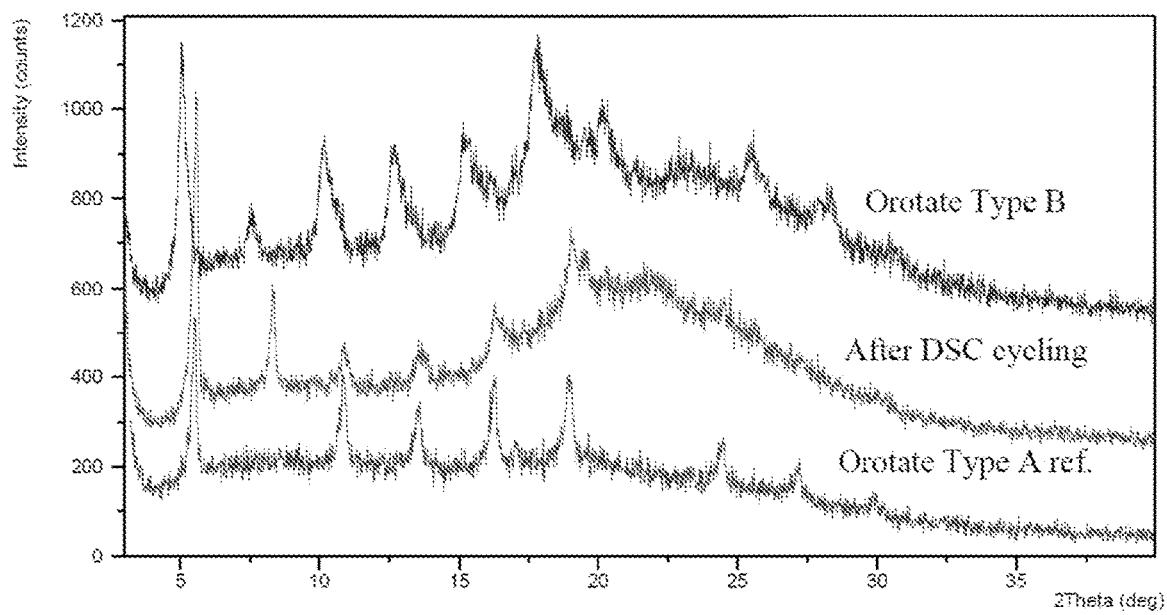
FIG. 25 depicts an XRPD pattern overlay of heptadecan-9-yl 8-((2-hydroxyethyl)amino)octanoate orotate Polymorph B, before and after cyclic DSC.
Figure 26:
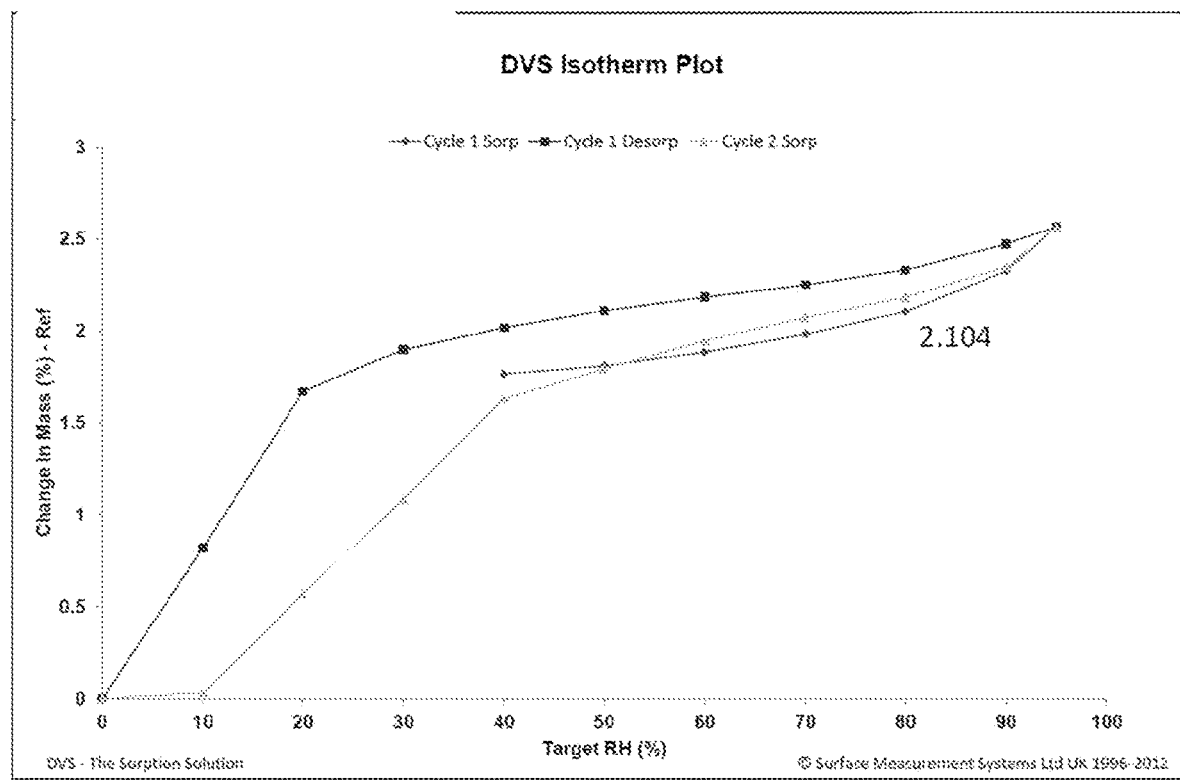
FIG. 26 depicts DVS data at 25° C. for heptadecan-9-yl 8-((2-hydroxyethyl)amino)octanoate orotate Polymorphs B.
Figure 27:
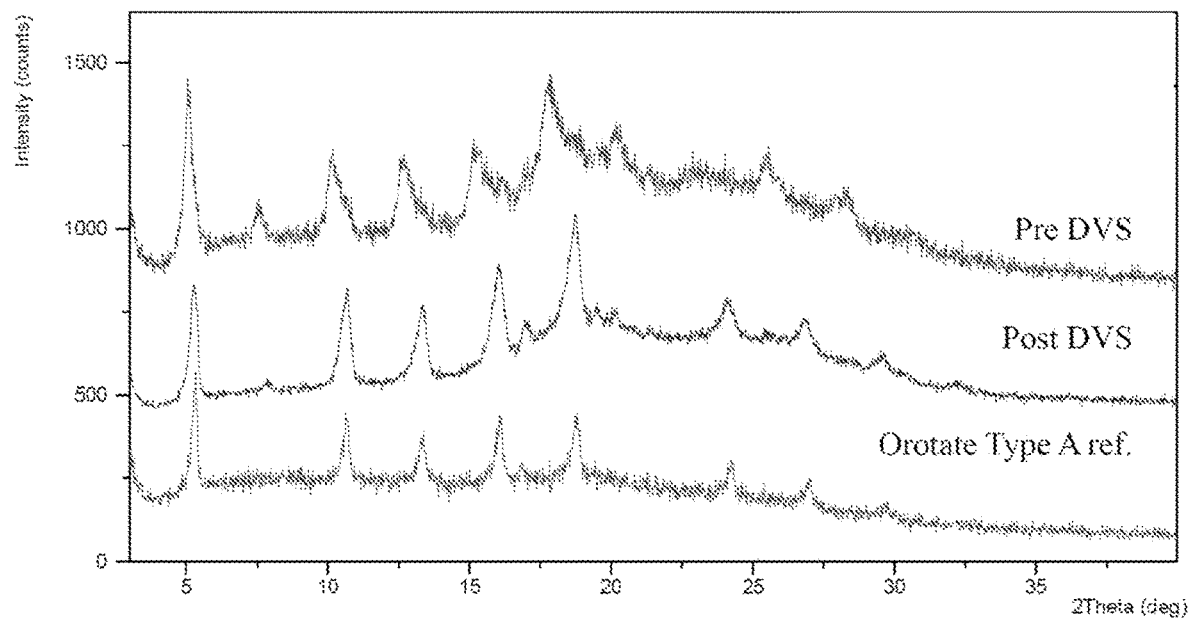
FIG. 27 depicts an XRPD pattern overlay of heptadecan-9-yl 8-((2-hydroxyethyl)amino)octanoate orotate Polymorph B, before and after DVS.
Figure 28:
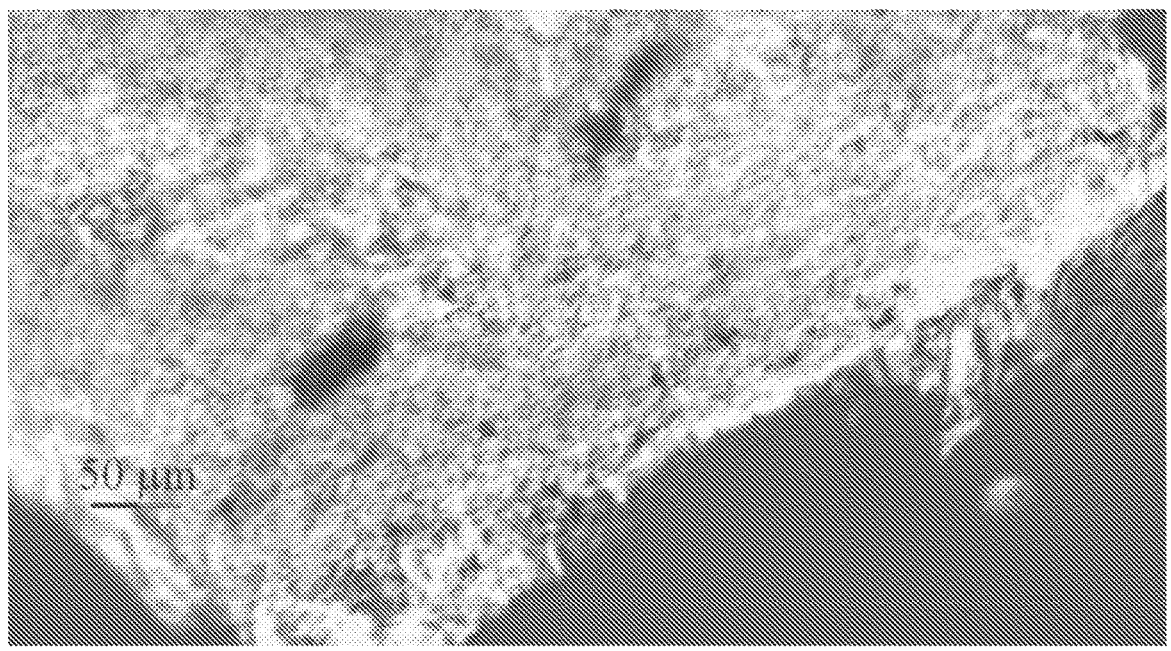
FIG. 28 depicts a PLM image of heptadecan-9-yl 8-((2-hydroxyethyl)amino)octanoate orotate Polymorph B.

TGA and DSC data of Polymorph B in FIG. 23 showed a weight loss of 4.0% up to 110° C. and endothermic peak at 78.1° C. (onset) before decomposition. After cyclic DSC between 25° C. and 130° C., Polymorph B converted to Polymorph A with data illustrated in FIG. 24 and FIG. 25, indicating Polymorph B is a hydrated or solvate form. DVS test of Polymorph B sample showed that it is slightly hygroscopic and converted to Polymorph A after DVS test, with data displayed in FIG. 26 and FIG. 27. Also, Polymorph B sample showed irregular particles in PLM image (FIG. 28) and a purity of 99.97 area % detected by HPLC (Table 5).

TABLE 5

| # Peak | Time (min) | RRT | Area (mAU*S) | Area (%) |
|---|---|---|---|---|
| 1 | 16.62 | 1.00 | 1464.2 | 99.97 |
| 2 | 17.00 | 1.02 | 0.5 | 0.03 |

Characterization of Sulfate

Figure 29:
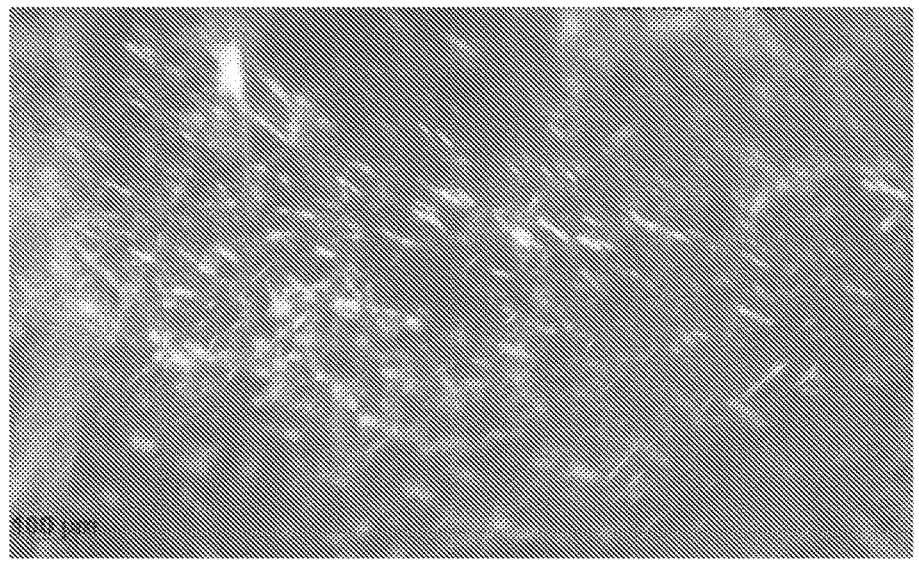
FIG. 29 depicts a PLM image of heptadecan-9-yl 8-((2-hydroxyethyl)amino)octanoate sulfate Polymorph A.
Figure 30:
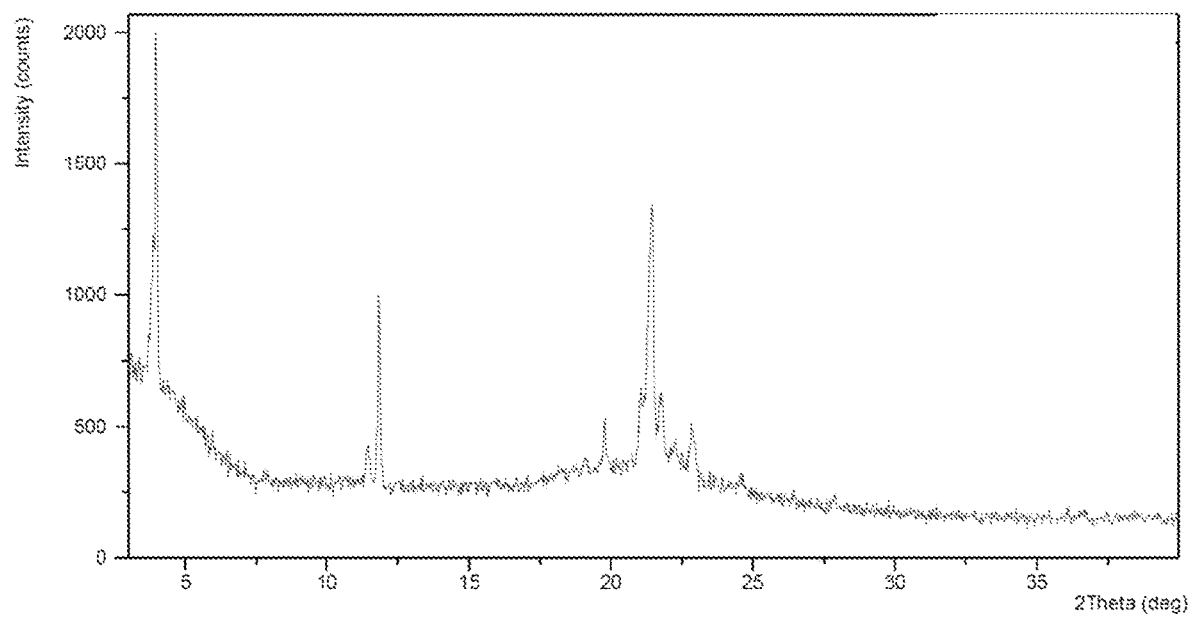
FIG. 30 depicts an XRPD pattern of heptadecan-9-yl 8-((2-hydroxyethyl)amino)octanoate sulfate Polymorph A.
Figure 31:
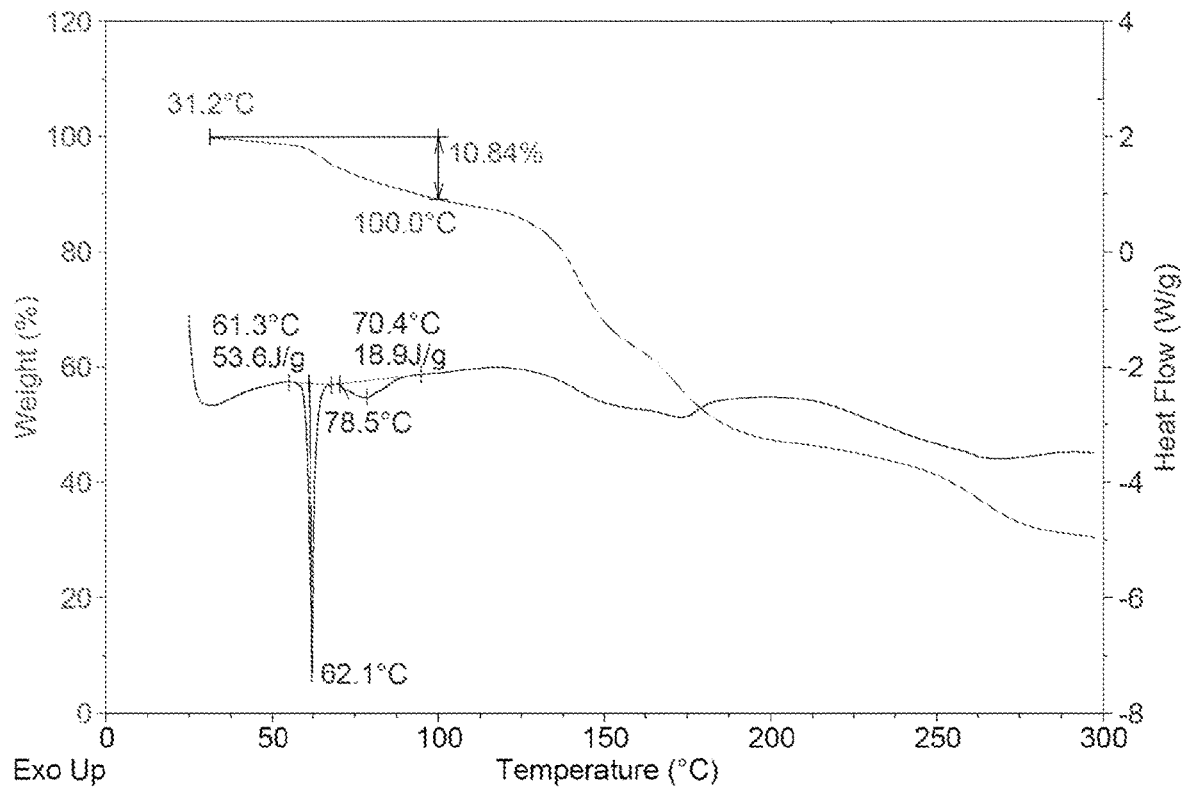
FIG. 31 depicts TGA and DSC data of heptadecan-9-yl 8-((2-hydroxyethyl)amino)octanoate sulfate Polymorph A.

Sulfate Polymorph A was generated by slow evaporation at 5° C. in n-heptane. Needle like crystals were observed during evaporation (FIG. 29), which was further isolated for XRPD, TGA and DSC tests. Results in FIGS. 30 and 31 showed that the sample is crystalline with continuous weight loss and multiple endotherms.

Characterization of Trimesate

Figure 32:
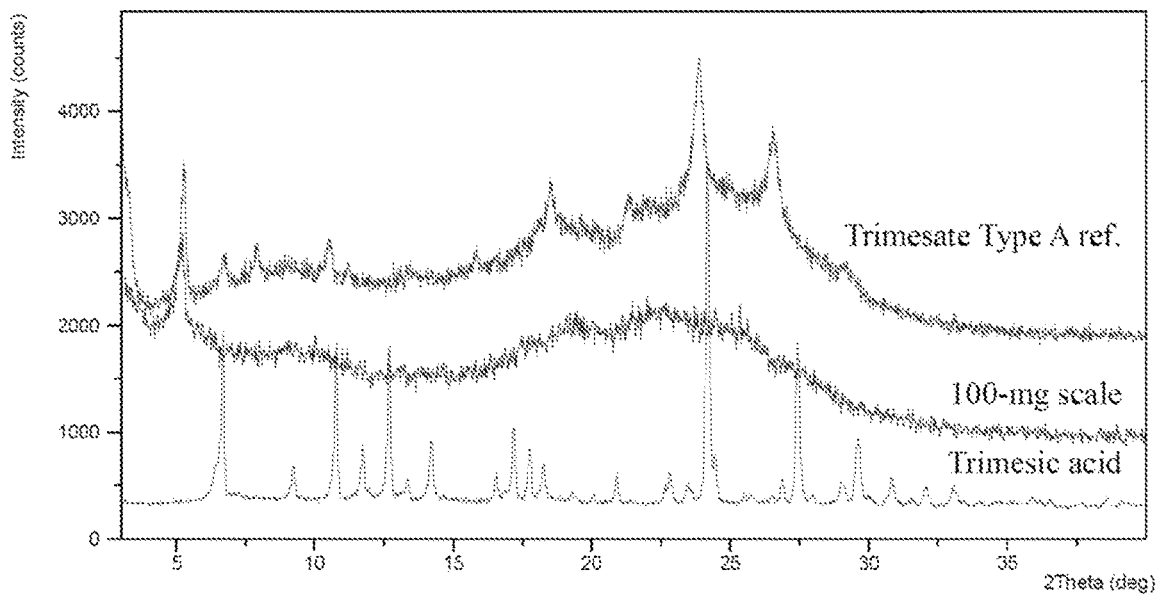
FIG. 32 depicts an XRPD pattern of heptadecan-9-yl 8-((2-hydroxyethyl)amino)octanoate trimesate Polymorph A.
Figure 33:
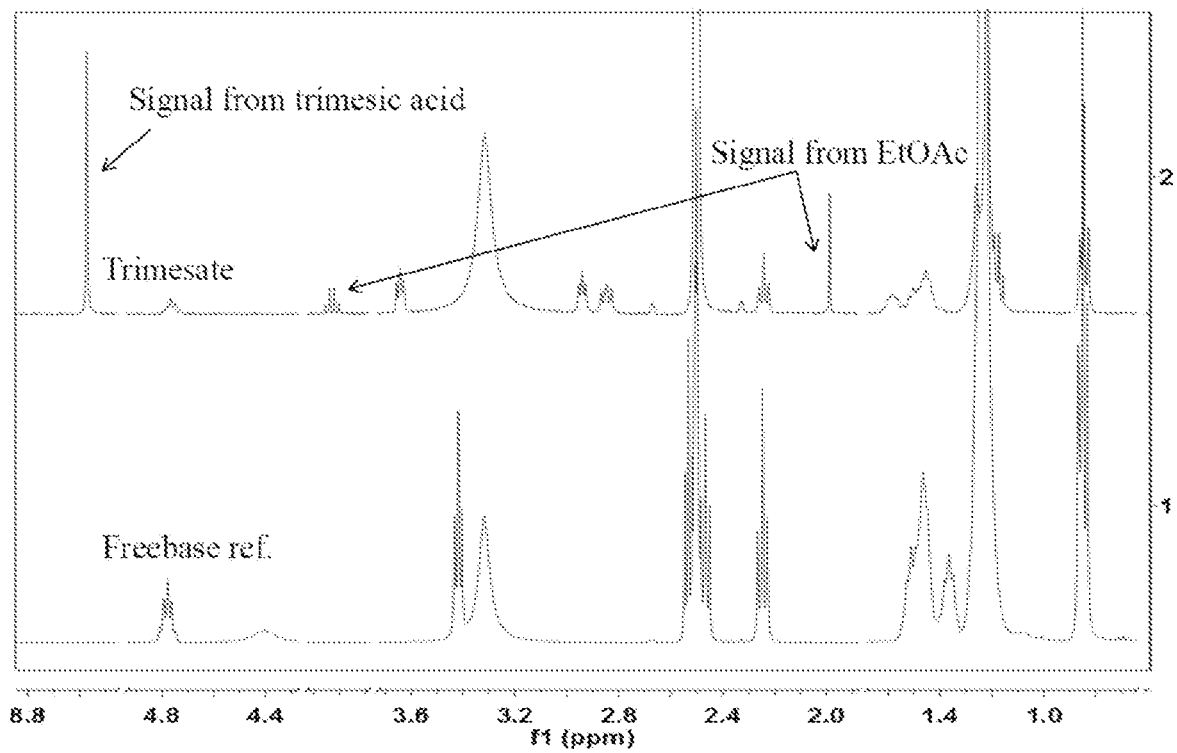
FIG. 33 depicts an $^1$H NMR overlay of heptadecan-9-yl 8-((2-hydroxyethyl)amino)octanoate trimesate and freebase.

Trimesate Polymorph A was generated from reactive crystallization in EtOAc system and XRPD pattern is shown in FIG. 32. $^1$H NMR results in FIG. 33 showed obvious signal of trimesic acid besides chemical shifts of freebase.

Characterization of Oxalate

Compound 1 Oxalate was generated from recrystallization. A purity of >97.5 area % detected by UPLC-CAD.

Example 2: Salts or Cocrystals of Compound 2

Preparation

Compound 2 freebase showed minor weight loss of 1.6% before reaching 200° C. in TGA. No obvious glass transition signal was observed and multiple endothermic peaks were observed with temperature elevated from −60 to 35° C. Two endothermic signals at −47.7 and −34.0° C. (onset) were observed during temperature elevated from −60 to 35° C.

Similar to the process described in Example 1, to identify a crystalline salt form or cocrystal of Compound 2, screening was performed under 93 conditions using 31 acids and three solvent systems. 0.3 mL stock solutions of Compound 2 freebase (~50 mg/mL) was dispersed in selected solvent and corresponding salt former was added with a molar charge ratio of 1:1. The mixtures of freebase and the coformer compound (e.g., an acid) were first transferred to temperature cycling from 50° C. to 5° C. for three cycles (heating rate of 4.5° C./min, cooling rate of 0.1° C./min) and then stored at 5° C. before analysis. If the samples were still clear, they would be subjected to slow evaporation at 5° C. to dryness. Resulted solids were isolated and analyzed.

Isolated crystal solids were characterized by X-ray powder diffraction (XRPD), thermo-gravimetric analysis (TGA) and differential scanning calorimetry (DSC), with proton nuclear magnetic resonance ($^1$H NMR) to confirm the freebase chemical structure and also potential co-existence with some organic acids. Exemplary data from the initial findings are summarized in Table 6.

TABLE 6

| | | Solvent | | |
|---|---|---|---|---|
| # | Acid | n-Heptane | Cyclohexane | EtOAc |
| 1 | Trimesic acid | Trimesate Polymorph A | Trimesate Polymorph A | Gel |
| 2 | Trimellitic acid | Amorphous + acid | Amorphous | Gel |
| 3 | (−)-2,3-Dibenzoyl-L-tartaric acid | Dibenzoyl-L-tartrate Polymorph A | Dibenzoyl-L-tartrate Polymorph A* | Dibenzoyl-L-tartrate Polymorph A* |
| 4 | Fumaric acid | Amorphous + two peaks | Acid | Gel |
| 5 | Terephthalic acid | Acid | Acid | Gel |
| 6 | Phthalic acid | Gel | Gel | Gel |
| 7 | Isophthalic acid | Acid | Acid | Gel |
| 8 | Benzoic acid | Gel | Gel | Gel |
| 9 | Cinnamic acid | Gel | Gel | Gel |
| 10 | 4-Hydroxy benzoic acid | Amorphous | Gel | Gel |
| 11 | Salicylic acid | Gel | Gel | Gel |
| 12 | Adipic acid | Acid | Gel | Gel |
| 13 | Suberic acid | Acid | Acid | Gel |
| 14 | Sebacic acid | Gel | Acid | Acid |
| 15 | 4-Acetamido benzoic acid | 4-Acetamido benzoate Polymorph A + acid | Acid | Acid |
| 16 | S-(+)-Mandelic | Gel | Gel | Gel |
| 17 | Orotic acid | Gel | Acid | Acid |
| 18 | Hexanoic acid | Gel | Gel | Gel |
| 19 | Citric acid | Gel | Gel | Gel |
| 20 | Acetic acid | Gel | Gel | Gel |
| 21 | Succinic acid | Acid | Acid | Gel |
| 22 | Malonic acid | Gel | Gel | Gel |
| 23 | (+)-Camphor-10-sulfonic acid | Gel | Gel | Gel |
| 24 | Nicotinic acid | Acid | Acid | Acid |
| 25 | (+)-L-tartaric acid | L-Tartrate Polymorph A* | Gel | L-Tartrate Polymorph A* |
| 26 | Hydrochloric acid | Gel | Gel | Gel |
| 27 | Sulfuric acid | Gel | Gel | Gel |
| 28 | Phosphoric acid | Gel | Gel | Gel |
| 29 | Methanesulfonic acid | Mesylate Polymorph A* | Mesylate Polymorph A* | Gel |
| 30 | p-Toluene sulfonic acid | Gel | Gel | Gel |
| 31 | 2,5-Dihydroxybenzoic acid | Gel | Gel | Gel |

*solids obtained after 5° C. evaporation.

Characterization of Dibenzoyl-L-tartrate

Figure 36:
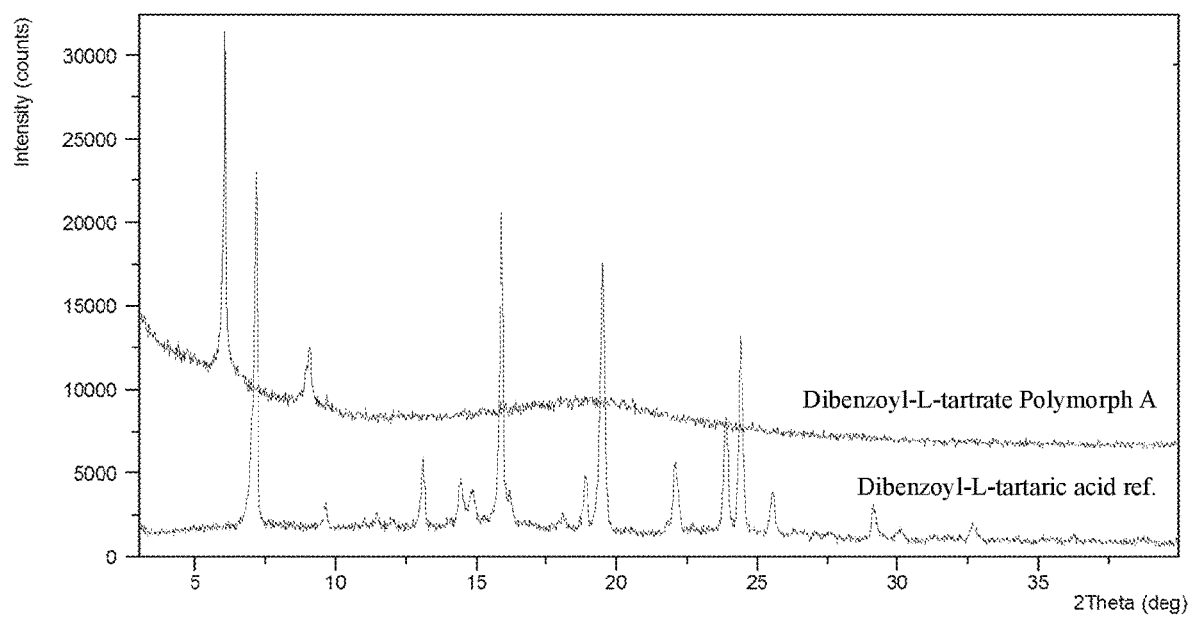
FIG. 36 depicts an XRPD pattern overlay of heptadecan-9-yl 8-((2-hydroxyethyl)(6-oxo-6-(undecyloxy)hexyl)amino)octanoate dibenzoyl-L-tartrate Polymorph A and the corresponding acid, dibenzoyl-L-tartaric acid.
Figure 37:
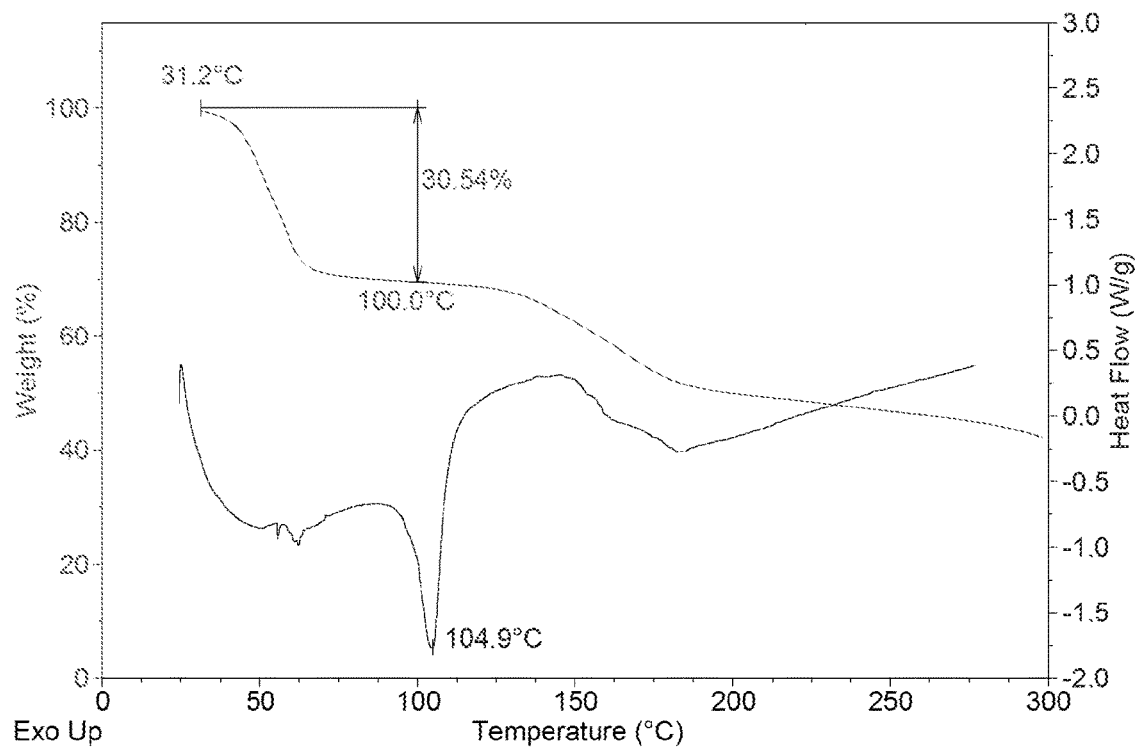
FIG. 37 depicts TGA and DSC data for heptadecan-9-yl 8-((2-hydroxyethyl)(6-oxo-6-(undecyloxy)hexyl)amino)octanoate dibenzoyl-L-tartrate Polymorph A.

Compound 2 dibenzoyl-L-tartrate Polymorph A was prepared by combining Compound 2 freebase with (−)-2,3-dibenzoyl-L-tartaric acid in n-heptane and showed crystallinity as characterized by XRPD in FIG. 36. The TGA/DSC data as shown in FIG. 37 indicate a weight loss of 30.5% up to 100° C. and broad endothermic signals before decomposition.

Characterization of Trimesate

Figure 38:
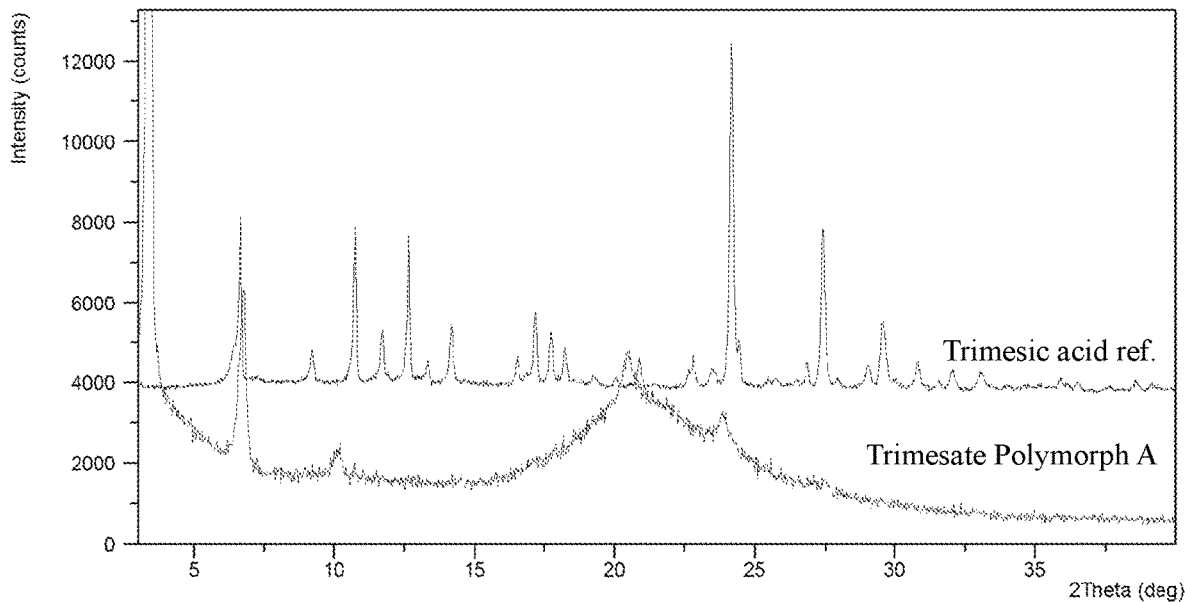
FIG. 38 depicts an XRPD pattern overlay of heptadecan-9-yl 8-((2-hydroxyethyl)(6-oxo-6-(undecyloxy)hexyl)amino)octanoate trimesate Polymorph A and the corresponding acid, trimesic acid.
Figure 39:
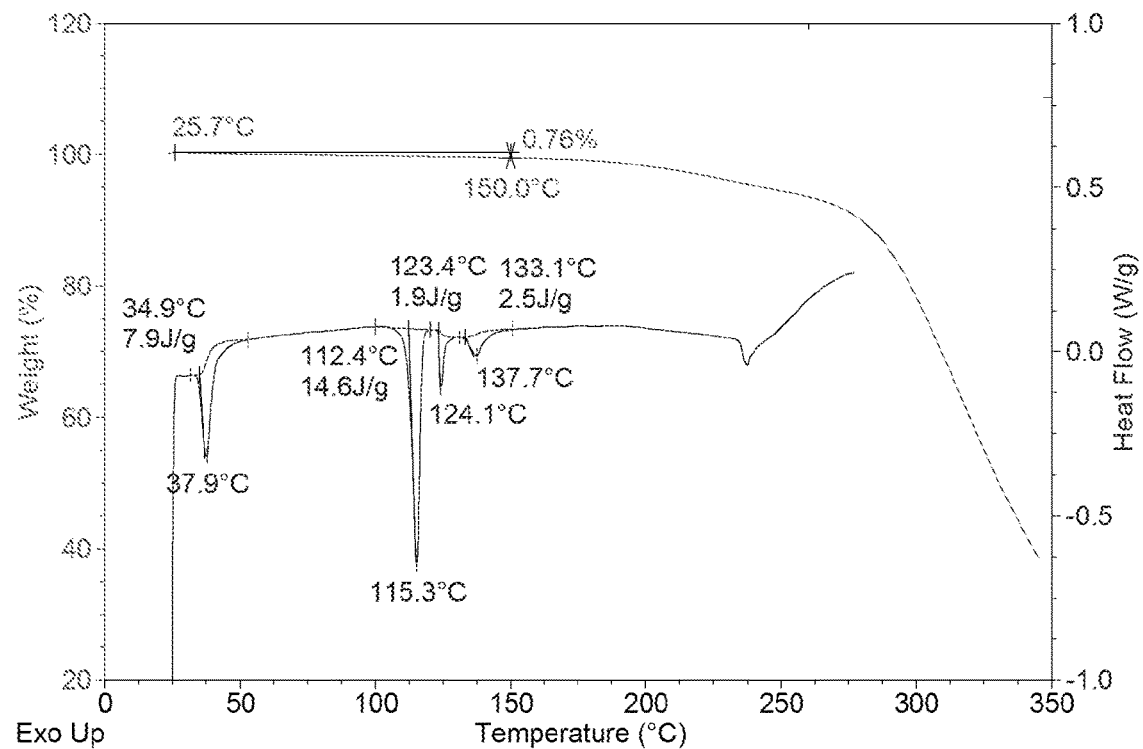
FIG. 39 depicts TGA and DSC data for heptadecan-9-yl 8-((2-hydroxyethyl)(6-oxo-6-(undecyloxy)hexyl)amino)octanoate trimesate Polymorph A.

Compound 2 trimesate Polymorph A was prepared by combining Compound 2 freebase with trimesic acid in n-heptane and showed crystallinity as characterized by XRPD in FIG. 38. The TGA/DSC data as shown in FIG. 39 indicate a weight loss of 0.8% up to 150° C. and multiple endothermic signals before decomposition.

Characterization of L-tartrate

Figure 40:
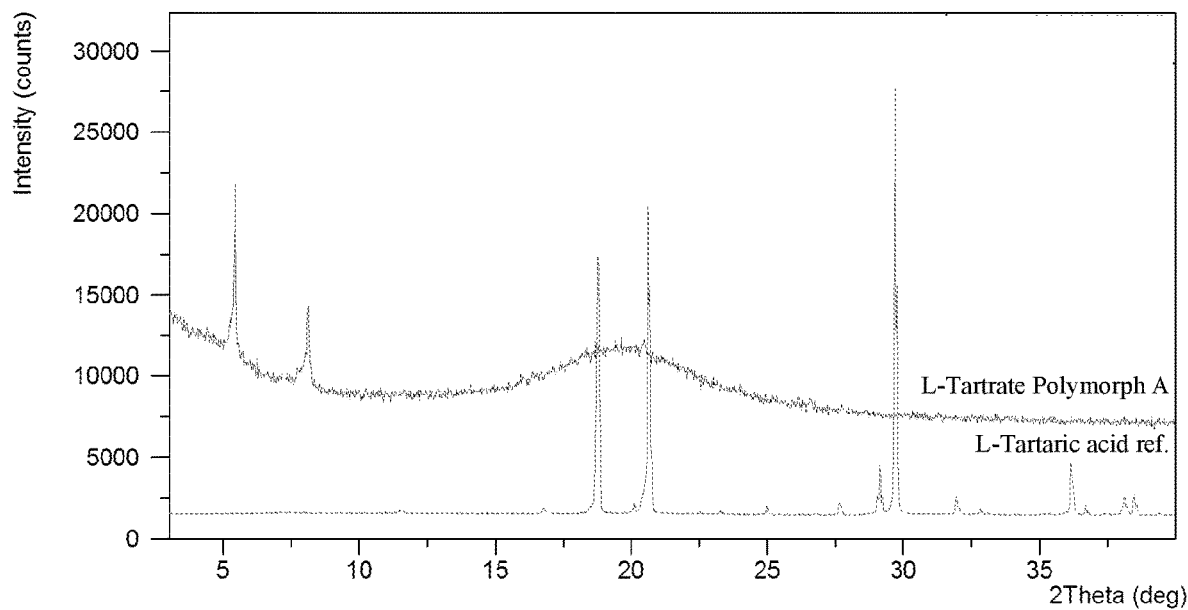
FIG. 40 depicts an XRPD pattern overlay of heptadecan-9-yl 8-((2-hydroxyethyl)(6-oxo-6-(undecyloxy)hexyl)amino)octanoate L-tartrate Polymorph A and the corresponding acid, L-tartaric acid.
Figure 41:
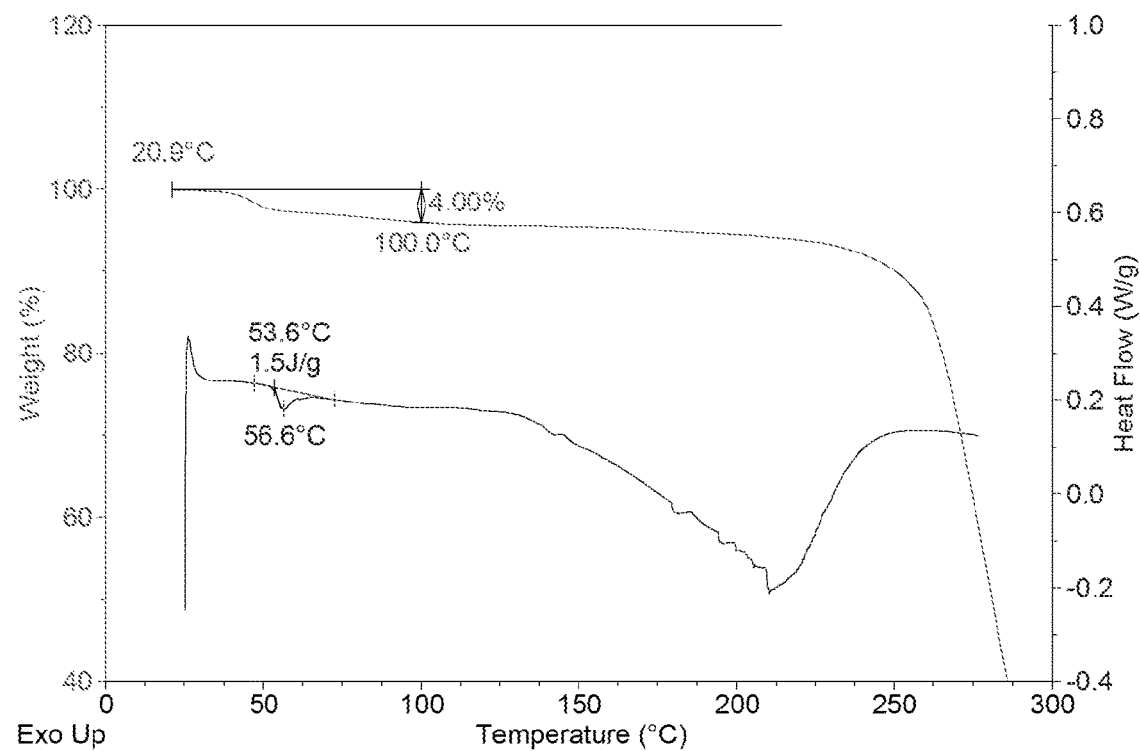
FIG. 41 depicts TGA and DSC data for heptadecan-9-yl 8-((2-hydroxyethyl)(6-oxo-6-(undecyloxy)hexyl)amino)octanoate L-tartrate Polymorph A.

Compound 2 L-tartrate Polymorph A was prepared by combining Compound 2 freebase with L-tartaric acid in n-heptane and showed crystallinity as characterized by XRPD in FIG. 40. The TGA/DSC data as shown in FIG. 41 indicate a weight loss of 4.0% up to 100° C. and multiple endothermic signals before decomposition.

Characterization of Mesylate

Figure 42:
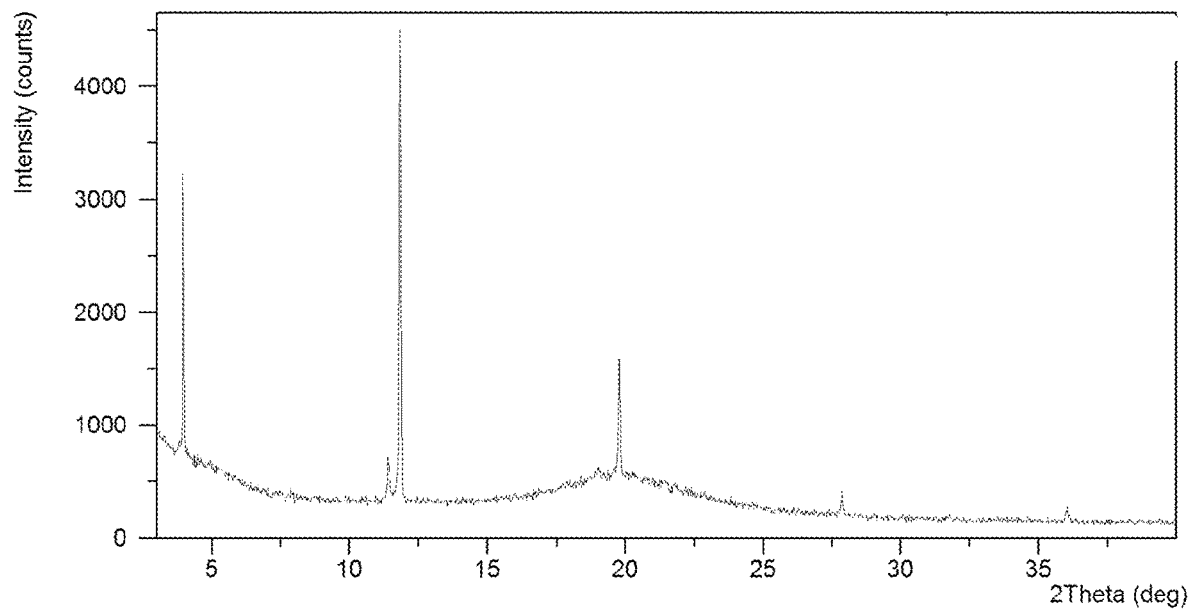
FIG. 42 depicts an XRPD pattern of heptadecan-9-yl 8-((2-hydroxyethyl)(6-oxo-6-(undecyloxy)hexyl)amino)octanoate mesylate Polymorph A.
Figure 43:
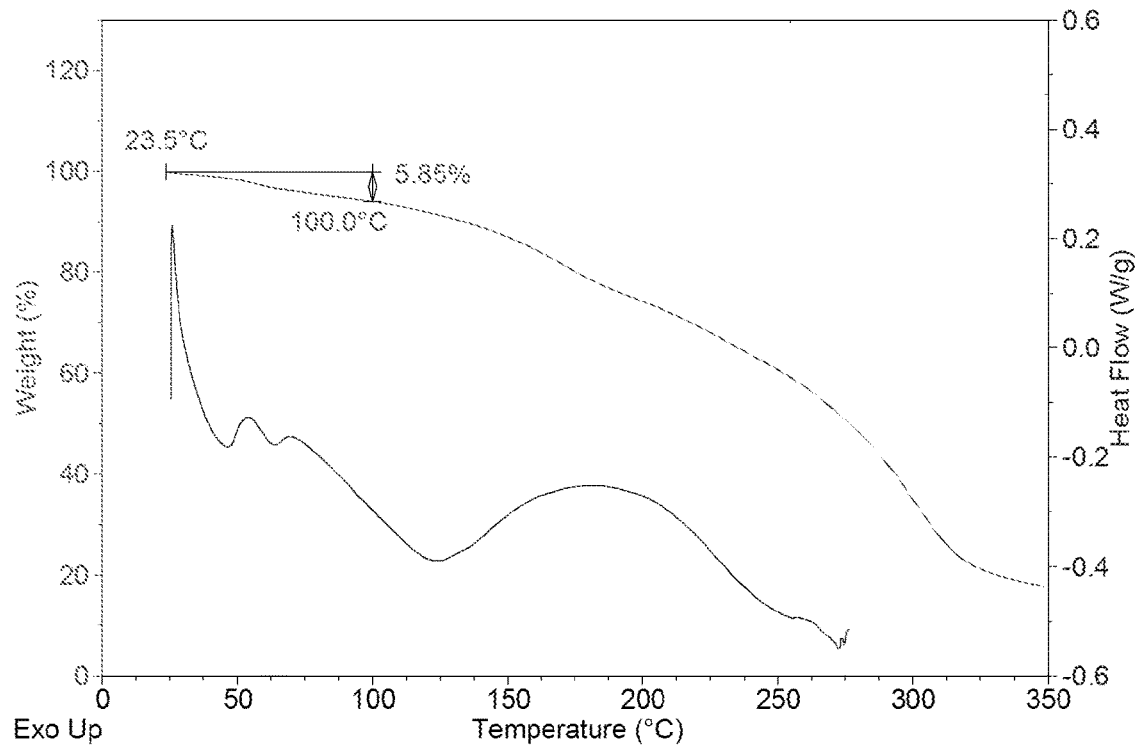
FIG. 43 depicts TGA and DSC data for heptadecan-9-yl 8-((2-hydroxyethyl)(6-oxo-6-(undecyloxy)hexyl)amino)octanoate mesylate Polymorph A.

Compound 2 mesylate Polymorph A was prepared by combining Compound 2 freebase with methanesulfonic acid in n-heptane and showed crystallinity as characterized by XRPD in FIG. 42. The TGA/DSC data as shown in FIG. 43 indicate a weight loss of 5.9% up to 100° C. and irregular signals in the DSC curve.

Characterization of 4-acetamido Benzoate

Figure 44:
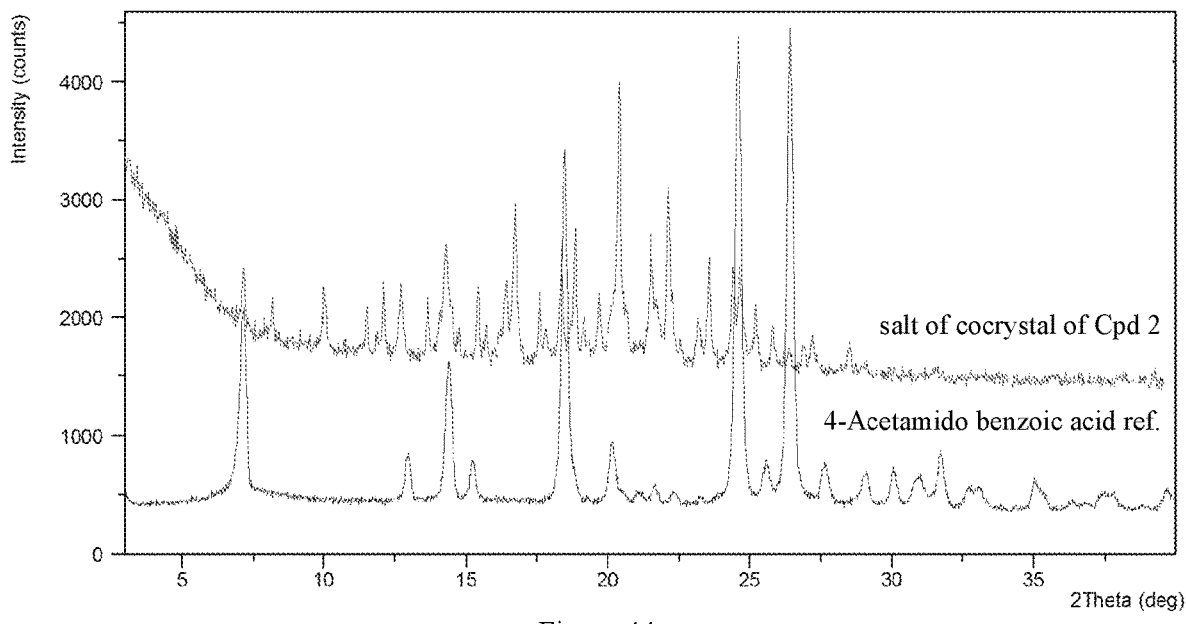
FIG. 44 depicts an XRPD pattern overlay of heptadecan-9-yl 8-((2-hydroxyethyl)(6-oxo-6-(undecyloxy)hexyl)amino)octanoate 4-acetamido benzoate Polymorph A and the corresponding acid, 4-acetamido benzoic acid.
Figure 45:
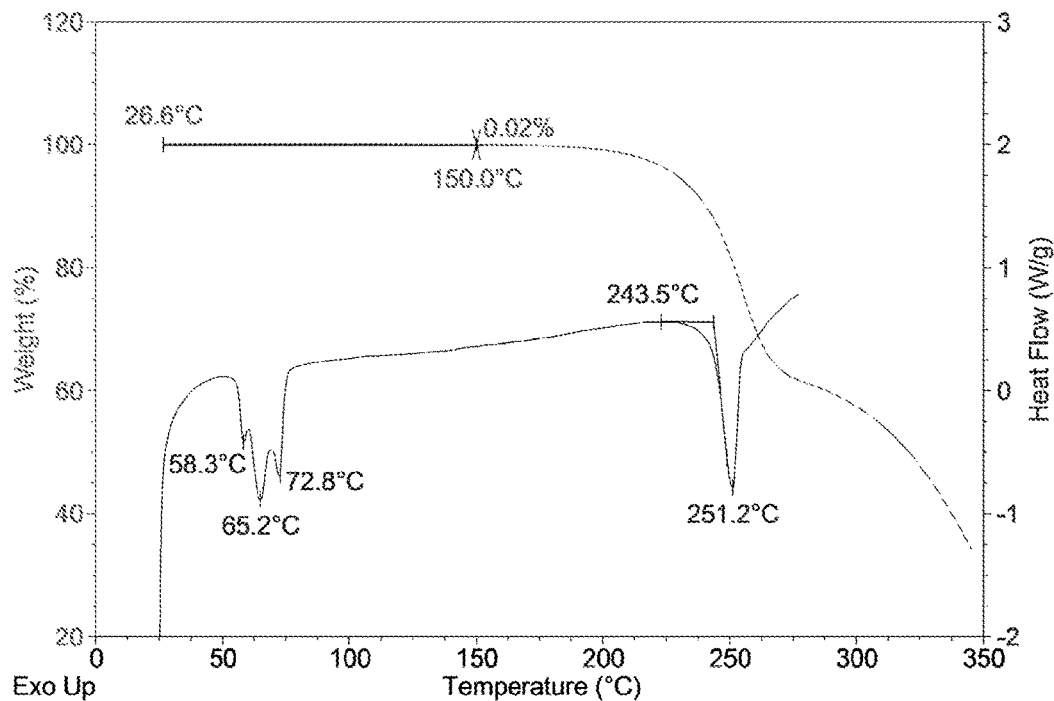
FIG. 45 depicts TGA and DSC data for heptadecan-9-yl 8-((2-hydroxyethyl)(6-oxo-6-(undecyloxy)hexyl)amino)octanoate 4-acetamido benzoate Polymorph A.

Compound 2 4-acetamido benzoate Polymorph A was prepared by combining Compound 2 freebase with 4-acetamido benzoic acid in n-heptane and showed crystallinity as characterized by XRPD in FIG. 44. The TGA/DSC data as shown in FIG. 45 indicate a weight loss of 0.02% up to 150° C. and multiple endothermic signals before decomposition.

Example 3: Salts or Cocrystals of Compound 3

Preparation

Compound 3 freebase, as characterized via modulated DSC (mDSC), exhibits no glass transition signal. A weight loss of 1.2% was observed up to 200° C., and endotherms were observed at −44.1° C. and −29.9° C. (peak).

Similar to the process described in Example 1 or 2, to identify a crystalline salt form or cocrystal of Compound 3, screening was performed under 93 conditions using 31 acids and three solvent systems. 0.5 mL stock solutions of Compound 3 freebase (~40 mg/mL) was dispersed in selected solvent and corresponding salt former was added with a molar charge ratio of 1:1. The mixtures of freebase and the coformer compound (e.g., an acid) were first transferred to temperature cycling from 50° C. to 5° C. for three cycles (heating rate of 4.5° C./min, cooling rate of 0.1° C./min) and then stored at 5° C. before analysis. If the samples were still clear, they would be subjected to slow evaporation at 5° C. to obtain gels. Resulting solids were isolated and analyzed.

Isolated crystal solids were characterized by X-ray powder diffraction (XRPD), thermo-gravimetric analysis (TGA) and differential scanning calorimetry (DSC), with proton nuclear magnetic resonance ('H NMR) to confirm the freebase chemical structure and also potential co-existence with some organic acids. Exemplary data from the initial findings are summarized in Table7.

TABLE 7

| # | Acid | Solvent | | |
|---|------|---------|---|---|
|   |      | n-Heptane | EtOAc | Toluene |
| 1 | Trimesic acid | Trimesate Type A | Acid | Trimesate Type A |
| 2 | Trimellitic acid | Acid | Acid | Acid |
| 3 | (−)-2,3-Dibenzoyl-L-tartaric acid | Gel | Gel | Gel |
| 4 | Fumaric acid | Gel | Gel | Gel |
| 5 | Terephthalic acid | Gel | Gel | Gel |
| 6 | Phthalic acid | Gel | Gel | Gel |
| 7 | Isophthalic acid | Acid | Acid | Acid |
| 8 | Benzoic acid | Gel | Gel | Gel |
| 9 | Cinnamic acid | Gel | Gel | Gel |
| 10 | 4-Hydroxy benzoic acid | Gel | Gel | Gel |
| 11 | Salicylic acid | Gel | Gel | Gel |
| 12 | Adipic acid | Acid | Acid | Acid |
| 13 | Suberic acid | Acid | Gel | Acid |
| 14 | Sebacic acid | Acid | Acid | Acid |
| 15 | 4-Acetamido benzoic acid | Acid | Acid | Acid |
| 16 | S-(+)-Mandelic | Gel | Gel | Gel |
| 17 | Orotic acid | Acid | Acid | Acid |
| 18 | Hexanoic acid | Gel | Gel | Gel |
| 19 | Citric acid | Gel | Gel | Gel |
| 20 | Acetic acid | Gel | Gel | Gel |
| 21 | Succinic acid | Acid | Gel | Gel |
| 22 | Malonic acid | Gel | Gel | Gel |
| 23 | (+)-Camphor-10-sulfonic acid | Gel | Gel | Gel |
| 24 | Nicotinic acid | Acid | Acid | Acid |
| 25 | (+)-L-tartaric acid | Gel | Gel | Gel |
| 26 | Hydrochloric acid | Gel | Gel | Gel |
| 27 | Sulfuric acid | Gel | Gel | Gel |
| 28 | Phosphoric acid | Gel | Gel | Gel |
| 29 | Methanesulfonic acid | Gel | Gel | Gel |
| 30 | p-Toluene sulfonic acid | Gel | Gel | Gel |
| 31 | 2,5-Dihydroxybenzoic acid | Gel | Gel | Gel |

Characterization of Trimesate

Figure 46:
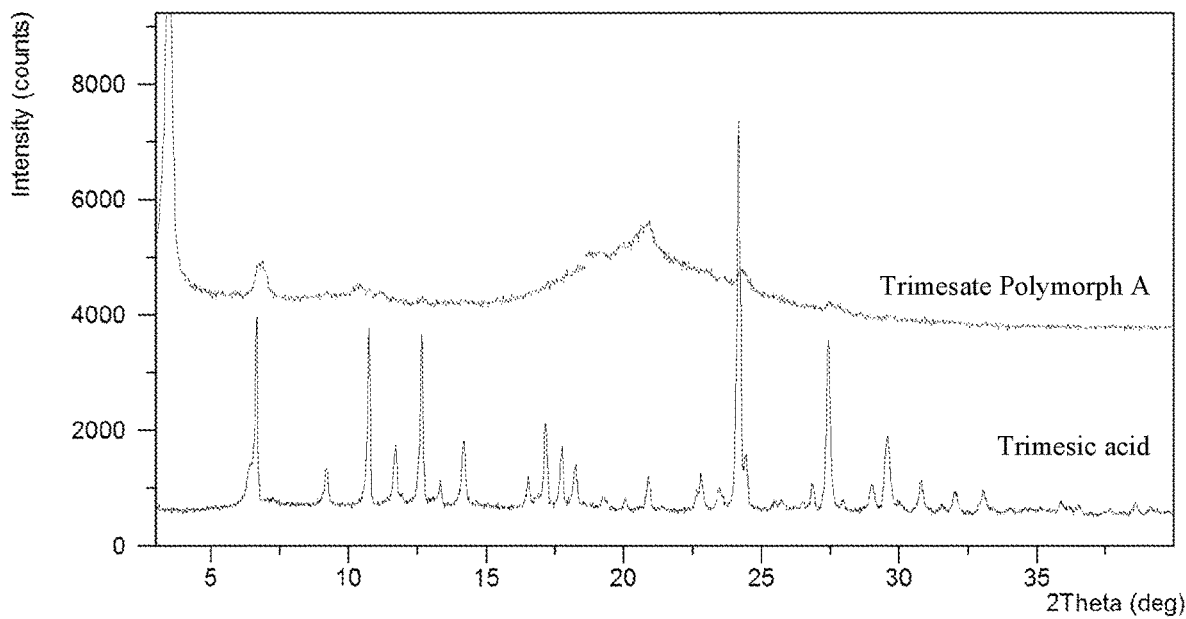
FIG. 46 depicts an XRPD pattern overlay of heptadecan-9-yl 8-((2-hydroxyethyl)(8-(nonyloxy)-8-oxooctyl)amino)octanoate trimesate Polymorph A and the corresponding acid, trimesic acid.
Figure 47:
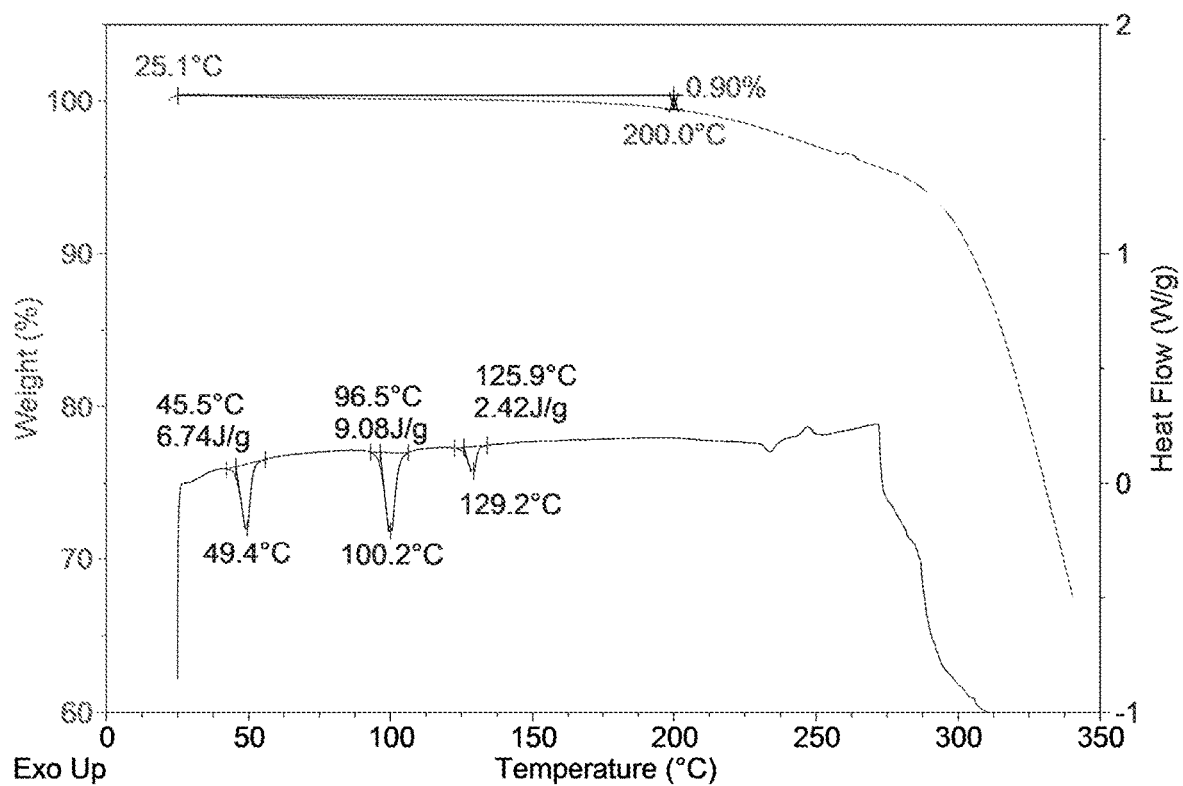
FIG. 47 depicts TGA and DSC data for heptadecan-9-yl 8-((2-hydroxyethyl)(8-(nonyloxy)-8-oxooctyl)amino)octanoate trimesate Polymorph A.
Figure 49:
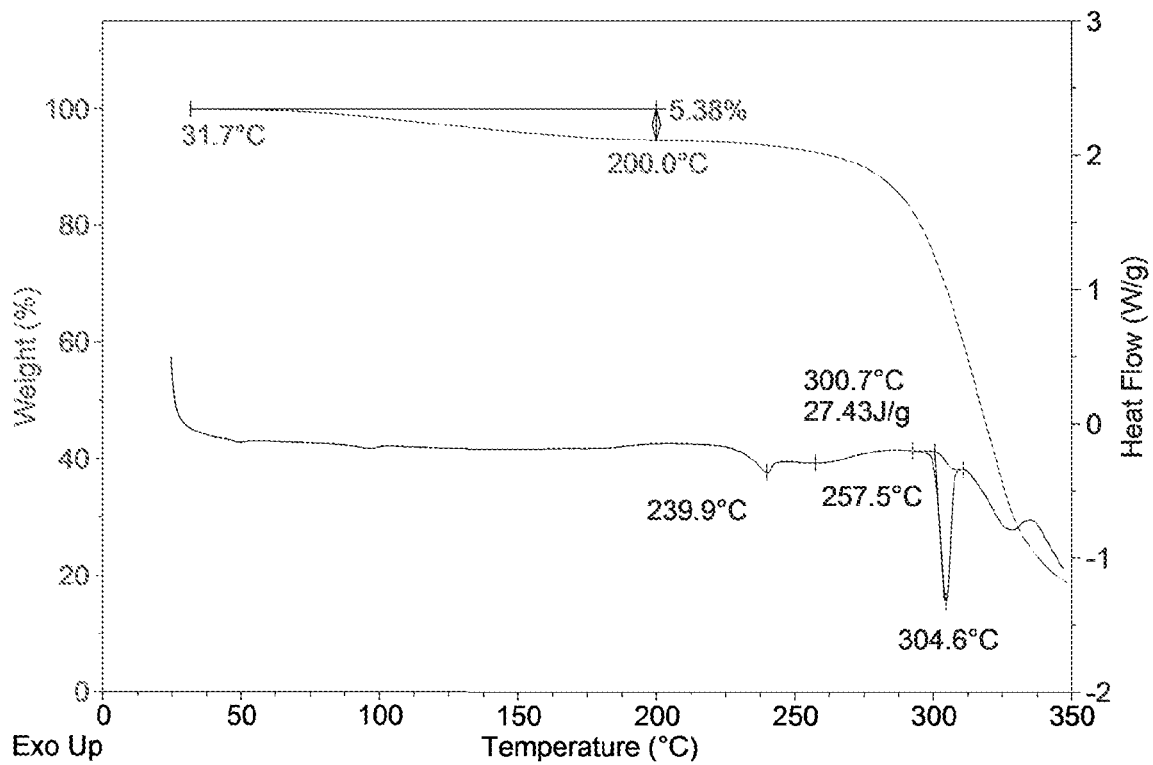
FIG. 49 depicts TGA and DSC data for heptadecan-9-yl 8-((2-hydroxyethyl)(8-(nonyloxy)-8-oxooctyl)amino)octanoate trimesate Polymorph B.
Figure 50:
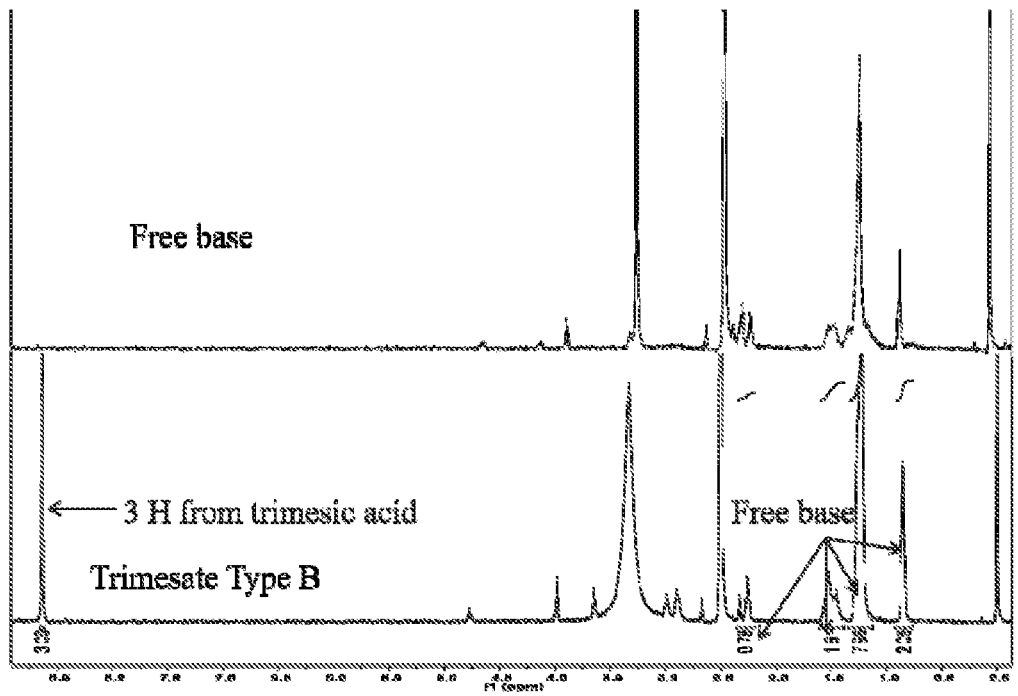
FIG. 50 depicts an ¹H NMR overlay of heptadecan-9-yl 8-((2-hydroxyethyl)(8-(nonyloxy)-8-oxooctyl)amino)oc-tanoate trimesate Polymorph B and freebase.
Figure 51:
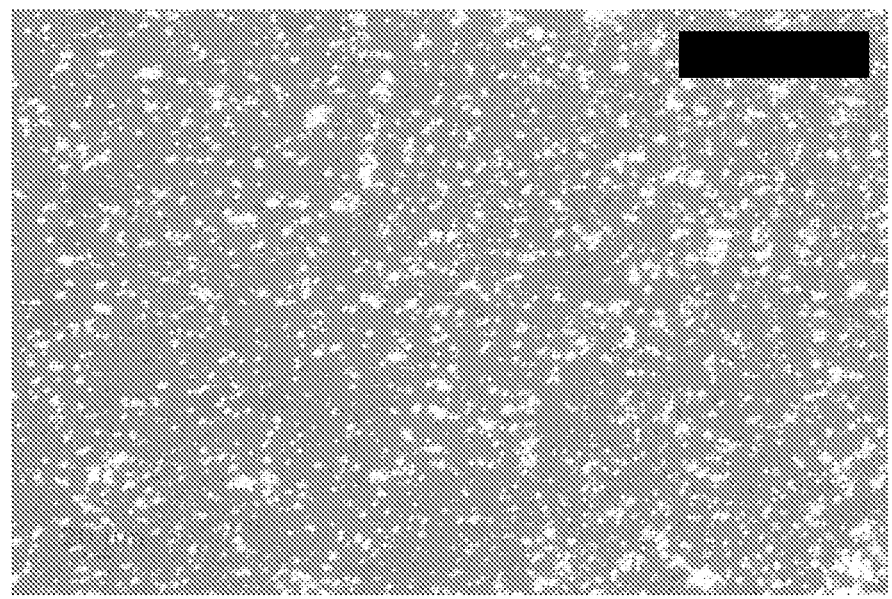
FIG. 51 is a polarized light microscopy (PLM) image of heptadecan-9-yl 8-((2-hydroxyethyl)(8-(nonyloxy)-8-oxooctyl)amino)octanoate trimesate Polymorph B.

Compound 3 trimesate Polymorph A was prepared by combining Compound 3 freebase with trimesic acid in n-heptane and showed crystallinity as characterized by XRPD in FIG. 46. The TGA/DSC data as shown in FIG. 47 indicate a weight loss of 0.9% up to 200° C. and three endothermic peaks at 49.4° C., 100.2° C. and 129.2° C. (peak temperature) before decomposition. Polymorph B was obtained via temperature cycling in EtOH/n-heptane (1:19, v/v) from 50° C. to 5° C. with molar charge ratio (compound 3:trimesic acid) at 1:1, and showed crystallinity as characterized by XRPD in FIG. 48. The TGA/DSC data as shown in FIG. 49 indicate a weight loss of 5.4% up to 200° C. and two endothermic peaks at 239.9° C. and 257.5° C. before decomposition at 304.6° C. An $^1$H NMR spectrum was collected using $(CD_3)_2SO$ as the test solvent, and signals of trimesic acid and compound 3 were observed. See FIG. 50.

Example 4: Salts or Co-Crystals of MC3

Only one crystalline salt of MC3 (O,O-Dibenzoyl-L-Tartrate, abbreviated as "DBLT" hereafter) has been previously identified, and only one polymorph, Type A, has been discovered for the DBLT salt. An onset temperature of 69.8° C. in DSC analysis indicated a low melting point, however, not as low as the free base which is oil-like at room temperature. The crude free base has an HPLC purity of 88.6 area % and was used in the synthesis of the DBLT salt. Impurities are not rejected by the salt formation and the purity of the crystallized salt was found to be the same as the crude free base. Additional salt screening experiments were performed to identify new crystalline salts.

An oil-like MC3 free base with an HPLC purity of 97.6 area % ("purified free base") was used in the salt screening. A total of 24 acids and three solvent systems were screened. Crystalline salt hits were obtained with (+)-O,O-di-pivaloyl-D-tartaric acid (DPDT), (−)-O,O-di-pivaloyl-L-tartaric acid (DPLT), and trimesic acid.

Solvent Screening

A solvent screening was performed by reaction of free base and DPDT, DPLT and trimesic acid in 17 selected solvents to improve crystallinity and facilitate salt isolation and re-preparation. The X-ray powder diffraction (XRPD) results showed that crystalline trimesate Type A and B were obtained in ketones, esters and some other selected solvents from slurry at room temperature. For DPDT and DPLT salts, no suitable anti-solvent was found, only clear solutions were obtained during the solvent screening.

Based on the screening results, attempts were made to re-prepare trimesate Type A and B, but only trimesate Type A was successfully prepared at a 100-mg scale. Both polymorphs were further characterized using thermogravimetric analysis (TGA), differential scanning calorimetry (DSC), polarizing microscopy (PLM), dynamic vapor sorption (DVS), and HPLC. The characterization results of trimesate samples are summarized in Table 8. As the results show, trimesate Type A is anhydrous and non-hygroscopic.

TABLE 8

| Salt form | Trimesate Type A | Trimesate Type B |
|---|---|---|
| Prepared solvent | EtOAc | Cyclohexane | Toluene |
| Scale, mg | 100 | 100 | 10 |
| Molar ratio (acid/FB)[a] | 1.2 | 1.1 | 1.5 |
| Speculated form[b] | Anhydrate | Anhydrate | N/A |
| HPLC purity (area %) | 98.3 | 99.4[c] | 93.7 |
| Weight loss (%) | 1.9 | 0.3 | 8.0 |
| Endotherm (° C., onset) | 186.4 | 183.8 | 186.8 |
| Hygroscopicity/purity decrease | Non-hygroscopic | N/A | N/A |
| Morphology | Aggregated of small particles (<20 μm) | | |
| Appearance of solution in preparation | Suspension | Wax/emulsus | Wax/emulsus |

N/A: not applicable or data not collected in this study.
[a] the molar ratio (acid/FB) was determined by HPLC/IC.
[b] results speculated based on the preliminary thermal analysis data.
[c] average value of three sampling (100.0 area %, 99.34 area %, and 98.74 area %), suggesting the sample is inhomogeneous.
Hygroscopicity concluded using the water uptake up to 80% RH at 25° C.: <0.2% for non-hygroscopic.

Salt Screening

A total of 41 screening experiments were designed based on the free base pKa>8 and the solubility of MC3. Crystalline hits of trimesate (Type A), DPDT and DPLT salts were obtained.

In the 1st tier experiments, about 10 mg of MC3 free base and the corresponding acid were mixed, at a 1:1 molar ratio, into a 1.5-mL glass vial and 0.5 mL of n-heptane were then added. The mixtures were stirred at room temperature for about two days. If clear solutions were obtained, the samples were cooled at 5° C. or left to evaporate to induce solid formation. All the obtained solids were isolated by centrifugation and vacuum dried at room temperature for about 5 hours before being analyzed by X-Ray Powder Diffraction (XRPD). As summarized in Table 9, amorphous salts or acids were found under most of the conditions while potential crystalline forms were obtained with DPDT, DPLT, and trimesic acid.

To enhance the chance of crystallization during the 2nd tier screening, the concentration of free base was increased from 20 to 50 mg/mL when using the acids that yielded solutions in the 1st tier screening. Also, isopropyl alcohol/n-heptane (3:97, v/v) was used with those acids which yielded crystalline acid in the 1st tier screening. As summarized in Table 10, no new crystalline hit was obtained.

Six more acids with structures closely related to trimesic acid were screened. The free base and the acids were mixed, at a 1:1 molar ratio, in EtOAc (free base loading 50 mg/mL) and the suspensions were then shaken at room temperature for about three days. The results are summarized in Table 11.

TABLE 9

| No. | Acid | Solid form | No. | Acid | Solid form |
|---|---|---|---|---|---|
| 1 | Hexanoic acid | Amorphous[a] | 10 | (R)-(−)-Mandelic acid | Amorphous[a] |
| 2 | Fumaric acid | Acid | 11 | Benzyloxy lactic acid | Amorphous[a] |
| 3 | Adipic acid | Amorphous | 12 | (+)-O,O-Di-pivaloyl-D-tartaric acid | DPDT salt Type A[a] |
| 4 | Suberic acid | Acid | 13 | (−)-O,O-Di-pivaloyl-L-tartaric acid | DPLT salt Type A[a] |
| 5 | Sebacic acid | Acid | 14 | Terephthalic acid | Acid |
| 6 | Alginic acid | Amorphous[a] | 15 | Trimesic acid | Acid + new peaks[c] |
| 7 | Cinnamic acid | Amorphous[a] | 16 | 4-Hydroxy benzoic | Acid |
| 8 | Benzoic acid, 4-acetamido | Acid | 17 | 2-(4-Hydroxybenzoyl)-benzoic acid | Amorphous[a] |

TABLE 9-continued

| No. | Acid | Solid form | No. | Acid | Solid form |
|---|---|---|---|---|---|
| 9 | (S)-(+)-Mandelic acid | Amorphous[a] | 18 | (+)-2,3-Dibenzoyl-D-tartaric acid | DBDT salt Type A[b] |

[a] clear solution was observed after slurry at room temperature (RT) and 5° C., which was then transferred to slow evaporate at RT.
[b] obtained in a previous experiment with no obvious purity improvement.
[c] new peaks conformed to trimesate Type A.

TABLE 10

| No. | Acid | Solvent | Solid form |
|---|---|---|---|
| 1 | Hexanoic acid | n-Heptane | N/A |
| 2 | Alginic acid | | N/A |
| 3 | Cinnamic acid | | N/A |
| 4 | (S)-(+)-Mandelic acid | | N/A |
| 5 | R)-(−)-Mandelic acid | | N/A |
| 6 | Benzyloxy lactic acid | | N/A |
| 7 | (+)-O,O-Di-pivaloyl-D-tartaric acid | | N/A |

TABLE 10-continued

| No. | Acid | Solvent | Solid form |
|---|---|---|---|
| 8 | (−)-O,O-Di-pivaloyl-L-tartaric acid | | N/A |
| 9 | 2-(4-Hydroxybenzoyl)-benzoic acid | | N/A |
| 10 | Fumaric acid | IPA/H$_2$O (3:97, v/v) | Acid |
| 11 | Adipic acid | | Amorphous |
| 12 | Suberic acid | | Acid |
| 13 | Sebacic acid | | Acid |
| 14 | Benzoic acid, 4-acetamido | | Acid |
| 15 | Terephthalic acid | | Acid |
| 16 | Trimesic acid | | Acid |
| 17 | 4-Hydroxy benzoic | | Acid |

N/A: clear solution was observed after slurry at RT and 5° C..

TABLE 11

| No. | Acid | Solvent | Solid form |
|---|---|---|---|
| 1 | 1,2,4-Trimellitic acid | EtOAc | Amorphous |
| 2 | Phthalic acid | | Amorphous |
| 3 | Isophthalic acid | | Amorphous |
| 4 | Terephthalic acid | | Acid |
| 5 | Orotic acid | | Acid + new peaks* |
| 6 | 1,2,3-Benzene tricarboxylic acid | | Amorphous |

*only amorphous was observed in the re-preparation experiment.

Optimization of Solvent Systems

A solvent screening was performed to select an optimal solvent system for re-preparation of the salt hits and to improve crystallinity. The free base was mixed in a 1:1 molar ratio, with DPDT, DPLT, and trimesic acid in 17 selected solvents. Trimesate Type A and B polymorphs were isolated from slurries in several solvents (see Table 12). DPDT and DPLT salts were not obtained as solids from any solvent. In addition, the samples containing tetrahydrofuran (THF)/H$_2$O, THF, cyclohexane and 1,4-dioxane were freeze-dried, but no crystalline solid was obtained.

TABLE 12

| | | Acid | | |
|---|---|---|---|---|
| Form | Solvent | DPDT | DPLT | Trimesic acid |
| 1 | Acetone | N/A* | N/A* | Trimesate Type A |
| 2 | Methyl isobutyl ketone (MIBK) | N/A | N/A | Trimesate Type A |
| 3 | Methyl ethyl ketone (MEK) | N/A | N/A | Trimesate Type A |
| 4 | CH$_2$Cl$_2$ | N/A | N/A | Acid |
| 5 | Methyl tert-butyl ether (MTBE) | N/A | N/A | Trimesate Type A |
| 6 | 2-Methyl tetrahydrofuran (2-MeTHF) | N/A | N/A | N/A |
| 7 | Tetrahydrofuran (THF) | N/A* | N/A* | N/A |
| 8 | Anisole | N/A | N/A | Trimesate Type A |
| 9 | 1,4-Dioxane | N/A* | N/A* | N/A |
| 10 | EtOAc | N/A | N/A | Trimesate Type A |
| 11 | Isopropyl acetate (IPAc) | N/A | N/A | Trimesate Type A |
| 12 | Acetonitrile (CAN) | N/A* | N/A* | N/A |
| 13 | MeOH | N/A* | N/A* | N/A |
| 14 | Isopropyl alcohol (IPA) | N/A* | N/A* | N/A |
| 15 | Cyclohexane | N/A | N/A | Trimesate Type A |
| 16 | Xylene | N/A | N/A | N/A |
| 17 | Toluene | N/A | N/A | Trimesate Type B |

N/A: clear solution was obtained after slurry at RT and 5° C..
*about 0.2~0.3 mL of H$_2$O was added into the clear solution to induce precipitation and emulsion was obtained.

Preparation of Trimesate Polymorphs (100 mg Scale)

Heating and cooling experiments were carried out at 100-mg scale to improve crystal morphology and chemical purity. Trimesate Type A polymorph was successfully re-prepared in cyclohexane and EtOAc following the procedure detailed below.

Preparation of Trimesate Type A Polymorph:

A 5 mL vial was charged with 100.0 mg of the free base (97.6 area %) and 30 mg of trimesic acid and 2 mL of cyclohexane or EtOAc, were added. The suspension was stirred at room temperature for about 0.5 h. The solution was continued to be stirred while being heated and cooled between 5° C. and 50° C. for two cycles with a 4.5° C./min heating rate and a 0.1° C./min cooling rate. The resulting solid was isolated by centrifugation and dried under vacuum at room temperature for 2 hours before characterization.

Preparation of Trimesate Type B Polymorph:

About 10 mg of free base and trimesic acid were mixed, at a 1:1 molar ratio, in a 1.5-mL glass vial. n-Heptane (0.5 mL) was added. The mixtures were magnetically stirred at RT for about two days. If clear solutions were obtained, the samples were cooled at 5° C. or left to evaporate to induce solid formation. All the obtained solids were isolated by centrifugation and vacuum dried at RT for about 5 hours before being analyzed by XRPD.

Characterization of Trimesate Polymorphs

Both trimesate Type A (100-mg scale) and Type B (10-mg scale) were characterized, and results are summarized in Table 8.

Figure 52:
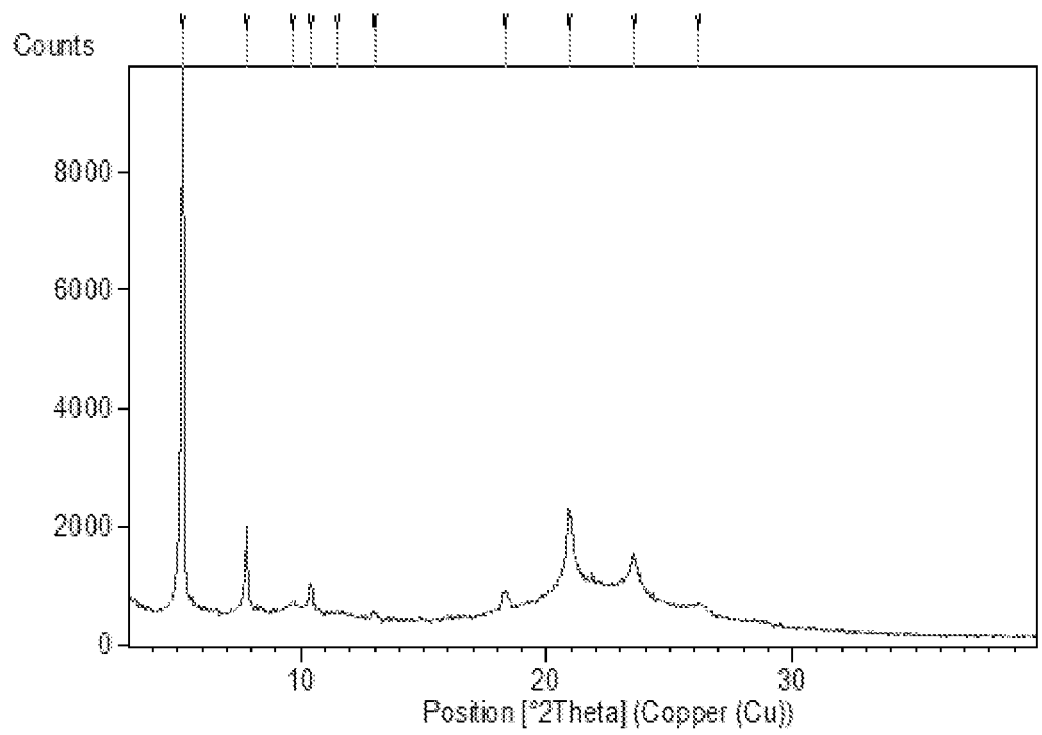
FIG. 52 is an XRPD pattern of (6Z,9Z,28Z,31Z)-heptatriaconta-6,9,28,31-tetraen-19-yl 4-(dimethylamino)butanoate trimesate Type A polymorph.
Figure 53:
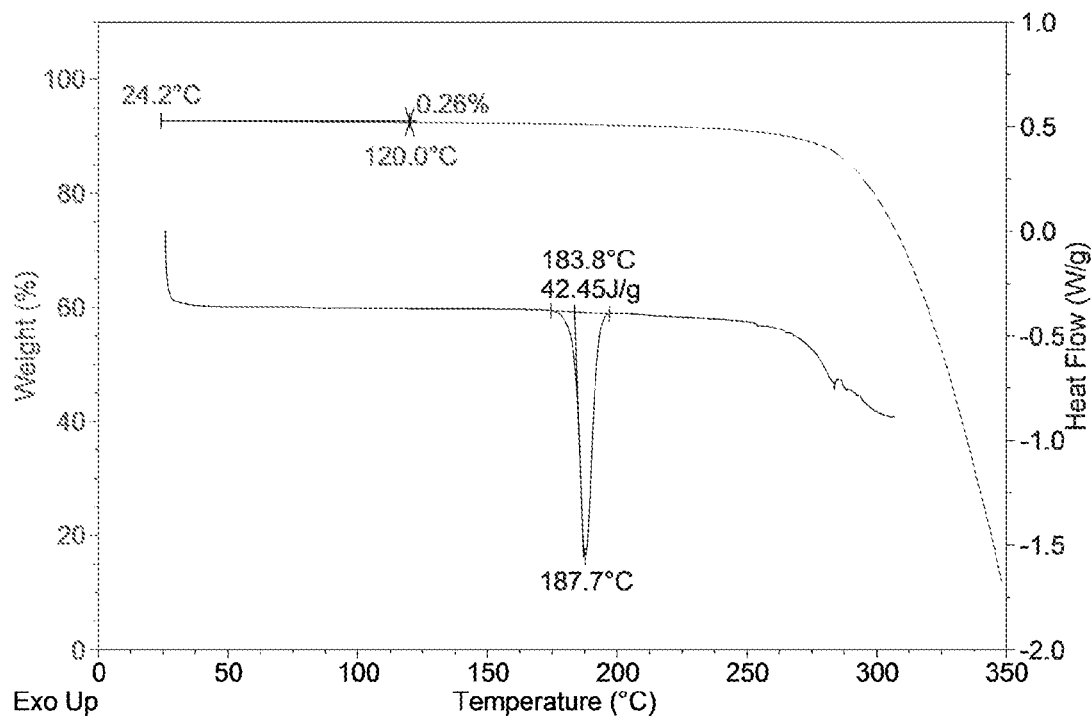
FIG. 53 depicts TGA and DSC data for (6Z,9Z,28Z,31Z)-heptatriaconta-6,9,28,31-tetraen-19-yl 4-(dimethylamino) butanoate trimesate Type A polymorph prepared with cyclohexane.
Figure 54:
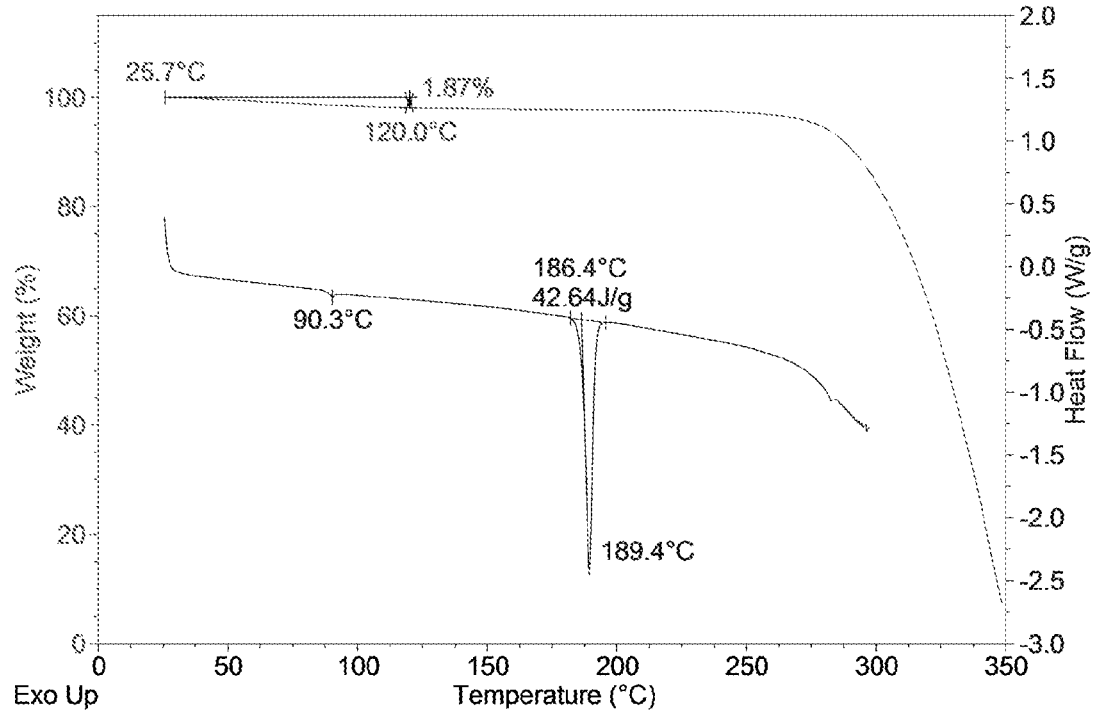
FIG. 54 depicts TGA and DSC data for (6Z,9Z,28Z,31Z)-heptatriaconta-6,9,28,31-tetraen-19-yl 4-(dimethylamino) butanoate trimesate Type A polymorph prepared with EtOAc.
Figure 55:
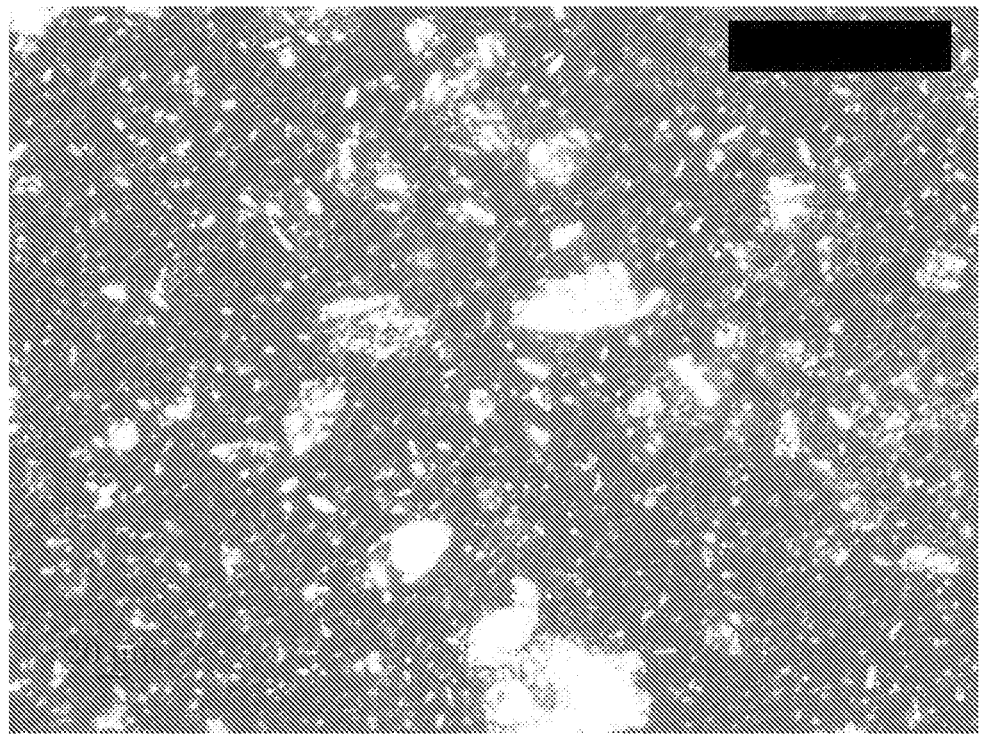
FIG. 55 is a polarized light microscopy (PLM) image of (6Z,9Z,28Z,31Z)-heptatriaconta-6,9,28,31-tetraen-19-yl 4-(dimethylamino)butanoate trimesate Type A polymorph prepared with cyclohexane.
Figure 56:
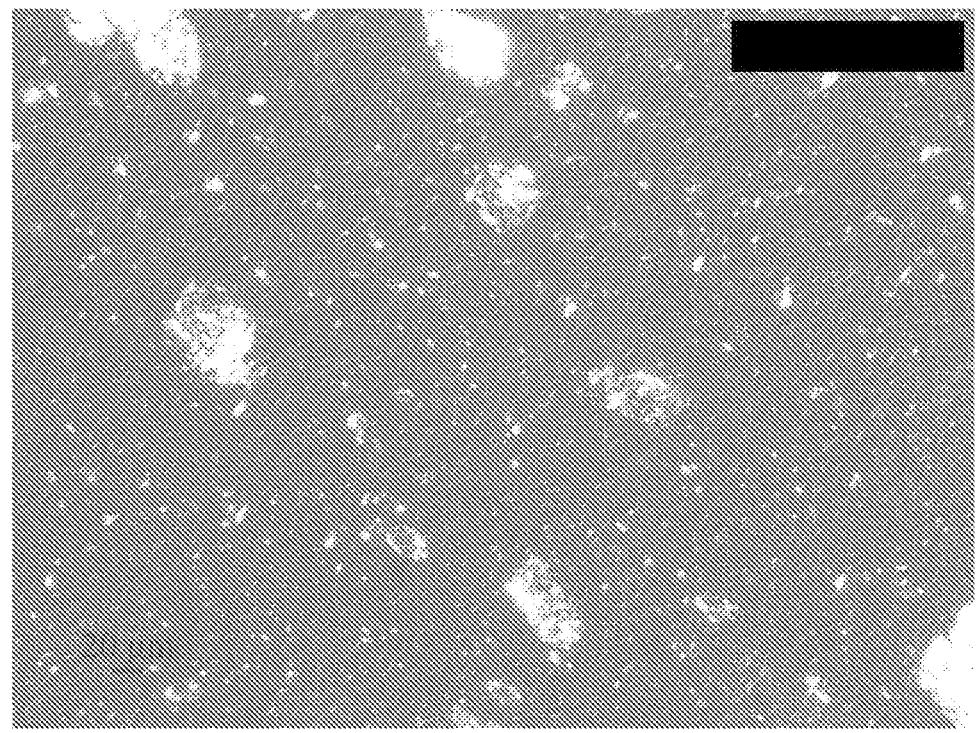
FIG. 56 is a polarized light microscopy (PLM) image of (6Z,9Z,28Z,31Z)-heptatriaconta-6,9,28,31-tetraen-19-yl 4-(dimethylamino)butanoate trimesate Type A polymorph prepared with EtOAc.
Figure 59:
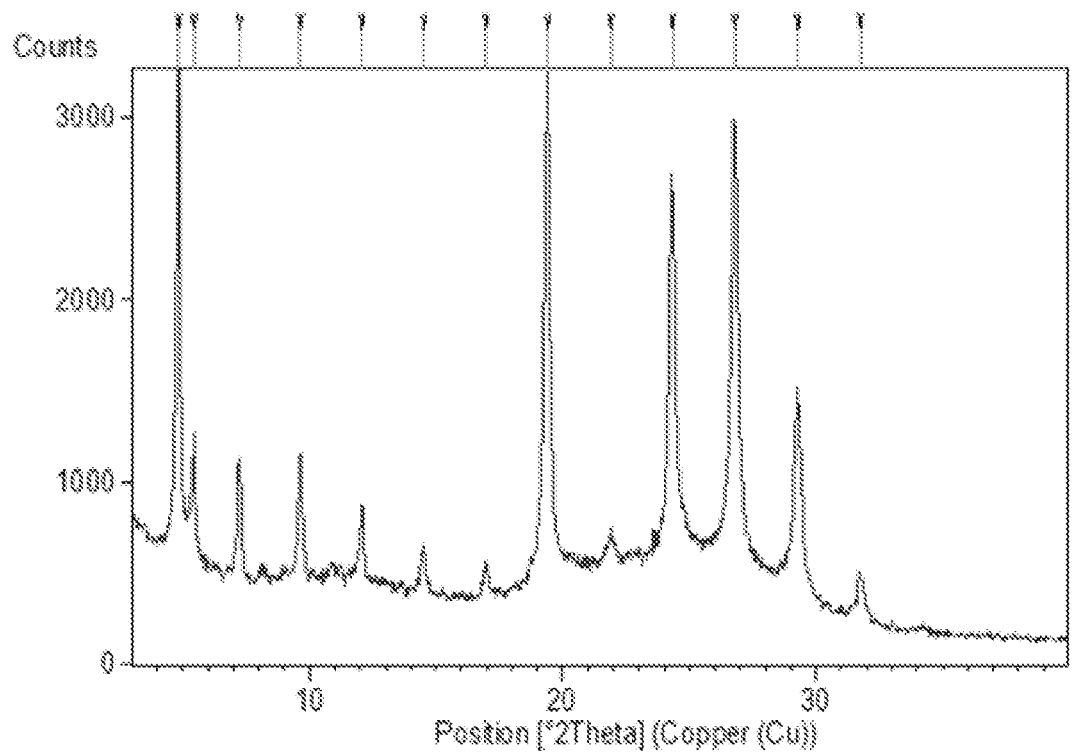
FIG. 59 is an XRPD pattern of (6Z,9Z,28Z,31Z)-heptatriaconta-6,9,28,31-tetraen-19-yl 4-(dimethylamino)butanoate trimesate Type B polymorph.
Figure 60:
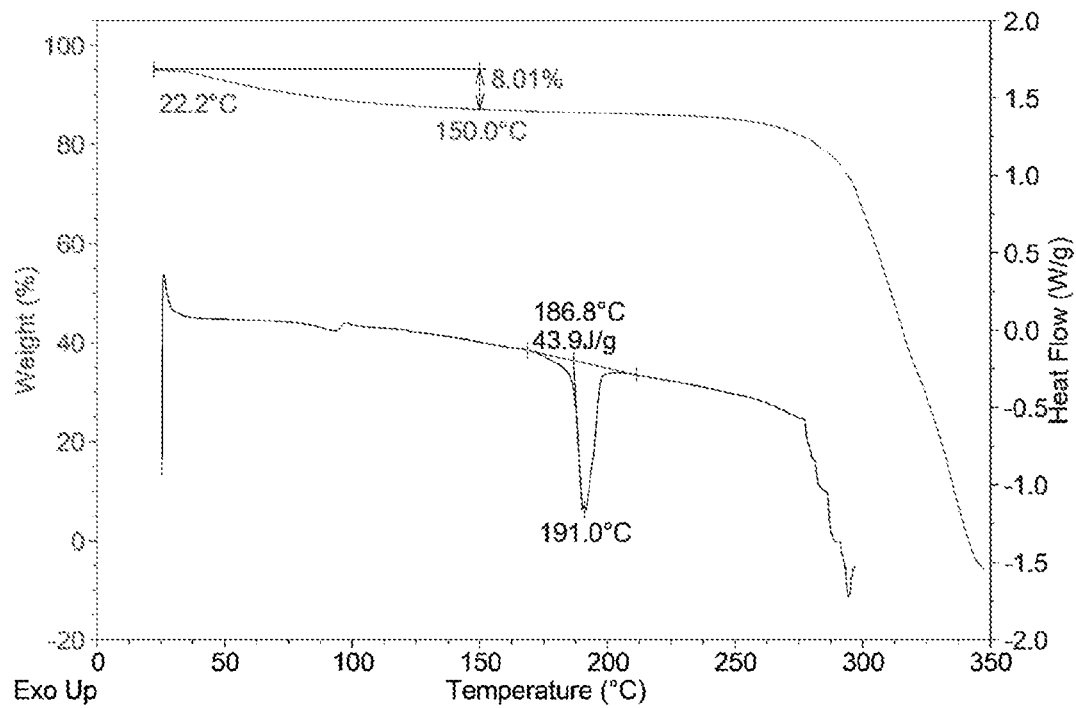
FIG. 60 depicts TGA and DSC data for (6Z,9Z,28Z,31Z)-heptatriaconta-6,9,28,31-tetraen-19-yl 4-(dimethylamino) butanoate trimesate Type B.
Figure 61:
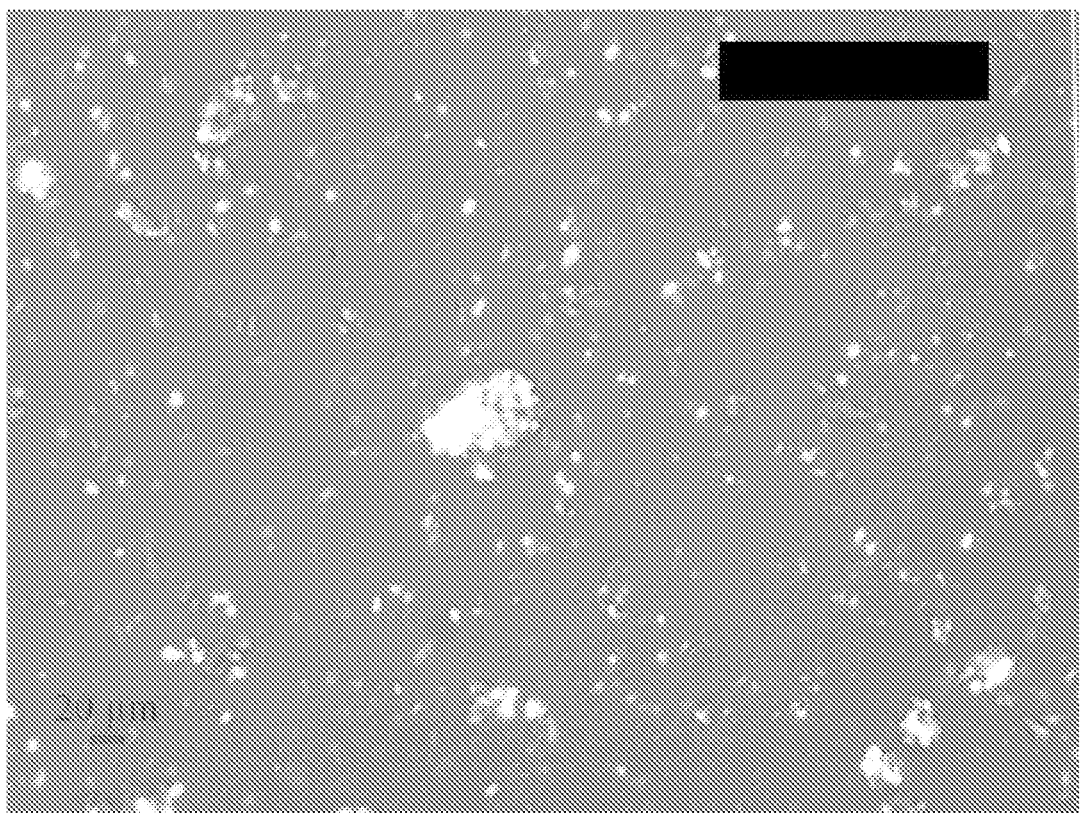
FIG. 61 is a polarized light microscopy (PLM) image of (6Z,9Z,28Z,31Z)-heptatriaconta-6,9,28,31-tetraen-19-yl 4-(dimethylamino)butanoate trimesate Type B polymorph.

The XRPD pattern of polymorph A is shown in FIG. 52. TGA/DSC curves of trimesate Type A polymorph prepared with cyclohexane, displayed in FIG. 53, shows a weight loss of 0.3% before 120° C. and a sharp melting endotherm at 183.8° C. (onset temperature). The TGA/DSC curves of trimesate Type A polymorph prepared with EtOAc displayed in FIG. 54, shows a weight loss of 1.9% before 120° C. and a sharp melting endotherm at 186.4° C. (onset temperature). Agglomerate and small particles (<20 μm) were observed in the trimesate Type A polymorphs. See FIGS. 55 and 56. The XRPD pattern of trimesate Type B polymorph is shown in FIG. 59. TGA/DSC curves displayed in FIG. 60 show a weight loss of 8.0% before 150° C. and a sharp melting endotherm at 186.8° C. (onset temperature). As shown in FIG. 61, agglomerate particles with small size (<20 μm) are observed in trimesate Type B sample.

As the DVS result shows, the trimesate Type A polymorph is non-hygroscopic. See FIG. 57. The hygroscopicity of free base (crude and pure) was determined as well. The crude free base was slightly hygroscopic (0.27 and 0.24% water uptake at 80% relative humidity for the desorption and adsorption isotherms, respectively), but the pure free base was non-hygroscopic (0.17 and 0.14% water uptake at 80% relative humidity for the desorption and adsorption isotherms, respectively).

HPLC Purity of Trimesate Type A

Trimesate Type A samples were prepared according to the procedure described in the foregoing, using the crude free base (HPLC purity of 88.5 area %) or purified free base (HPLC purity of 97.6 area %) as starting material, and analyzed by HPLC. The results of the HPLC purity analysis for the samples prepared with crude and purified free base are summarized in Tables 13 and 14, respectively. No significant HPLC purity change was observed for both samples after the DVS experiment.

TABLE 13

| Sample | Solvent/scale (mg) | Imp 1 (RRT 0.08) | Imp 2 (RRT 0.50) | Imp 3 (RRT 0.51) | Imp 4 (RRT 0.52) | Imp 5 (RRT 0.53) | Imp 6 (RRT 0.90) |
|---|---|---|---|---|---|---|---|
| Free base | N/A | 0.11 | 0.22 | <0.05 | 0.34 | 0.44 | 1.74 |
| Trimesate Type A | EtOAc/100 | <0.05 | 4.18 | 1.38 | <0.05 | <0.05 | 1.96 |
| | Cyclohexane/100 | <0.05 | <0.05 | <0.05 | <0.05 | <0.05 | 1.91 |

| Sample | Solvent/scale (mg) | Imp 7 (RRT 0.91) | Imp 8 (RRT 0.99) | Imp 9 (RRT 1.04) | Imp 10 (RRT 1.06) | Imp 11 (RRT 1.14) | Area (%) |
|---|---|---|---|---|---|---|---|
| Free base | N/A | 0.16 | 0.36 | 5.02 | 0.28 | 2.74 | 88.6 |
| Trimesate Type A | EtOAc/100 | <0.05 | <0.05 | 3.78 | <0.05 | 3.31 | 85.38 |
| | Cyclohexane/100 | <0.05 | <0.05 | 4.45 | <0.05 | 3.97 | 89.66 |

TABLE 14

| Sample | Solvent/scale (mg) | Imp 1 (RRT 0.58) | Imp 2 (RRT 1.04) | Imp 3 (RRT 1.14) | Area(%) |
|---|---|---|---|---|---|
| Free base | N/A | 0.99 | 1.41 | <0.05 | 97.60 |
| Trimesate Type A | EtOAc/100 | <0.05 | 1.04 | 0.68 | 98.28 |
| | Cyclohexane/100 | <0.05 | <0.05 | <0.05 | 100.00 99.36 |
| | | <0.05 | 1.26 | <0.05 | 98.74 (av.) |
| | | <0.05 | 0.66 | <0.05 | 99.34 |

The entire disclosure of each of the patent documents and scientific articles referred to herein is incorporated by reference for all purposes.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

The invention claimed is:

1. A salt or cocrystal of heptadecan-9-yl 8-((2-hydroxyethyl)(6-oxo-6-(undecyloxy)hexyl)amino)octanoate ("Compound 2").

2. The salt or cocrystal of claim 1, wherein the salt or cocrystal is a salt or cocrystal of Compound 2 and a compound selected from the group consisting of trimesic acid, (−)-2,3-dibenzoyl-L-tartaric acid, 4-acetamido benzoic acid, (+)-L-tartaric acid, and methanesulfonic acid.

3. The salt or cocrystal of claim 1, wherein the salt or cocrystal exhibits an X-ray powder diffraction pattern obtained using CuKα radiation having peaks with 2-theta values substantially in accordance with FIG. 36, 38, 40, 42, or 44.

4. The salt or cocrystal of claim 1, wherein the salt or cocrystal exhibits a differential scanning calorimetry thermogram substantially in accordance with the DSC profile shown in FIG. 37, 39, 41, 43, or 45.

5. The salt or cocrystal of claim 1, wherein said salt or cocrystal is substantially free of impurities.

6. The salt or cocrystal of claim 1, being an anhydrate, a solvate, or a hydrate.

7. The salt or cocrystal of claim 1, wherein the stoichiometry of Compound 2 and the compound selected from the group consisting of trimesic acid, (−)-2,3-dibenzoyl-L-tartaric acid, 4-acetamido benzoic acid, (+)-L-tartaric acid, and methanesulfonic acid is within the range of from about 1:0.2 mol/mol to about 1:5 mol/mol.

8. The salt or cocrystal of claim 1, wherein the stoichiometry of Compound 2 and the compound selected from the group consisting of trimesic acid, (−)-2,3-dibenzoyl-L-tartaric acid, 4-acetamido benzoic acid, (+)-L-tartaric acid, and methanesulfonic acid is about 1:1 mol/mol.

9. The salt or cocrystal of claim 1, wherein the salt or cocrystal is a salt or cocrystal of Compound 2 and trimesic acid.

10. The salt or cocrystal of claim 9, wherein the salt or cocrystal exhibits an X-ray powder diffraction pattern obtained using CuKα radiation having peaks with 2-theta values substantially in accordance with FIG. 38.

11. The salt or cocrystal of claim 9, wherein the salt or cocrystal exhibits a differential scanning calorimetry thermogram substantially in accordance with the DSC profile shown in FIG. 39.

12. The salt or cocrystal of claim 9, wherein the salt or cocrystal exhibits an X-ray powder diffraction pattern obtained using CuKα radiation having two characteristic peaks expressed in degrees 2-theta (+/−0.2) selected from the group consisting of 3.4, 6.8, 10.2, 20.5, and 23.8.

13. The salt or cocrystal of claim 9, wherein the salt or cocrystal exhibits an X-ray powder diffraction pattern obtained using CuKα radiation having three characteristic peaks expressed in degrees 2-theta (+/−0.2) selected from the group consisting of 3.4, 6.8, 10.2, 20.5, and 23.8.

14. The salt or cocrystal of claim 9, wherein the salt or cocrystal exhibits an X-ray powder diffraction pattern obtained using CuKα radiation having four characteristic peaks expressed in degrees 2-theta (+/−0.2) selected from the group consisting of 3.4, 6.8, 10.2, 20.5, and 23.8.

15. The salt or cocrystal of claim 9, wherein the salt or cocrystal exhibits an X-ray powder diffraction pattern obtained using CuKα radiation having characteristic peaks expressed in degrees 2-theta (+/−0.2) at 3.4, 6.8, 10.2, 20.5, and 23.8.

16. The salt or cocrystal of claim 1, wherein the salt or cocrystal is a salt or cocrystal of Compound 2 and (−)-2,3-dibenzoyl-L-tartaric acid, and wherein the salt or cocrystal exhibits an X-ray powder diffraction pattern obtained using CuKα radiation having two characteristic peaks expressed in degrees 2-theta (+/−0.2) at 6.1 and 9.1.

17. The salt or cocrystal of claim 1, wherein the salt or cocrystal is a salt or cocrystal of Compound 2 and (+)-L-tartaric acid, and wherein the salt or cocrystal exhibits an X-ray powder diffraction pattern obtained using CuKα radiation having two characteristic peaks expressed in degrees 2-theta (+/−0.2) at 5.4 and 8.1.

18. The salt or cocrystal of claim 1, wherein the salt or cocrystal is a salt or cocrystal of Compound 2 and methanesulfonic acid, and wherein the salt or cocrystal exhibits an X-ray powder diffraction pattern obtained using CuKα radiation having two characteristic peaks expressed in degrees 2-theta (+/−0.2) selected from the group consisting of 4.0, 11.4, 11.8, and 19.8.

19. The salt or cocrystal of claim 1, wherein the salt or cocrystal is a salt or cocrystal of Compound 2 and methanesulfonic acid, and wherein the salt or cocrystal exhibits an X-ray powder diffraction pattern obtained using CuKα radiation having three characteristic peaks expressed in degrees 2-theta (+/−0.2) selected from the group consisting of 4.0, 11.4, 11.8, and 19.8.

20. The salt or cocrystal of claim 1, wherein the salt or cocrystal is a salt or cocrystal of Compound 2 and methanesulfonic acid, and wherein the salt or cocrystal exhibits an X-ray powder diffraction pattern obtained using CuKα radiation having four characteristic peaks expressed in degrees 2-theta (+/−0.2) at 4.0, 11.4, 11.8, and 19.8.

* * * * *

UNITED STATES PATENT AND TRADEMARK OFFICE
CERTIFICATE OF CORRECTION

PATENT NO. : 11,203,569 B2
APPLICATION NO. : 16/493789
DATED : December 21, 2021
INVENTOR(S) : Almarsson et al.

It is certified that error appears in the above-identified patent and that said Letters Patent is hereby corrected as shown below:

In the Claims

At Column 47, Claim number 3, Line number 51:
"The salt or cocrystal of claim 1, wherein said salt or"
Should read:
--The salt or cocrystal of claim 2, wherein said salt or--

At Column 47, Claim number 3, Line number 54:
"values substantially in accordance with FIG. 36, 38, 40, 42"
Should read:
--values substantially in accordance with Figure 36, 38, 40, 42--

At Column 47, Claim number 4, Line number 56:
"The salt or cocrystal of claim 1, wherein the salt or"
Should read:
--The salt or cocrystal of claim 2, wherein the salt or--

At Column 47, Claim number 4, Line number 59:
"shown in FIG. 37, 39, 41, 43, or 45."
Should read:
--shown in Figure 37, 39, 41, 43, or 45.--

At Column 47, Claim number 7, Line number 64:
"The salt or cocrystal of claim 1, wherein the stoichi-"
Should read:
--The salt or cocrystal of claim 2, wherein the stoichi- --

At Column 48, Claim number 8, Line number 21:
"The salt or cocrystal of claim 1, wherein the stoichi-"

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*

Should read:
--The salt or cocrystal of claim 2, wherein the stoichi- --

At Column 48, Claim number 9, Line number 26:
"The salt or cocrystal of claim 1, wherein the salt or"
Should read:
--The salt or cocrystal of claim 2, wherein the salt or--

At Column 48, Claim number 10, Line number 33:
"values substantially in accordance with FIG. 38."
Should read:
--values substantially in accordance with Figure 38.--

At Column 48, Claim number 11, Line number 37:
"shown in FIG. 39."
Should read:
--shown in Figure 39.--

At Column 48, Claim number 16, Line number 58:
"The salt or cocrystal of claim 1, wherein the salt or"
Should read:
--The salt or cocrystal of claim 2, wherein the salt or--

At Column 48, Claim number 17, Line number 64:
"The salt or cocrystal of claim 1, wherein the salt or"
Should read:
--The salt or cocrystal of claim 2, wherein the salt or--

At Column 49, Claim number 18, Line number 3:
"The salt or cocrystal of claim 1, wherein the salt or"
Should read:
--The salt or cocrystal of claim 2, wherein the salt or--

At Column 49, Claim number 19, Line number 10:
"The salt or cocrystal of claim 1, wherein the salt or"
Should read:
--The salt or cocrystal of claim 2, wherein the salt or--

At Column 49, Claim number 20, Line number 17:
"The salt or cocrystal of claim 1, wherein the salt or"
Should read:
--The salt or cocrystal of claim 2, wherein the salt or--